United States Patent
Weber et al.

(10) Patent No.: US 12,296,186 B2
(45) Date of Patent: May 13, 2025

(54) SYSTEM FOR PERFORMING TRANSCUTANEOUS PHOTODYNAMIC THERAPY (PDT) IN AN ORGAN OR ORGAN SEGMENT OF AN ORGANIC BODY

(71) Applicant: Richard Wolf GmbH, Knittlingen (DE)

(72) Inventors: Bernd Claus Weber, Karlsruhe (DE); Stephan Sieber, Knittlingen-Freudenstein (DE); Klaus Müller, Knittlingen-Freudenstein (DE)

(73) Assignee: RICHARD WOLF GMBH, Knittlingen (DE)

( * ) Notice: Subject to any disclaimer, the term of this patent is extended or adjusted under 35 U.S.C. 154(b) by 408 days.

(21) Appl. No.: 17/960,919

(22) Filed: Oct. 6, 2022

(65) Prior Publication Data

US 2023/0111389 A1    Apr. 13, 2023

(30) Foreign Application Priority Data

Oct. 7, 2021   (DE) .................. 10 2021 211 331.1

(51) Int. Cl.
*A61N 5/06* (2006.01)

(52) U.S. Cl.
CPC ........ *A61N 5/06* (2013.01); *A61N 2005/0612* (2013.01); *A61N 2005/0643* (2013.01); *A61N 2005/0651* (2013.01)

(58) Field of Classification Search
CPC .............. A61N 5/06; A61N 2005/0612; A61N 2005/0643; A61N 2005/0651
See application file for complete search history.

(56) References Cited

U.S. PATENT DOCUMENTS 6,048,359 A    4/2000  Biel
11,583,338 B2 *  2/2023  Gowda .................. A61N 7/00
(Continued)

FOREIGN PATENT DOCUMENTS

DE    102019212201 A1    2/2021
DE    102019129556 A1    5/2021
(Continued)

OTHER PUBLICATIONS

Famulari Gabriel et al: "A novel 169 Yb-based dynamic-shield intensity modulated brachytherapy delivery system for prostate cancer", Medical Physics., [Online] Bd. 4 7 , Nr . 3, Dec. 30, 2019 (Dec. 30, 2019), Seiten 859-868, XP093024936, US ISSN: 0094-2405, DOI: 10.1002/mp.13959 Gefunden im Internet: URL:https://onlinelibrary.wiley.com/doi/full-XML/10.1002/mp.13959> [Feb. 20, 2023].

*Primary Examiner* — Shirley X Jian
(74) *Attorney, Agent, or Firm* — McGlew and Tuttle, P.C.

(57) ABSTRACT

A system, for transcutaneous photodynamic therapy in an organ or organ segment of an organic body, includes a plurality of light applicators (9), a supply unit (23) and a placement template (39) placeable relative to the organic body for defined orientation of the light applicators. The light applicators include a needle-shaped insertion portion (15) for transcutaneous piercing along a piercing axis (E), a light-emitting applicator tip (19) at the distal end (13) of the insertion portion, and a fixing point (43) at a proximal distance d from the applicator tip. The placement template defines a plurality of fixing point receptacles (51) for fixing the light applicators with a defined fixing point and includes a first and second template parts (71, 75) defining first and second subsets (73, 77) of fixing point receptacles. The first template part is guidingly displaceable relative to the second template part along the piercing axis.

15 Claims, 37 Drawing Sheets

(56) References Cited

U.S. PATENT DOCUMENTS 12,035,969 B2 * 7/2024 Goodrich ........... A61K 41/0028
2009/0156958 A1 6/2009 Mehta et al.
2010/0329524 A1 12/2010 Swartling et al.

FOREIGN PATENT DOCUMENTS

| EP | 3777974 A1 | 2/2021 |
| WO | 2010091008 A1 | 8/2010 |
| WO | 2018112261 A1 | 6/2018 |

* cited by examiner

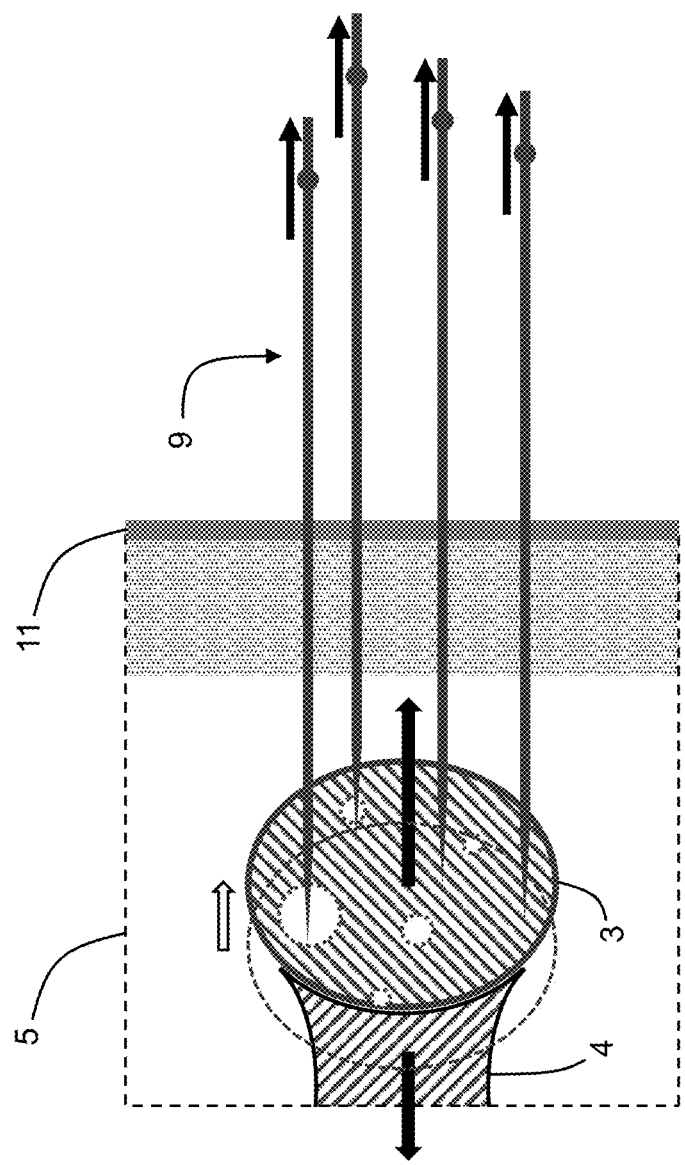
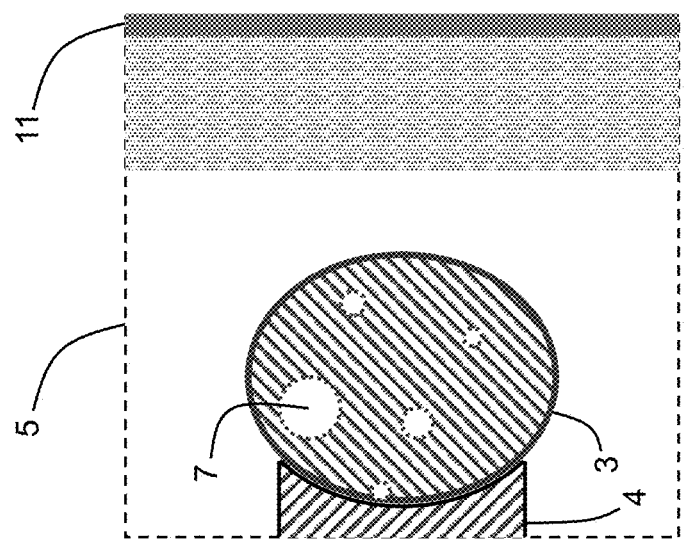
Fig. 25b
Fig. 25a

SYSTEM FOR PERFORMING TRANSCUTANEOUS PHOTODYNAMIC THERAPY (PDT) IN AN ORGAN OR ORGAN SEGMENT OF AN ORGANIC BODY

CROSS REFERENCE TO RELATED APPLICATIONS

This application claims the benefit of priority under 35 U.S.C. § 119 of German Application 10 2021 211 331.1, filed Oct. 7, 2021, the entire contents of which are incorporated herein by reference.

TECHNICAL FIELD

The present disclosure relates to a system for performing transcutaneous photodynamic therapy (PDT) in an organ or organ segment of an organic body.

BACKGROUND

PDT is a known medical therapy of a patient's pathological tissue. For this purpose, a photosensitiser or marker substance is administered to the patient and selectively accumulates on the pathological tissue to be treated. In PDT, light is then applied directly to or even into the pathological tissue by means of a light applicator or several light applicators in order to promote the light-induced formation of oxygen radicals by means of the locally enriched photosensitiser or marker substance and thereby destroy the pathological tissue, such as a tumour. Typically, laser light is coupled into a light guide and directed to the tissue. If the pathological tissue is located on an external surface of the body, e.g. the skin, or an internal surface, e.g. the inner surface of the oesophagus or intestinal walls, then it is relatively easy to outcouple the therapy light and shine it onto the pathological tissue surface. However, if the pathological tissue extends over a volume in an internal organ or organ segment, it is not always possible to effectively irradiate a tumour from the "outside" due to the limited penetration depth of the light into the tissue. In this case, PDT is particularly effective if the light is irradiated from inside the pathological tissue volume. To do this, the light applicator or the light applicators must be pierced into the pathological tissue. This is also called interstitial (through internal surfaces) and/or transcutaneous (through the skin) PDT. For example, U.S. Pat. No. 6,048,359 describes a system for performing transcutaneous PDT to irradiate an internal volume within a patient's body. A plurality of needle-like (needle-shaped) light applicators are pierced in parallel through the skin into the body, wherein each light applicator has lateral light outcoupling means distributed along its length to thus irradiate a volume in the body.

The disadvantage of the known solution is that, firstly, the light applicators have to be relatively thick and, secondly, they are relatively complex and costly, so that, firstly, they are relatively burdensome for the patient, particularly in total, and, secondly, they cannot be produced as disposable articles for one-time use.

SUMMARY

This results in an object of providing a more cost-effective system for performing transcutaneous PDT with thinner and thus more patient-friendly light applicators, wherein the system is intended to allow gap-free irradiation of the organ or organ segment.

According to a first aspect of the present disclosure, to solve this problem, a system for performing transcutaneous PDT in an organ or organ segment of an organic body is provided, in which the system comprises a plurality of individually manually placeable light applicators, a supply unit for supplying the light applicators with light and/or power, and a placement template placeable in a defined position relative to the organic body for defined orientation, positioning, and fixing of the individual light applicators in or on the placement template and thus ultimately for defined placement of the light-emitting applicator tips in the organ or organ segment. For this purpose, the individually placeable light applicators each have a needle-like (needle-shaped) insertion portion for transcutaneous piercing along a piercing axis into the organ or organ segment, a light-emitting applicator tip at the distal end of the insertion portion, and at least one defined fixing point at a proximal distance d from the light-emitting applicator tip. In addition, the placement template defines a plurality of fixing point receptacles by means of which the individual light applicators can be fixed with their at least one defined fixing point, wherein the fixing point receptacles are arranged in or on the placement template in accordance with a three-dimensional fixing point grid structure, wherein the fixing point grid structure corresponds to a virtual organ-specific target point grid structure for the light-emitting applicator tips in the organ or organ segment and is arranged parallel-displaced relative to the target point grid structure by the distance d along the piercing axis. The placement template can define a plurality of guides, wherein the insertion portions of each of the light applicators are able to be pierced transcutaneously in a manner guided by one each of the guides into the organ or organ segment along a piercing axis. The fixing point receptacles can be formed on or in the guides.

The basic procedure and the underlying concept with the structure described above consist in the realisation and positioning of the placement template outside the body in a first step to map the virtual three-dimensional target point grid structure by means of a parallel displacement or translation by the distance d onto a three-dimensional fixing point grid structure. On the one hand, the virtual three-dimensional target point grid structure represents the defined target arrangement of the light-emitting applicator tips in the organ or organ segment with regard to a gap-free irradiation of the organ or organ segment. The operator should therefore gradually populate the target points of the target point grid structure with the individual light-emitting applicator tips. However, the target points of the target point grid structure in the patient's body are not visible to the operator and therefore cannot initially be steered towards in a targeted manner or directly with the light-emitting applicator tips. The fixing point grid structure, which is represented by the fixing point receptacles in or on the placement template outside the patient's body, is, in contrast to the virtual target points of the virtual target point grid structure located inside the body, visible to the operator and can be steered towards in a targeted manner and directly with the at least one fixing point of a corresponding light applicator. After the first step of the parallel displacement or translation, the individual light-emitting applicator tips in a second step, by means of a parallel displacement that is inverse to the parallel displacement described above, are thus placed at the virtual and, for the operator, invisible target points of the virtual target point grid structure in the organ or organ segment in a defined, unambiguous and thus reliable manner.

In the first step, the virtual, invisible organ-specific target point grid structure inside the body, which therefore cannot be steered towards directly, is transformed or mapped by means of a parallel displacement or translation into or onto the fixing point grid structure, represented by the real, visible and therefore directly accessible fixing point receptacles of the placement template, outside the body.

After this first step, the second step is the performing of the actual therapy preparation by the operator, which consists of the proper distribution and placement of the individual light applicators or the light-emitting applicator tips in the patient in view of a gap-free irradiation of the organ or organ segment. In this second step, the light-emitting applicator tips—starting from the visible fixing point receptacles of the placement template outside the body, which can be steered towards directly—are transformed or moved to the invisible target points inside the body in a defined, unambiguous and thus reliable manner by means of the parallel displacement which is inverse to the parallel displacement of the first step. The definiteness and unambiguity in the placement of the individual applicator tips in the target points is achieved in accordance with the invention in that, firstly, the placement template is provided with guides oriented parallel to each other for a defined, unambiguous, parallel orientation of the individual light applicators and in that, secondly, on the one hand, the placement template is provided with fixing point receptacles and, on the other hand, the light applicators are provided with at least one fixing point by which the light applicators can be fixed in or on the fixing point receptacles of the placement template at a defined and unambiguous point, thus achieving a defined and unambiguous penetration depth of the light applicators into the organ or organ segment.

The individual light applicators can be formed particularly thin and rigid as a metal shaft and/or tube, since only the applicator tip needs to be configured to emit light. For example, a light-emitting component in the form of a light guide outcoupling means or an LED can be arranged at the applicator tip. The applicator tip can be arranged as a light-transparent diffuser distally of the light-emitting component. The system for performing transcutaneous PDT is thus much gentler on the tissue and less invasive than systems known from the prior art. Due to the three-dimensional fixing point grid structure, which emerges from the target point grid structure by the parallel displacement by the length d along the piercing axis explained above, with on the one hand fixing point receptacles arranged according to this three-dimensional fixing point grid structure, and with on the other hand guides, which both together (fixing point receptacle and guide) in combination with the at least one light applicator fixing point permit a movement and final placement of the light applicators and the light-emitting applicator tips in the body and in the organ exclusively according to a parallel displacement inverse to the above-explained parallel displacement, and in this sense reduce the operator's degrees of freedom in this respect to a minimum, it is ensured that the light-emitting applicator tips are arranged in accordance with the target point grid structure in the organ or organ segment such that the organ or organ segment is irradiated gap-free over the entire volume of the target point grid structure. Each grid point of the target point grid structure is preferably occupied here by an applicator tip. However, this does not necessarily have to be done simultaneously. Transcutaneous PDT can be carried out particularly quickly if all grid points of the target point grid structure are gradually occupied by one applicator tip each and the entire organ or organ segment is then irradiated simultaneously. Alternatively, transcutaneous PDT can be performed successively for different grid points or grid point groups of the target point grid structure. In this way, the number of light applicators and/or piercing operations required can be reduced, at the cost of a longer treatment time, which may reduce the patient burden and the costs of the treatment.

For example, the target point grid structure can have a plurality of target point grid areas that have a grid area spacing k along the piercing axis. The target point grid areas can extend flat as target point grid planes or curved as part of the target point grid structure. Percutaneous PDT can then be performed successively for one target point grid area after another. For example, an operator can start with a lowest target point grid area and then work their way forward by pulling out the light applicators proximally by one grid area distance k target point grid area for target point grid area until the entire target point grid structure has been irradiated and thus the organ or organ segment has been irradiated gap-free.

The virtual organ-specific target point grid structure lies inside the organic body distributed over the organ or organ segment and is thus not visible to the operator. The three-dimensional fixing point grid structure, on the other hand, which is preferably defined by the placement template with its fixing point receptacles and the light applicators with their fixing points in combination with each other, is located outside the body so that it can be seen by the operator and ensures that the light-emitting applicator tips are located at the corresponding grid points of the target point grid structure when the fixing point of the relevant light applicator is located at the associated grid point of the fixing point grid structure, i.e. in the corresponding fixing point receptacle of the placement template.

For example, an operator can insert a first light applicator into the organ or organ segment through a guide that is firstly centrally located in the placement template and secondly has its associated fixing point receptacle located largely distally in the placement template. The operator can then place the applicator tip of this first light applicator at a grid point of the target point grid structure in the organ or organ segment corresponding to this fixing point receptacle, i.e. likewise largely distally of and centrally arranged within this selected, distal target point grid plane by means of an imaging procedure, for example by means of ultrasound sonography. The patient's body is preferably fixed here relative to a fixed reference surface, for example a treatment table. With the first light applicator or its light-emitting applicator tip correctly positioned and while maintaining this selected light applicator position, the placement template can then be moved relative thereto along the piercing axis and can be positioned so that the fixing point of the first light applicator is located at the corresponding grid point of the fixing point grid structure. In this position, both the fixing point of the light applicator can be fixed to the fixing point receptacle of the placement template and the placement template can be fixed to the outer reference surface, for example a treatment table.

With this process, the three-dimensional fixing point grid structure is spatially defined in relation to the patient's body. In addition, this process, by which the defined distance d between the virtual target point grid structure and the fixing point grid structure is established, also completes the first step of the procedure according to the invention, namely the first mapping, i.e. the parallel displacement or translation of the virtual target point grid structure in the organ or organ segment within the human body into an area outside the human body.

The placement of the further individual light applicators is now particularly easy, error-free and quick to carry out, as they only need to be pierced through the corresponding guides of the placement template and advanced until their fixing point is located in the corresponding grid point of the fixing point grid structure, i.e. in the fixing point receptacle of the placement template. The applicator tip is then automatically located at the associated grid point of the target point grid structure. The virtual organ-specific target point grid structure ensures that, on the one hand, the applicator tips are not too far apart from each other so that no irradiation gaps occur in the organ or organ segment and, on the other hand, are not arranged too close to each other so that the patient does not have to be burdened with an unnecessary number of piercing operations. The target point grid structure is organ-specific since the outer shape and size of the target point grid structure depends on the organ or organ segment. In addition, the density of the target points of the target point grid structure depends on how great the penetration depth of the light is into the tissue of the particular organ or organ segment. The smaller the penetration depth of the irradiation light, the denser the target point grid structure must be selected to ensure gap-free irradiation of the organ or organ segment.

Optionally, the supply unit can be set up to supply the light applicators with power, wherein each light applicator has an LED, operable with the power, and/or another light-emitting component at the distal end of the insertion portion. Compared to a light guide outcoupling means, an LED and/or another corresponding light-emitting component at the distal end of the insertion portion has the great advantage that no costly laser is required, the light of which must be coupled into the light guide via the supply unit. Since the supply unit only has to supply the light applicators with power, it can be formed in a particularly simple and cost-effective way. The LED and/or the other light-emitting component preferably has a light spectrum matched to the photosensitiser or marker material. Alternatively or additionally, a light filter can be used for this purpose.

Optionally, the fixing point receptacles are each arranged in or on an associated guide or are formed by the latter.

Optionally, the light applicators can each have at least one fixing point, which is formed by a stop and can be locked to a fixing point receptacle of the placement template in accordance with the three-dimensional fixing point grid structure. Through the stop and the locking, an operator receives a haptic, acoustic and/or visual feedback regarding the correct placement of the fixing point at a grid point of the fixing point grid structure or the corresponding fixing point receptacle.

Optionally, the virtual organ-specific target point grid structure can have a plurality of target points spatially distributed on target point grid areas, wherein the target point grid areas have a distance k from each other along the piercing axis. Preferably, the target point grid areas extend transversely to the piercing axis.

Optionally, the light applicators can each have at least two fixing points which have the same distance k from each other along the piercing axis as the target point grid areas have from each other along the piercing axis. This allows the operator to select one of the fixing points and to fix it to the corresponding grid point of the fixing point grid structure or the associated fixing point receptacle of the placement template, thereby defining the target point grid area in which the applicator tip should lie.

Optionally, the placement template can have a plurality of fixing point receptacles spatially distributed on fixing point receptacle grid areas, wherein the fixing point receptacle grid areas have the same distance k from each other along the piercing axis as the corresponding target point grid areas also have from each other along the piercing axis. By selecting the fixing point receptacle in which the fixing point is to be locked, an operator has the possibility of determining the target point grid area in which the applicator tip is to lie.

Optionally, the virtual organ-specific target point grid structure can have a plurality of target points arranged spatially distributed on target point grid areas, wherein at least eight of the target points form corner points of a grid elementary cell of the target point grid structure in the form of a parallelepiped. Preferably, the grid elementary cell has three grid elementary cell edges and four grid elementary cell diagonals, one or none of which runs along the piercing axis. The variant in which none of the three grid elementary cell edges or four grid elementary cell diagonals runs along the piercing axis has the advantage that a plurality of target point grid areas can be occupied simultaneously with applicator tips and thus PDT can be performed more quickly. By contrast, the variant in which one of the three grid elementary cell edges or the four grid elementary cell diagonals runs along the piercing axis has the advantage that one piercing operation can be used for a plurality of target point grid areas and thus, on the one hand, fewer piercing operations are required, which is more tissue-friendly for the patient, and, on the other hand, fewer light applicators are required, which makes the system more cost-effective.

According to a second aspect of the present disclosure, which is preferably combinable with the first aspect or independent thereof, a system for performing transcutaneous PDT in an organ or organ segment of an organic body is provided, wherein the system comprises a plurality of light applicators, a supply unit for supplying the light applicators with light and/or power, and a placement template placeable in a defined position relative to the organic body for defined orientation, placement and fixing of the light applicators. The light applicators each have a needle-like insertion portion for transcutaneous piercing along a piercing axis into the organ or organ segment and a light-emitting applicator tip at the distal end of the insertion portion, as well as at least one defined fixing point at a proximal distance d from the applicator tip. In addition, the placement template defines a plurality of fixing point receptacles by means of which the light applicators can be fixed with their at least one defined fixing point. The placement template can define a plurality of guides, wherein the insertion portions of each of the light applicators are able to be pierced transcutaneously in a manner guided by one of the guides into the organ or organ segment along a piercing axis. The fixing point receptacles can be formed on or in the guides.

According to the second aspect, the placement template comprises at least one first template part defining a first subset of the fixing point receptacles and at least one second template part defining a second subset of the fixing point receptacles, wherein the first template part is displaceable in a guided manner relative to the second template part along the piercing axis.

Through the template parts, different subsets of light applicators can be selectively moved or held jointly in a concerted manner by means of fixing in corresponding subsets of fixing point receptacles. This makes it possible to hold the organ or organ segment in place or maintain its shape with one subset of light applicators while the other subset is moved.

Such a system and such a procedure may be advantageous for the following reason. If a light applicator inserted into the organ or organ segment is moved or displaced, it exerts a static frictional force on the organ or organ segment or on the organ tissue that is in contact with the light applicator. If the light applicators are all moved jointly or simultaneously in a direction, then the sum of these static frictional forces on the organ or organ segment in this direction is also correspondingly large. Depending on the different boundary conditions explained below, two fundamentally different, relevant cases can occur, which can also occur in combined form.

In a first case, which is based on the boundary condition that the total static frictional force acting on the organ or organ segment when the light applicators are moved jointly or simultaneously in a direction is greater than the binding forces acting within the surrounding tissue directly connected to the organ or organ segment to be treated and is in turn smaller than the binding forces acting within the organ or organ segment itself, the organ or organ segment can be "carried along" as a whole and unchanged in its shape by the light applicators moved jointly or simultaneously in a common direction, i.e. when the light applicators are moved jointly or simultaneously in a direction under the aforementioned boundary conditions, the organ or organ segment maintains its shape, but changes its position in the body. In this first case, the target point grid structure would then remain unchanged in its shape and would thus continue to correspond to the shape of the fixing point grid structure, but the position of the target point grid structure would change compared to the continued unchanged position of the fixing point grid structure, i.e. the fixing point grid structure would no longer be parallel-displaced along the piercing axis in an undesirable way by the original length d, which characterises the parallel displacement and corresponds to the distance d between the applicator tip and the fixing point.

In a second case, which is based on the boundary condition that the total static frictional force acting on the organ or organ segment when the light applicators move jointly or simultaneously in a direction is greater than the binding forces acting within the organ or organ segment itself, which in turn are smaller than the binding forces acting within the surrounding tissue directly connected to the organ or organ segment to be treated, the organ or organ segment can be extended or stretched in the direction of movement of the light applicators, i.e. when the light applicators are displaced jointly or simultaneously in a direction under the previously mentioned boundary conditions, the organ or organ segment maintains its position in the body in a first approximation, but changes its shape. In this second case, the position of the target point grid structure would then indeed be unchanged compared to the position of the fixing point grid structure in a first approximation, i.e. the distance between the two grid structures would still correspond to the length d characterising the parallel displacement in a first approximation after the joint or simultaneous displacement of the light applicators, but the shape of the target point grid structure would change in the same way with the shape of the organ and in turn would then no longer correspond to the shape of the fixing point grid structure.

In both cases, or a combination thereof, such a "dragging effect" would be negative, since, from a mathematical-geometrical point of view, in both cases the original parallel displacement by the length d, through which the fixing point grid structure emerged from the target point grid structure and which forms the basis of the procedure presented here for a complete and, above all, precise treatment of the organ or organ segment, would be impaired or modified, i.e. characteristic parameters of the parallel displacement (object shape, displacement length d) would be changed and therefore a uniform and above all gap-free irradiation would no longer be automatically ensured.

Both explained cases of the "dragging effect" or effects thereof gain in importance with increasing number of light applicators, because each additional light applicator exerts an additional static frictional force on the organ or organ segment at its contact surface with the organ or organ segment, which is substantially formed by the light applicator shaft, which further increases the total static frictional force. Thus, as the number of light applicators increases, the likelihood increases that the total static frictional force will either exceed the binding forces within the surrounding tissue directly connected to the organ (first case described above) and/or exceed the binding forces within the organ or organ segment itself (second case described above), resulting in either a displacement of the organ or organ segment in a proximal direction (first case described above), and/or a deformation of the organ or organ segment (second case described above).

The "dragging effect" can be avoided by holding one subset of light applicators while moving or displacing or pulling out the other subset. The respective subsets can be moved alternately while the other is held. The joint movement and joint holding of the light applicators can be effected by corresponding movement or holding, respectively, of the template parts.

Optionally, the first subset of the fixing point receptacles can define a first fixing point receptacle sub-grid and the second subset of the fixing point receptacles can define a second fixing point receptacle sub-grid, wherein the second fixing point receptacle sub-grid is offset from the first fixing point receptacle sub-grid by a lateral grid offset transversely to the piercing axis. Preferably, each light applicator thereby has at least one other light applicator as a laterally nearest neighbour, which is fitted in the other subset of guides. In this way, the "dragging effect" can be avoided particularly well, because the resulting static frictional forces of neighbouring light applicators cancel each other out in pairs in a first approximation and thus the total static frictional force is also zero. In addition, local displacements and/or deformations of the organ or organ segment can thus also be avoided. Preferably, the first fixing point receptacle sub-grid has approximately the same number of fixing point receptacles as the second fixing point receptacle sub-grid.

Optionally, the lateral grid offset can be smaller than a side length of a grid elementary cell of the first fixing point receptacle sub-grid and/or the second fixing point receptacle sub-grid. Preferably, the side length of a grid elementary cell of the first fixing point receptacle sub-grid and the second fixing point receptacle sub-grid is identical and the lateral grid offset is half the side length of a grid elementary cell. The grid offset can preferably be provided in two orthogonal lateral directions so that a fixing point receptacle of the first fixing point receptacle sub-grid forms the centre point of a grid cell of the second fixing point receptacle sub-grid, and vice versa.

Optionally, the first fixing point receptacle sub-grid and the second fixing point receptacle sub-grid can be located in a fixing point receptacle grid area. In this way, the fixing point receptacle sub-grids complement each other to form an entire fixing point receptacle grid in a fixing point receptacle grid area. Such an arrangement—in comparison with the arrangement described below—has the advantage that when a template part representing one of the two fixing point receptacle sub-grids is moved or displaced, the frictional forces pointing in opposite directions are cancelled out even better, because the shaft lengths determining the frictional forces are the same or similar within the organ or organ segment, because they project at least temporarily in pairs to the same extent into the organ or organ segment. For the intended cancellation of the frictional forces in pairs, it is first assumed for simplification that both fixing point receptacle grid areas are occupied by the same number of applicators. However, if the fixing point receptacle sub-grids were not in the same fixing point receptacle grid area, it may be that the frictional forces no longer compensate each other completely in pairs since the respective shaft lengths which are located within the organ or organ segment differ. This can be fully or partially corrected by fitting a higher number of light applicators to the fixing point receptacle sub-grid or the corresponding template part that is moved first in the proximal direction.

Optionally, the first subset of the guides and fixing point receptacles, the second subset of the guides and fixing point receptacles and the light applicators together define a three-dimensional fixing point grid structure, wherein the fixing point grid structure corresponds to a virtual organ-specific target point grid structure for the light-emitting applicator tips in the organ or organ segment and is parallel-displaced relative to the target point grid structure by a length d along the piercing axis, wherein each light applicator has at least one defined fixing point at the distance d from the applicator tip.

Optionally, the supply unit can be set up to supply the light applicators with power and each light applicator can have an LED, operable with the power, and/or another light-emitting component at the distal end of the insertion portion. Compared to a light guide outcoupling means, an LED at the distal end of the insertion portion has the great advantage that no costly laser is required, the light of which must be coupled into the light guide via the supply unit. Since the supply unit only has to supply the light applicators with power, it can be formed in a particularly simple and cost-effective way. The LED preferably has a light spectrum matched to the photosensitiser or marker material. Alternatively or additionally, a light filter can be used for this purpose.

Optionally, the light applicators can each have at least one fixing point that is formed by a stop and can be locked. Through the stop and the locking, an operator receives a haptic, acoustic and/or visual feedback regarding the correct placement of the fixing point at a grid point of the fixing point grid structure or the corresponding fixing point receptacle of the placement template or the template part.

Optionally, the virtual organ-specific target point grid structure can have a plurality of target points spatially distributed on target point grid areas, wherein the target point grid areas have a distance k from each other along the piercing axis. Preferably, the target point grid areas extend orthogonally to the piercing axis.

Optionally, at least eight of the target points can form corner points of a grid elementary cell of the target point grid structure in the form of a parallelepiped. Optionally, the grid elementary cell can have three grid elementary cell edges and four grid elementary cell diagonals, one of which runs along the piercing axis. This makes it particularly easy to position all the light applicators guided in the first template part jointly at the same time by displacing the first template part such that the corresponding light-emitting applicator tips are guided from one set-point grid area to the next. Meanwhile, the light applicators guided by the second template part can be held stationary and can thus hold the organ or organ segment in place and/or suppress its deformation, while the light applicators guided in the first template part are moved jointly. As soon as the light applicators guided in the first template part are placed in position, they can be held stationary while the light applicators guided in the second template part are moved with their light-emitting applicator tips to the next target point grid area. Preferably, this process begins with the target point grid area of the particular template part that is located distally deepest in the body, working then proximally to the next target point grid area by retracting the particular template part. PDT can then be performed each time the applicator tips are positioned at their target point in the target point grid.

Optionally, a first subset of the target points corresponding to the first subset of the guides or fixing point receptacles can define a first target point sub-grid and a second subset of the target points corresponding to the second subset of the fixing point receptacles can define a second target point sub-grid, so that the first target point sub-grid and the second target point sub-grid supplement each other to form one of the target point grid areas. In this way, each target point grid area can be completely populated with light-emitting applicator tips by first filling one target point sub-grid with light-emitting applicator tips and then populating the other target point sub-grid. This can be done easily by displacing the template parts relative to each other correspondingly.

Optionally, the light applicators can each have at least two fixing points which have the same distance k from each other along the piercing axis as the target point grid areas have from each other. This allows the operator to determine in which target point grid area the light emitting applicator tip is to lie by means of one of the fixing points, which is to be locked in the grid point of the fixing point grid structure or in the corresponding fixing point receptacle of the particular template part.

Optionally, the placement template can have a plurality of fixing point receptacles spatially distributed on fixing point receptacle grid areas, wherein the fixing point receptacle grid areas have the same distance k from each other along the piercing axis as the target point grid areas also have from each other. This allows an operator to determine in which target point grid area the applicator tip is to lie by selecting one of the fixing point receptacles in which a fixing point is to be locked.

Optionally, the first template part comprises a first subset of the fixing point receptacles of a first fixing point receptacle grid area and the second template part can comprise a second subset of the fixing point receptacles of a second fixing point receptacle grid area. The two subsets of fixing point receptacles can therefore supplement each other via two fixing point grid areas of the fixing point grid structure.

Optionally, the second template part is displaceable in the proximal direction relative to the first template part only until it contacts the first template part, wherein, when the second template part is in contact with the first template part, the first subset of the fixing point receptacles defined by the first template part lies distally of the second subset of the fixing point receptacles defined by the second template part.

In the following, the system disclosed herein is explained in greater detail with reference to the accompanying figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 25a and FIG. 25b are schematic representations of the dragging effect to be avoided in principle according to the first variant;

DESCRIPTION OF PREFERRED EMBODIMENTS

Figure 1:
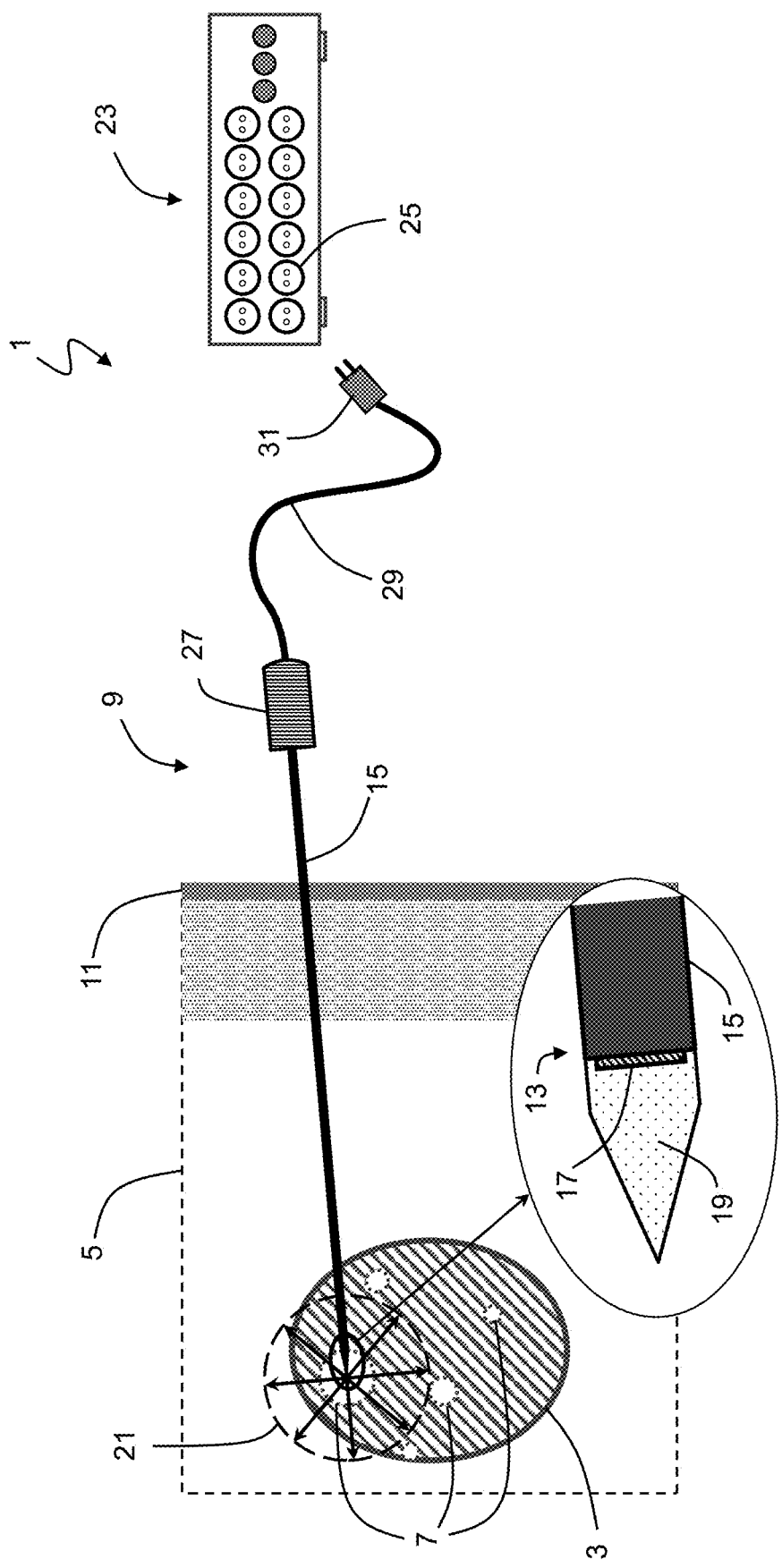
FIG. 1 is a schematic representation of the primary mode of operation of a percutaneous PDT with a light applicator.

Referring to the drawings, FIG. 1 shows a system 1 for performing transcutaneous photodynamic therapy (PDT) in an organ 3, for example the prostate, of an organic body 5. Here, the organ 3 has a plurality of pathological tissue areas 7 (all denoted in the figures by a dotted outline) in which an administered photosensitiser or marker substance has accumulated. However, not all pathological tissue areas 7 can be visualised, for example due to their small size and/or their insufficient contrast, and accordingly, i.e. due to their partial invisibility for the operator, they cannot all be treated individually in a targeted manner, i.e. focally or tissue-specifically. However, it is known from experience, for example by taking random biopsies from the organ 3, that such pathological tissue areas 7 nevertheless almost always exist. All of the visible and invisible pathological tissue areas 7 are now to be irradiated with light in order to achieve a corresponding therapeutic effect on all pathological tissue areas 7. If certain pathological tissue areas 7, for example a tumour, are not irradiated, they remain untreated and may grow larger or otherwise remain or become medically harmful.

FIG. 1 shows that the system 1 has a needle-like light applicator 9 which is pierced through the skin 11 of the body 5, i.e. transcutaneously, into the organ 3. The light applicator 9 is as thin as possible in order to damage as little healthy tissue of the body 5 as possible by the piercing operation, i.e. to allow a minimally invasive procedure. A light-emitting element 17 in the form of an LED is arranged at the distal end 13 of a thin shaft-shaped insertion portion 15 of the light applicator 9. On the distal side of the LED 17, a light-transparent and light-diffusing applicator tip 19 is arranged at the distal end 13 of the insertion portion 15 of the light applicator 9. The applicator tip 19 emits the light of the LED 17 as isotropically as possible in a solid angle of more than $3\pi$. The light emission from the applicator tip 19 is thus approximately spherical, which is indicated in FIG. 1 by a dashed light sphere 21 or in the present sectional view by a dashed circle. The size of the light sphere 21 as an orientation or measure of the tissue area or tissue volume in which a sufficiently high amount of light still arrives in respect of the desired therapeutic effect depends on the penetration depth of the light into the tissue of the organ 3 and is therefore organ-specific.

The system 1 further comprises a supply unit 23 with which the light applicator 9 is supplied with power with which the LED 17 is operated. The supply unit 23 preferably has a plurality of ports 25 for a plurality of individual light applicators 9 that can be used simultaneously in PDT. The light applicator 9 has a grip element 27 at the proximal end of the insertion portion 15, and an operator can manually grip and position the light applicator 9 by means of the grip element. A cable 29 with a plug 31 that fits into one of the ports 25 of the supply unit 23 can be used to connect and power each of the light applicators 9. The insertion portion 15 of the light applicator 9 preferably comprises a core and a sheath electrically insulated from the core, such that the core and sheath can act as a forward and return pair to supply power to the LED 17. Alternatively or additionally, an extra conductor can be provided in the insertion portion 15 of the light applicator 9.

In FIG. 1, it is already clear from the light sphere 21 and its size that the penetration depth of the light is not sufficient to irradiate the entire organ 3 by one piercing operation. However, the aim is to irradiate the entire organ 3 gap-free, because on the one hand, in the procedure presented here, the irradiation with light is harmless to healthy tissue, because due to the comparatively small amount of light applied in PDT, a destructive effect can only take place where the photosensitiser is located, where the photosensitiser has accumulated, which only happens in malignant tissue due to the tumour selectivity of the selected photosensitiser, and on the other hand it is to be ensured that no pathological tissue area 7, and in particular also no pathological tissue area 7 in the organ 3 that is invisible to the operator, remains untreated. An operator would therefore have to pierce the light applicator 9 again at other points after an irradiation in order to gradually, i.e. sequentially, cover the entire volume of the organ 3 with the corresponding light spheres 21.

However, such a procedure requires very good experience on the part of the operator and is associated with many risks and disadvantages. On the one hand, it cannot be ensured that, at the end, the entire volume of the organ 3 has been irradiated gap-free, because on the one hand the operator has a great deal of freedom in the placement of the light applicators 9 in the organ 3 and because on the other hand the area that has been therapeutically effectively covered, or its boundaries, which are represented in FIG. 1 by the surface of the light sphere 21 or by the circumference of the circle in the sectional image shown there, are not directly visualised and thus cannot be made directly visible to the operator for checking purposes, and thus there is no certainty whether the light applicator 9 or its light-emitting applicator tip 19 has always been placed in the correct position. On the other hand, it may be necessary to "poke around", in which case too many piercing operations are required, which burdens the patient. Lastly, PDT in this form can take a very long time.

Figure 2:
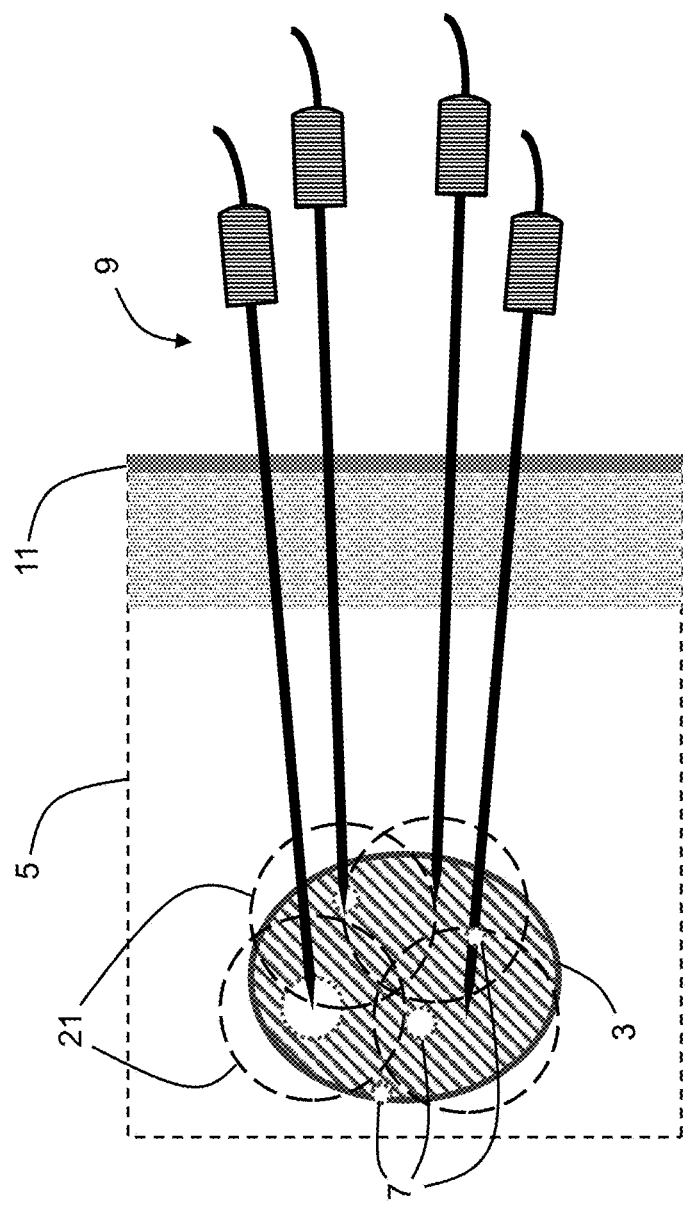
FIG. 2 is a schematic representation of the primary mode of operation of a percutaneous PDT with a plurality of light applicators with a relatively high penetration depth of the light.

FIG. 2 shows how PDT can be accelerated if a plurality of individual light applicators 9 are used simultaneously. This makes the system 1 more costly, but saves time. Here too, however, great experience is required on the part of the operator, because in this case too, as described above for the sequential placement of a single light applicator 9, it can be seen that despite the supposedly gap-free irradiation of the organ 3, a pathological tissue area 7 in the organ 3 has remained untreated without being noticed (in FIG. 2 on the far left), because here too, on the one hand, the described procedure performed by the operator in the placement of the individual light applicators 9 leaves a great deal of freedom, but on the other hand, the area that is/was therapeutically effectively covered cannot be made visible to the operator for checking, which may then, as in the present example of FIG. 2, result in an insufficient placement in the sense of a patchy or incomplete irradiation. As shown in the example of FIGS. 1 and 2, it is advantageous here that the penetration depth of the light is relatively large, i.e. the light spheres 21 are relatively large, so that only a relatively small number of light applicators 9 are required here to completely irradiate the organ 3.

Figure 3:
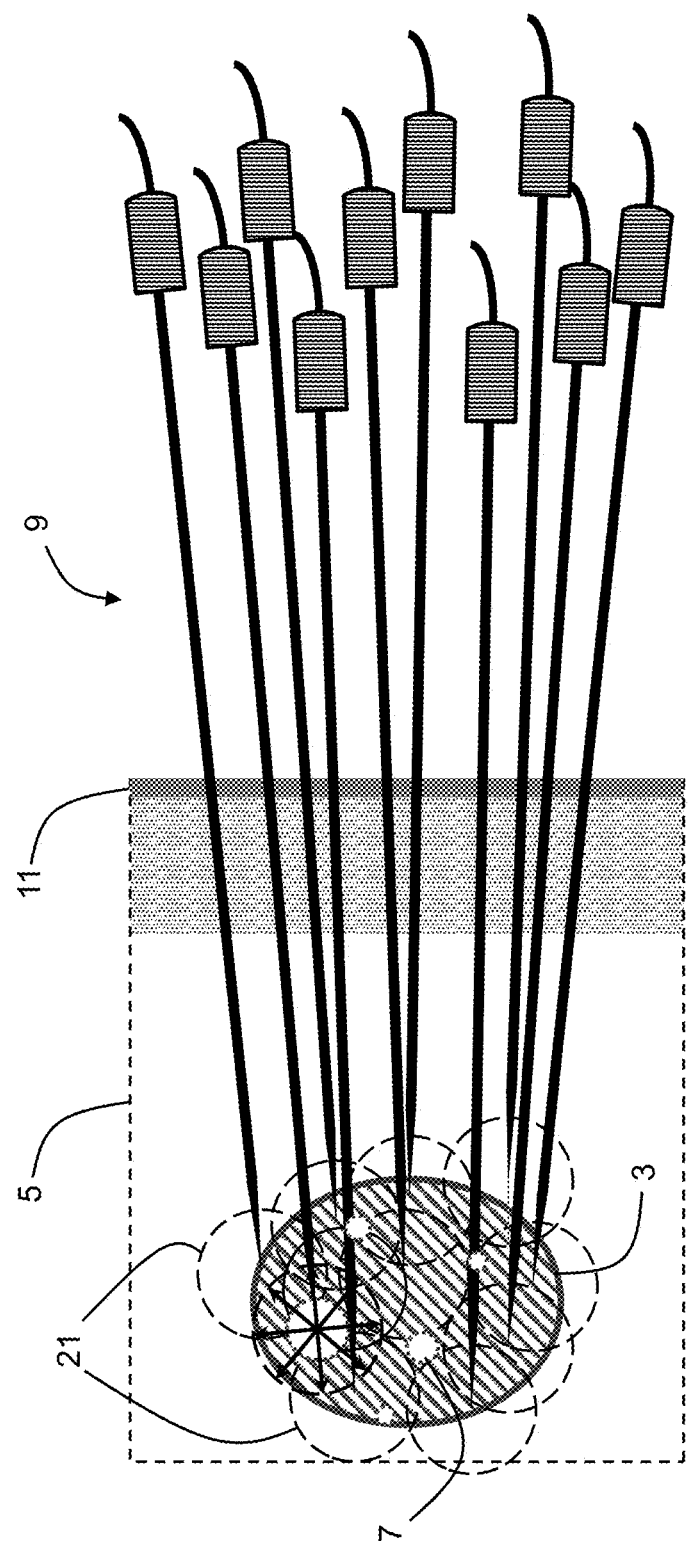
FIG. 3 is a schematic representation of the primary mode of operation of a percutaneous PDT with a plurality of light applicators with a relatively low penetration depth of the light.

In contrast to the preceding examples, however, in FIG. 3 the penetration depth of the light is relatively small, i.e. the light spheres 21 are relatively small, so that here relatively many light applicators 9 are needed to irradiate the organ 3 completely. This makes the situation with regard to correct placement of the light applicators 9 or their applicator tips 19 correspondingly more complex for the operator compared to that in FIG. 1 and FIG. 2, which ultimately leads to a further increase in the likelihood that certain tissue areas of the organ 3 remain unirradiated and therefore a pathological tissue area 7 remains untreated (e.g. centre-left in FIG. 3).

Figure 4:
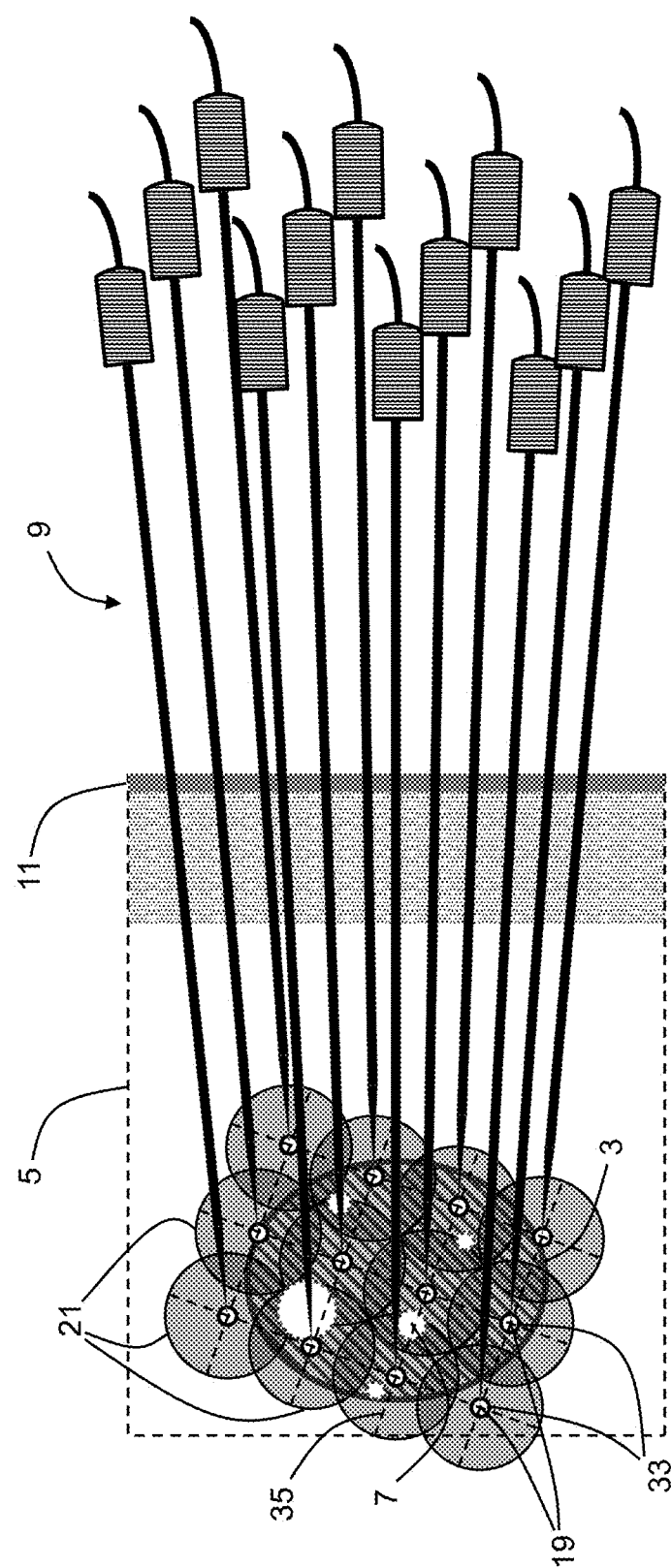
FIG. 4 is a schematic representation of a distribution, which is desired in principle, of a plurality of light applicators for percutaneous PDT.

In FIG. 4 it is shown that it would therefore make sense, i.e. based on the previously gained knowledge, to place the applicator tips 19 at all virtual target points 33 of a virtual three-dimensional target point grid structure 35. The target point grid structure 35 is adapted to the shape and position of the organ 3 as well as the penetration depth of the light in the organ 3. The target point grid structure 35 is therefore organ-specific. The distances between the virtual target points 33 are adapted to the organ 3 such that, on the one hand, the light spheres 21 overlap gap-free and the entire organ 3 is irradiated gap-free, but such that, on the other hand, this overlapping is preferably advanced only as far as necessary in the sense of a patient-friendly procedure, i.e. such that unnecessarily small distances of the light-emitting applicator tips 19 are avoided in order to thereby minimise the number of light applicators 9 or light applicator piercing operations. These two opposing requirements result in a target point grid structure 35 in which the position and, above all, the distances of the virtual target points 33 relative to each other are quite precisely defined and have relatively narrow tolerances.

Figure 5:
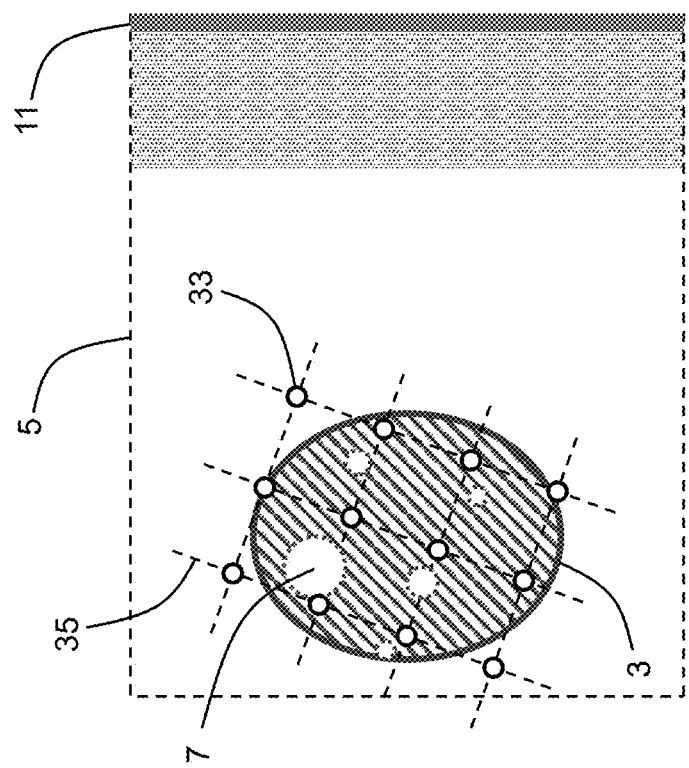
FIG. 5 is a schematic representation of a virtual organ-specific target point grid structure for the applicator tips in the organ or organ segment.

The difficulty now is to place the applicator tips 19 exactly at these virtual target points 33, since the virtual three-dimensional target point grid structure 35 is not visible to the operator and thus the virtual target points 33 cannot be steered towards in a targeted manner directly by the operator with the light-emitting applicator tips 19. For the sake of clarity, this virtual target point grid structure 35 with its virtual target points 33 and their position in relation to the organ 3 to be treated is shown separately again in FIG. 5, i.e. without the applicators 9 and without the light spheres 21 generated by their applicator tips 19.

Figure 6:
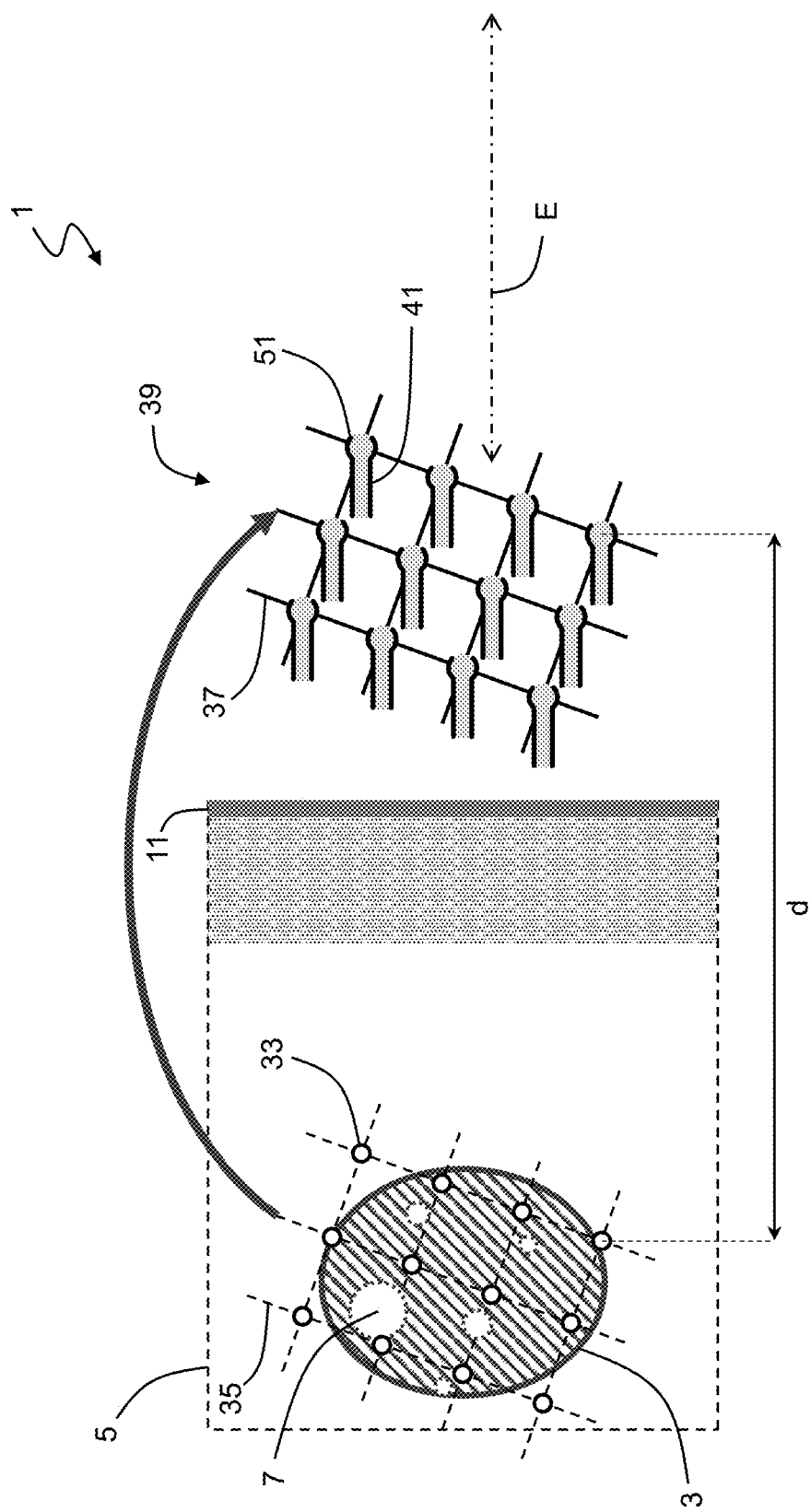
FIG. 6 is a schematic representation of a fixing point grid structure parallel-displaced relative to the virtual organ-specific target point grid structure of FIG. 5.
Figure 7:
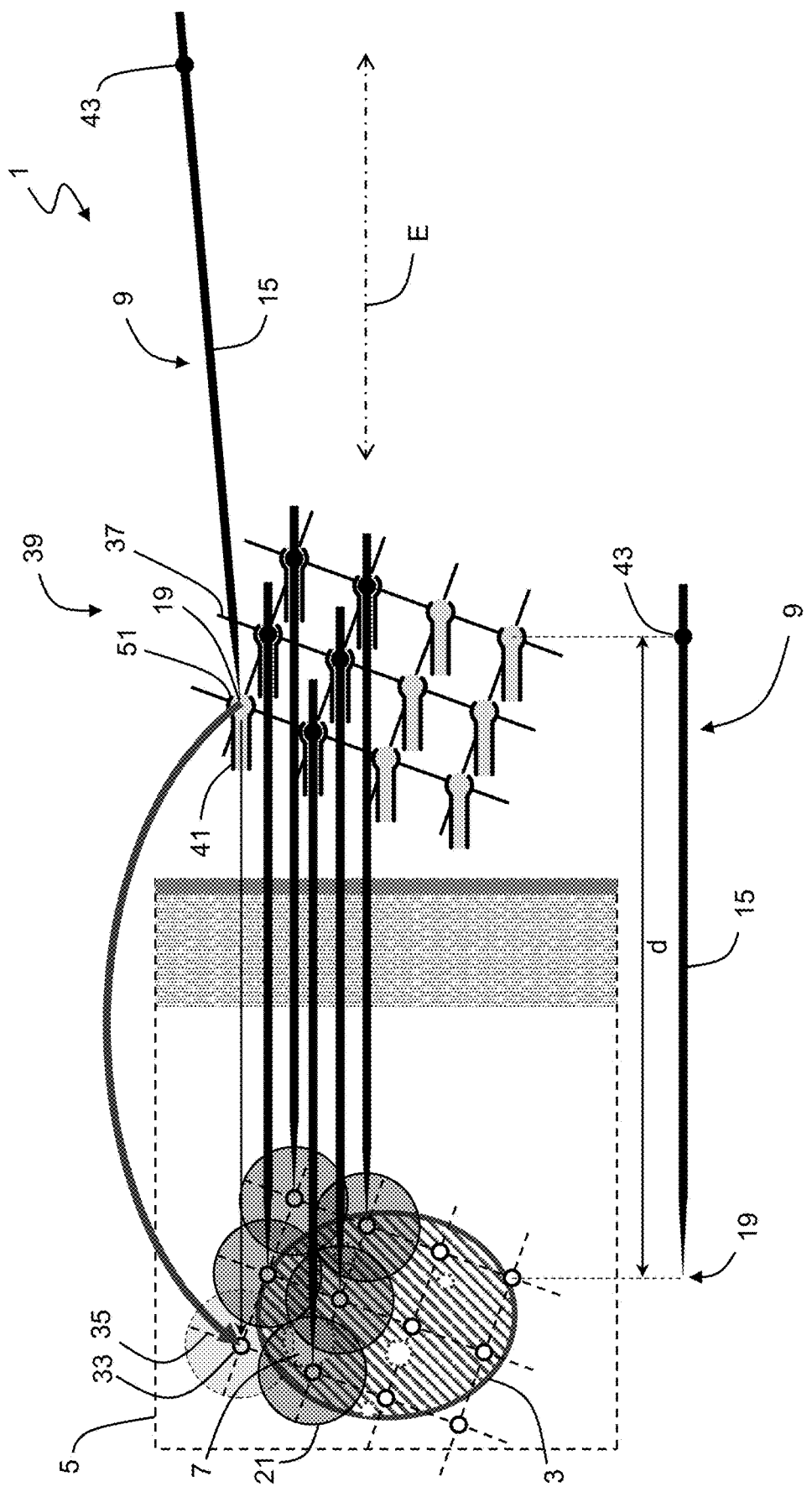
FIG. 7 is a schematic representation of an exemplary embodiment of a system disclosed herein for performing transcutaneous PDT.

FIGS. 6 and 7 now illustrate the procedure according to the invention for solving the problem described above, i.e. the precise placement of the light-emitting applicator tips 19 in the virtual and invisible target points 33, said procedure consisting of two steps.

In a first step, which is shown in FIG. 6, the virtual and invisible target point grid structure 35 with its virtual and invisible target points 33 is mapped from the inside of the body 5 onto a fixing point grid structure 37 outside the body 5, the fixing point grid structure being formed by a real and visible placement template 39 with real and visible fixing point receptacles 51, which can thus also be steered towards in a targeted manner and directly by the operator with the light-emitting applicator tips 19. This mapping of the target point grid structure 35 onto the fixing point grid structure 37 is a parallel displacement or translation by a defined length d, which is defined by the distance of the organ 3 to the space outside the body where the placement template 39 is to be positioned, parallel to an axis E, the direction of which is defined by the piercing axis of the applicators 9 (in this regard see also FIG. 7). This specific form of the mapping performed here, i.e. the parallel displacement of the target point grid structure 35 or of the target points 33 with their two characterising parameters, i.e. displacement length d and displacement direction E, is intended to be illustrated again schematically and explicitly in FIG. 6 by the thick arcuate arrow pointing to the right. The axis E is preferably but not necessarily orthogonal to the skin 11.

Only in a second step, which is shown in FIG. 7, is the actual, therapy-preparing applicator placement carried out, in that the light-emitting applicator tips 19 are first guided to the fixing point receptacles 51 of the placement template 39, which are real and visible and thus can be steered towards in a targeted manner and directly, in order to be "mapped" or moved from there in a defined, unambiguous and thus reliable manner into or to the virtual target points 33, which are invisible to the operator. This second mapping, which is to be carried out within the scope of the two-stage procedure, i.e. the parallel displacement of the light-emitting applicator tips 19 from outside the body 5 into the body 5, is now characterised in accordance with the procedure according to the invention specifically by the fact that it is inverse to the first mapping shown in FIG. 6, i.e. to the parallel displacement of the target point grid structure 35 from inside the body 5 to outside. Specifically, this means that the applicator tips 19—starting from the fixing point receptacles 51 and thus starting from the target points of the first mapping or parallel displacement—are moved by the same defined length d and parallel to the same axis E, but exactly against the first parallel displacement. This specific form of the second mapping carried out here, i.e. the parallel displacement with its two characterising parameters, i.e. displacement length d and displacement direction E, is intended to be illustrated again schematically and explicitly in FIG. 7 by the thick arcuate arrow pointing left.

In this context, the definiteness, unambiguity and reliability with regard to the accuracy of the placement of the light-emitting applicator tips 19 in the target points 33 in the organ 3, i.e. the features that are decisive here with regard to the required gap-free irradiation of the organ 3, when introducing the light-emitting applicator tips 19 from the fixing point receptacles 51 outside the body 5 to the virtual target points 33 inside the body 5—despite the invisibility of the target points 33 for the operator and the resulting impossibility of being able to steer towards them in a targeted manner—are achieved by the fact that the degrees of freedom for the operator when moving the light applicators 9 or in the placement of the light-emitting applicator tips 19 in the body 5 are reduced to a minimum, i.e. by the fact that there is no possibility of movement other than the required parallel displacement of the light-emitting applicator tips 19, which is exactly inverse to the first parallel displacement of the target point grid structure 35.

Guiding the movement of the light-emitting applicator tips 19 into the body 5 exclusively in accordance with the inverse parallel displacement is achieved firstly by the fact that the placement template 39, in addition to the aforementioned fixing point receptacles 51, is additionally provided with guides 41 which have a defined orientation, specifically an orientation parallel to the axis E, as a result of which only a single direction of movement, namely the direction of movement of the light applicators 9 with their applicator tips 19 defined for the target inverse parallel displacement, parallel to the axis E, is permitted or possible, and secondly by the fact that the light applicators 9 are all provided with at least one fixing point 43, which has a defined distance d from the light-emitting applicator tip 19, which specifically corresponds precisely to the displacement length d of the target point grid structure 35 for the first mapping or parallel displacement, and which can be fixed in or on the fixing point receptacles 51 of the placement template 39, whereby only a single penetration depth of the associated light-emitting applicator tip 19 into the body 5 and into the organ 3, said penetration depth specifically being the penetration depth defined for the desired inverse parallel displacement, is permitted or possible.

Both together lead to the fact that, with a movement of the light applicators 9 in the distal direction up to the stop in the placement template 39—starting from the visible fixing point receptacles 51, which therefore can be steered towards directly—the light emitting applicator tips 19 also all automatically arrive at the target points 33, and thus the desired gap-free irradiation of the organ 3 is also automatically ensured, provided that also all fixing point receptacles 51 of the template 39 are populated with light applicators 9 and activated.

Figure 8:
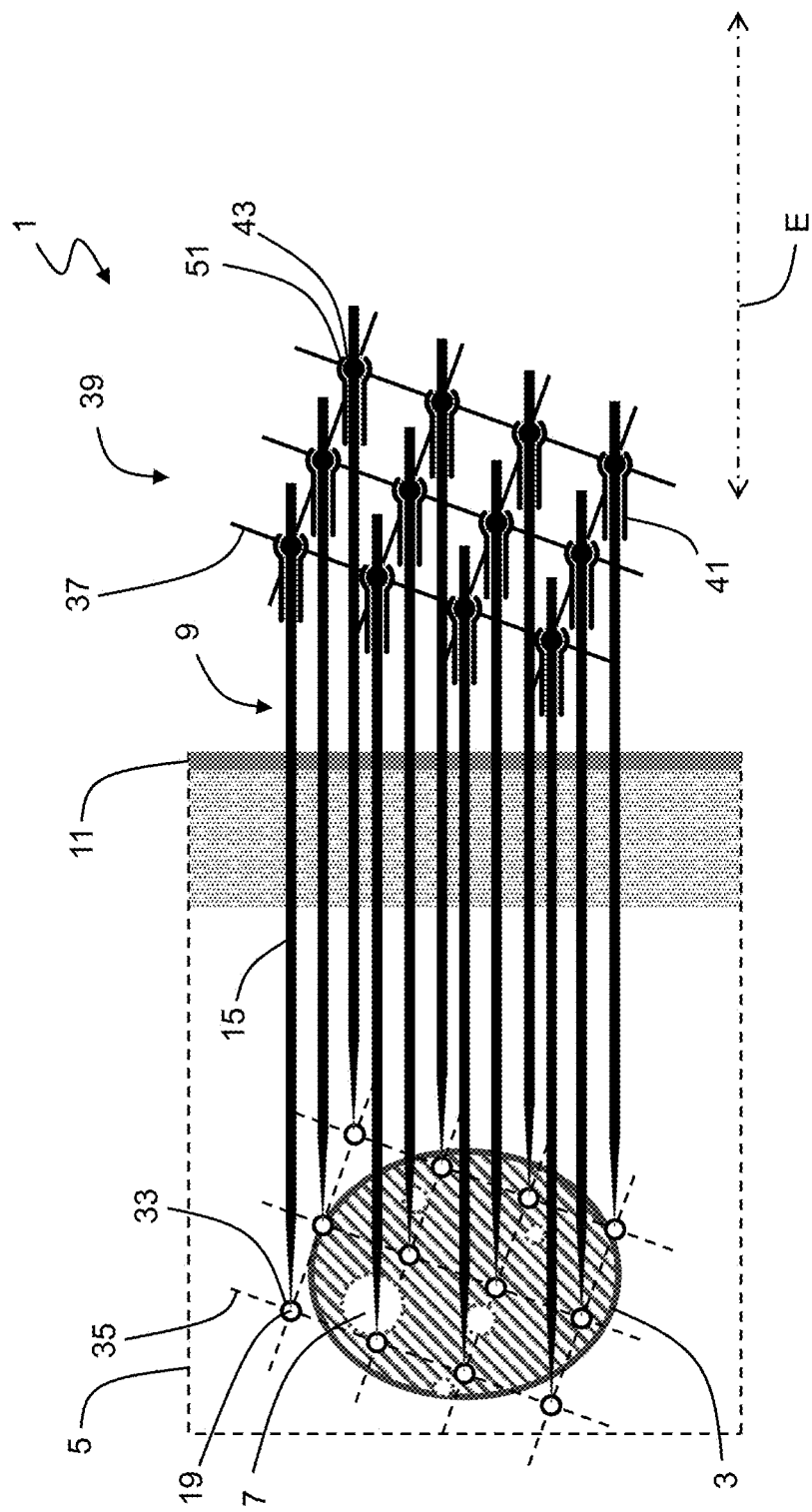
FIG. 8 is a schematic representation of the system shown in FIG. 7 with all light applicators in the pierced position for PDT.

The operator therefore only has to bring the light applicators 9 up to the fixing point receptacles 51, then pass them through the guides 41 and transcutaneously pierce the organ 3 until the fixing point 43 is located at the grid point of the fixing point grid structure 37, i.e. at the fixing point receptacle 51. Then, the applicator tip 19 is also automatically placed at the associated target point 33. In contrast to the procedure described in FIGS. 2 and 3, the operator has no or only a few degrees of freedom and does not need a great deal of experience. In addition, the placement can be carried out quickly with just as many piercing operations as necessary, but with as few piercing operations as possible. PDT can be performed at the same time as all the light applicators 9 are placed, allowing for a short treatment time. This is shown in FIG. 8. For the sake of clarity, the light spheres 21 are not shown there, and so FIG. 8 shows the situation immediately before or immediately after the irradiation.

The inventive procedure is therefore based firstly on the performance of two mapping operations, namely on the one hand the mapping of the target points 33 on the fixing point receptacles 51 of the placement template 39 and on the other hand the mapping of the light-emitting applicator tips 19 starting from the fixing point receptacles 51 back to the target points 33, wherein the second mapping is characterised accordingly by the fact that it is inverse to the first mapping, and secondly by the fact that it is ensured by mechanical construction that the second mapping, which corresponds to the actual applicator placement by the operator, is without alternative, i.e. a movement of the applicators 9 or of the applicator tips 19 deviating from the second mapping—starting from the fixing points or fixing point receptacles 51 into the body 5 and into the organ 3—is not at all possible.

As the size of the organ 3 increases, the number of light applicators 9 required increases greatly. For example, doubling the diameter of a spherical organ 3 means that eight times as many light applicators 9 are required. If, in addition, on the one hand the penetration depth of the light is comparatively small and on the other hand the extent of the organ 3 along the piercing axis E is comparatively large, then the density of the light applicators 9 in the planes perpendicular to the piercing axis E is correspondingly high and it may be that the light applicators 9 no longer find sufficient space next to each other. This becomes clear in FIGS. 7 and 8, where the procedure described above almost reaches its limits in this respect, especially if a manual handle is also taken into account for the light applicators 9, said handle not being shown at all in FIGS. 7 and 8.

Figure 9:
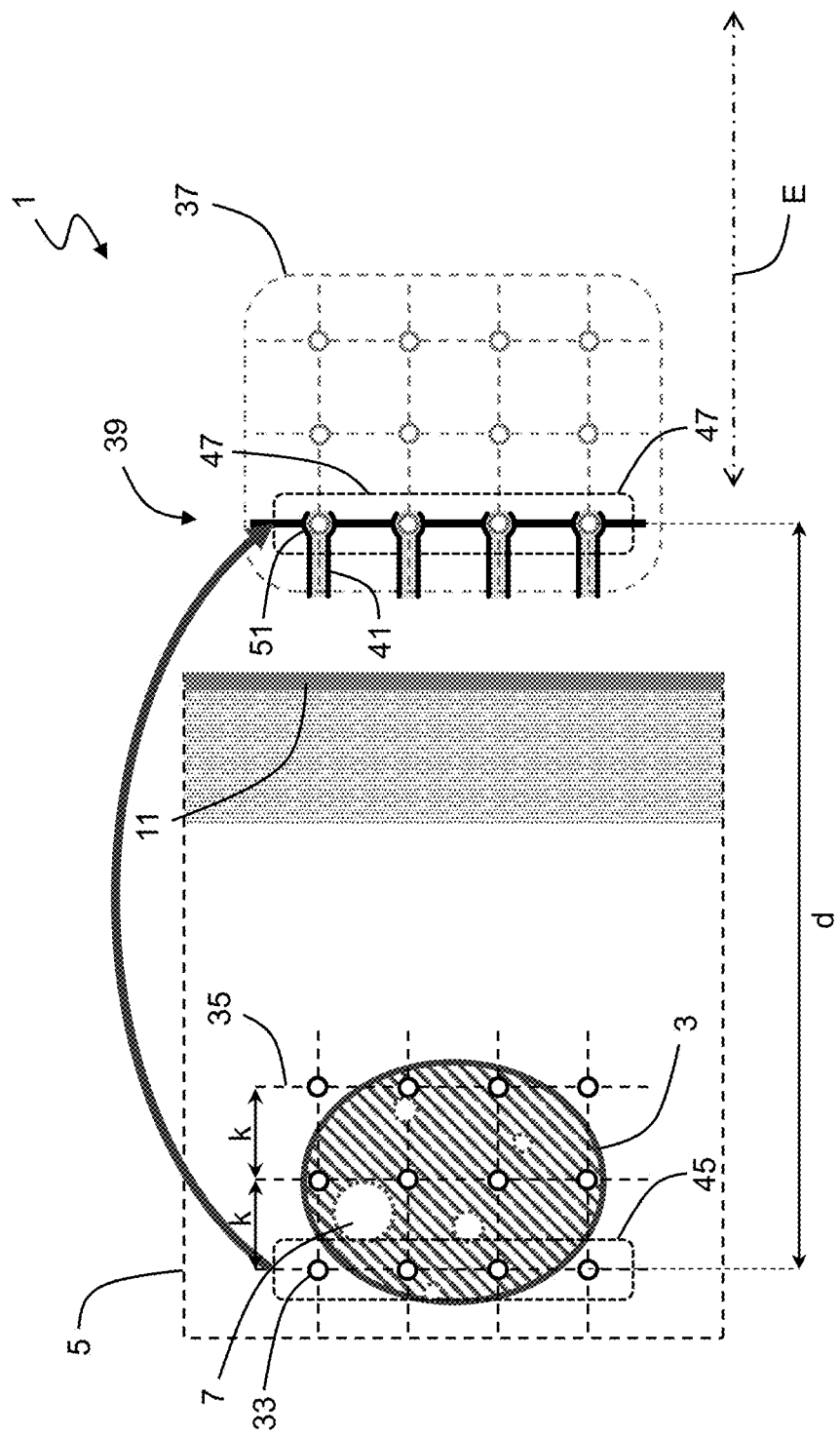
FIG. 9 is a schematic illustration of another exemplary embodiment of a system disclosed herein for performing transcutaneous PDT successively, target point grid area by target point grid area.
Figure 10:
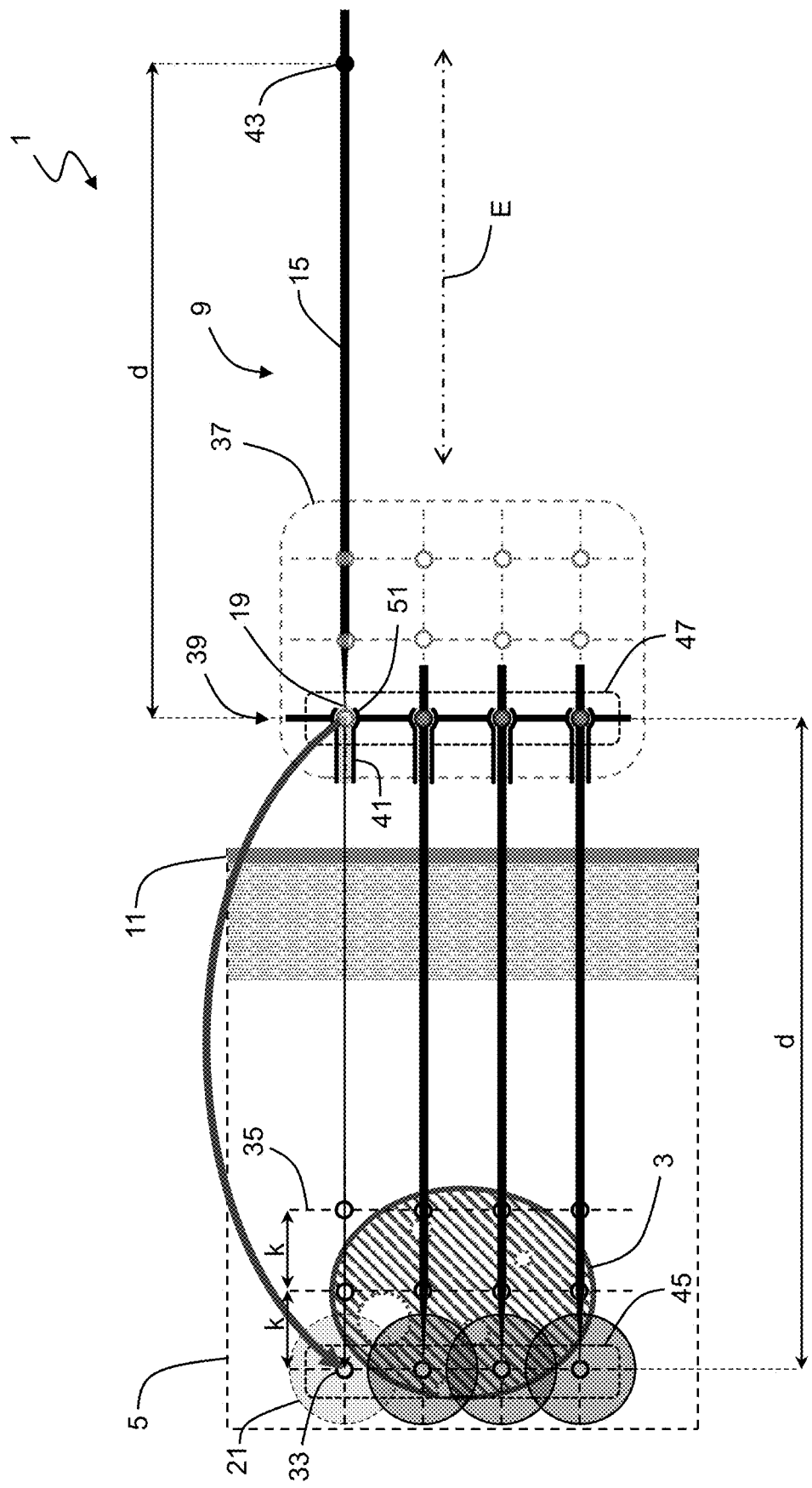
FIG. 10 is a schematic representation of the system with light applicators for PDT shown in FIG. 9.

This problem can be solved by performing a step-by-step PDT. FIGS. 9 and 10 show how the PDT can be performed step by step in target point grid areas 45 of the target point grid structure 35. For this purpose, the fixing points 43 of the light applicators 9 are placed or fixed at the grid points or the fixing point receptacles 51 of an associated fixing point grid area 47 of the fixing point grid structure 37, so that the applicator tips 19 are placed at the associated target points 33 of the target point grid area 45. PDT is first performed for the first target point grid area 45, which is preferably the target point grid area 45 located deepest under the skin, i.e. furthest away distally. Then the light applicators 9 can be retracted proximally by a distance k of the target point grid areas 45 in order to perform the PDT for the second target point grid area 45. This is carried out step by step for all target point grid areas 45 until the entire volume of the organ 3 has been irradiated with light. The advantage of this procedure is that fewer light applicators 9 and fewer piercing operations are required than in the exemplary embodiment shown in FIG. 8. In addition, all the light applicators 9 can generally be inserted in this way and are not in each other's way. However, the treatment time is longer, as the PDT is carried out step by step or successively at each target point grid area 45 and not in one step or not simultaneously for the entire organ 3.

In addition, FIGS. 9 and 10 once again explicitly show in the two-stage procedure according to the invention for solving the problem that the operator must, on the one hand, place the light-emitting applicator tips 19 precisely at the target points 33 for gap-free irradiation of the organ 3, but, on the other hand, cannot in any way steer towards these target points 33 directly in a targeted manner because they are merely virtual and accordingly invisible points within the interior of the body and organ, which in any case cannot be seen at all.

In a first step of the two-step procedure shown in FIG. 9, a virtual and invisible target point grid area 45 of the virtual and invisible target point grid structure 35 with its target points 33 from the inside of the body 5 is mapped onto a corresponding fixing point grid area 47 of the fixing point grid structure 37 outside the body 5, which is formed by a real and visible placement template 39 with real and visible fixing point receptacles 51, which can thus also be steered towards in a targeted manner and directly by the operator with the light-emitting applicator tips 19. This mapping of the target point grid area 45 onto the fixing point grid area 47, as with the procedure already explained in FIG. 6, is a parallel displacement or translation by a defined length d, which is defined by the distance of the organ 3 to the space outside the body 5, where the placement template 39 is to be positioned, parallel to an axis E, the direction of which is defined by the piercing axis of the applicators 9 (see also FIG. 10). This specific form of the mapping carried out here, i.e. the parallel displacement of the target point grid area 45 with its two characterising parameters, i.e. displacement length d and displacement direction E, is intended to be illustrated again in FIG. 9 explicitly and schematically by the thick arcuate arrow pointing right.

In the second step of the two-step procedure, which is shown in FIG. 10, the actual, therapy-preparing applicator placement is carried out by first guiding the light-emitting applicator tips 19 to the fixing point receptacles 51 of the fixing point grid area 47 of the placement template 39, said fixing point receptacles being real and visible and it thus being possible to steer towards them in a targeted manner and directly, in order to be "mapped" or moved from there in a defined, unambiguous and thus reliable manner into or to the virtual target points 33, which are invisible to the operator. This second mathematical mapping to be carried out within the scope of the two-step procedure, i.e. the parallel displacement of the light-emitting applicator tips 19 from outside the body 5 into the body 5, is now characterised in accordance with the procedure according to the invention precisely by the fact that it is inverse to the first mathematical mapping shown in FIG. 9 in the form of a parallel displacement of the target point grid area 45 from inside the body 5 to outside. Specifically, this means that the applicator tips 19—starting from the fixing point receptacles 51 and thus starting from the target points of the first parallel displacement—are moved by the same defined length d and parallel to the same axis E, but exactly against the first parallel displacement. This specific form of the second mapping carried out here, i.e. the parallel displacement with its two characterising parameters, i.e. displacement length d and displacement direction E, is intended to be illustrated again explicitly and schematically in FIG. 10 by the thick, arcuate arrow pointing left.

In this context, the definiteness, unambiguity and reliability with regard to the accuracy of the placement of the light-emitting applicator tips 19 in the target points 33 in the organ 3, i.e. the features that are decisive here with regard to the required gap-free irradiation of the organ 3, when introducing the light-emitting applicator tips 19 from the fixing point receptacles 51 outside the body 5 to the virtual target points 33 inside the body 5—despite the invisibility of the target points 33 for the operator and the resulting impossibility of being able to steer towards them in a targeted manner—are achieved by the fact that the degrees of freedom for the operator when moving the light applicators 9 or in the placement of the light-emitting applicator tips 19 in the body 5 are reduced to a minimum, i.e. by the fact that there is no alternative to the necessary parallel displacement of the light-emitting applicator tips 19, which is inverse to the first parallel displacement of the target point grid area 45.

The latter is achieved firstly by the fact that the placement template 39, in addition to the aforementioned fixing point receptacles 51, is additionally provided with guides 41 which have a defined orientation, specifically an orientation parallel to the axis E, as a result of which only a single direction of movement, namely the direction of movement of the light applicators 9 with their applicator tips 19 defined for the desired inverse parallel displacement, parallel to the axis E, is permitted or possible, and secondly by the fact that the light applicators 9 are all provided with at least one fixing point 43, which has a defined distance d from the light-emitting applicator tip 19, which specifically corresponds precisely to the displacement length d of the target point grid structure 45 for the first mapping or parallel displacement, and which can be fixed in or on the fixing point receptacles 51 of the placement template 39, whereby only a single penetration depth of the associated light-emitting applicator tip 19 into the body 5 and into the organ 3, said penetration depth specifically being the penetration depth defined for the desired inverse parallel displacement, is permitted or possible.

Both together lead to the fact that, with a movement of the light applicators 9 in the distal direction up to the stop in the placement template 39—starting from the visible fixing point receptacles 51, which therefore can be steered towards directly—the light emitting applicator tips 19 also all automatically arrive at the target points 33, and thus the desired gap-free irradiation of the organ 3 is also automatically ensured, provided that also all fixing point receptacles 51 of the template 39 are populated with light applicators 9 and activated.

Figure 11:
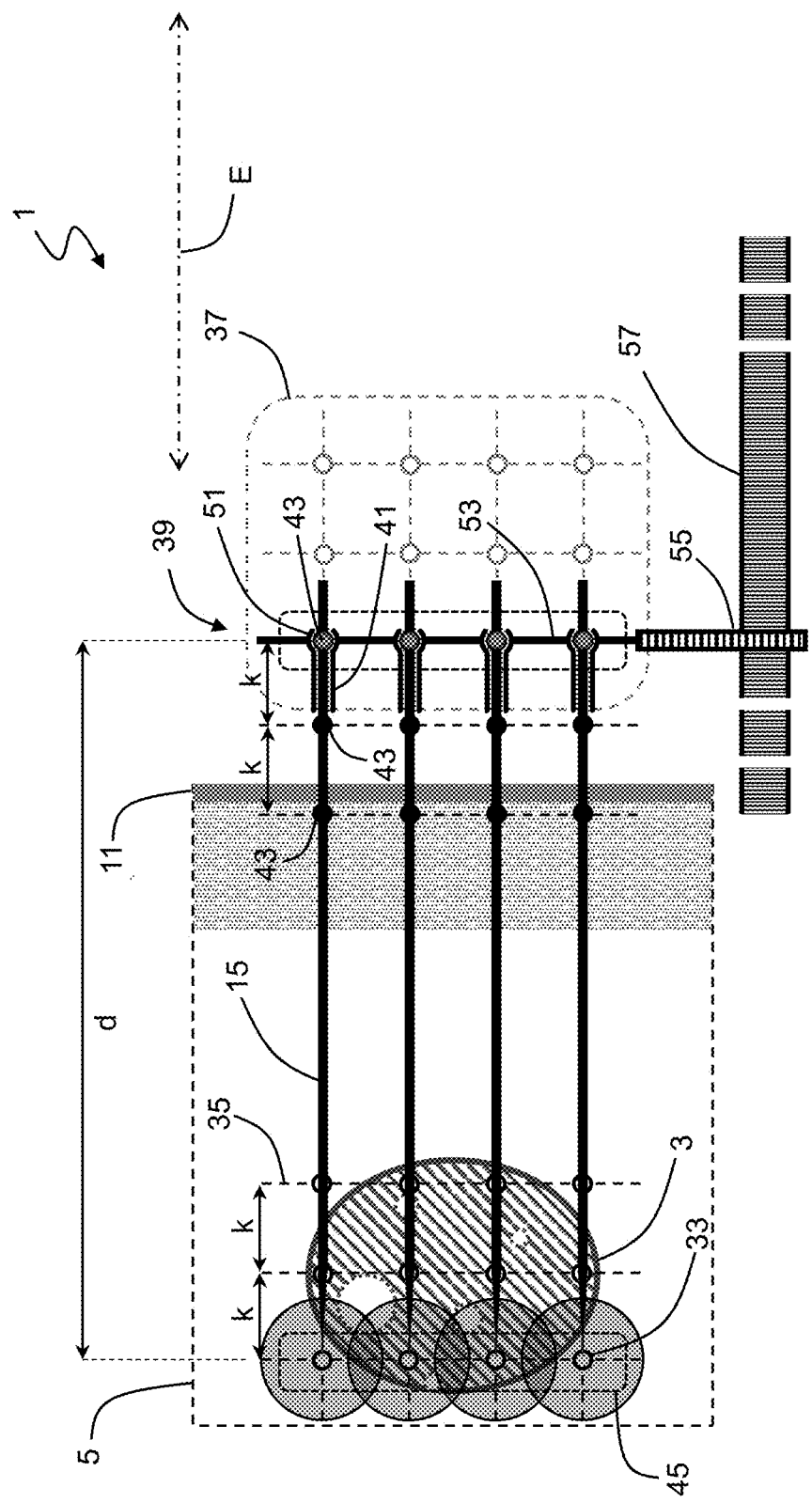
FIG. 11 is a schematic illustration of another exemplary embodiment of a system disclosed herein for performing transcutaneous PDT with applicator tips in a first target point grid area.
Figure 12:
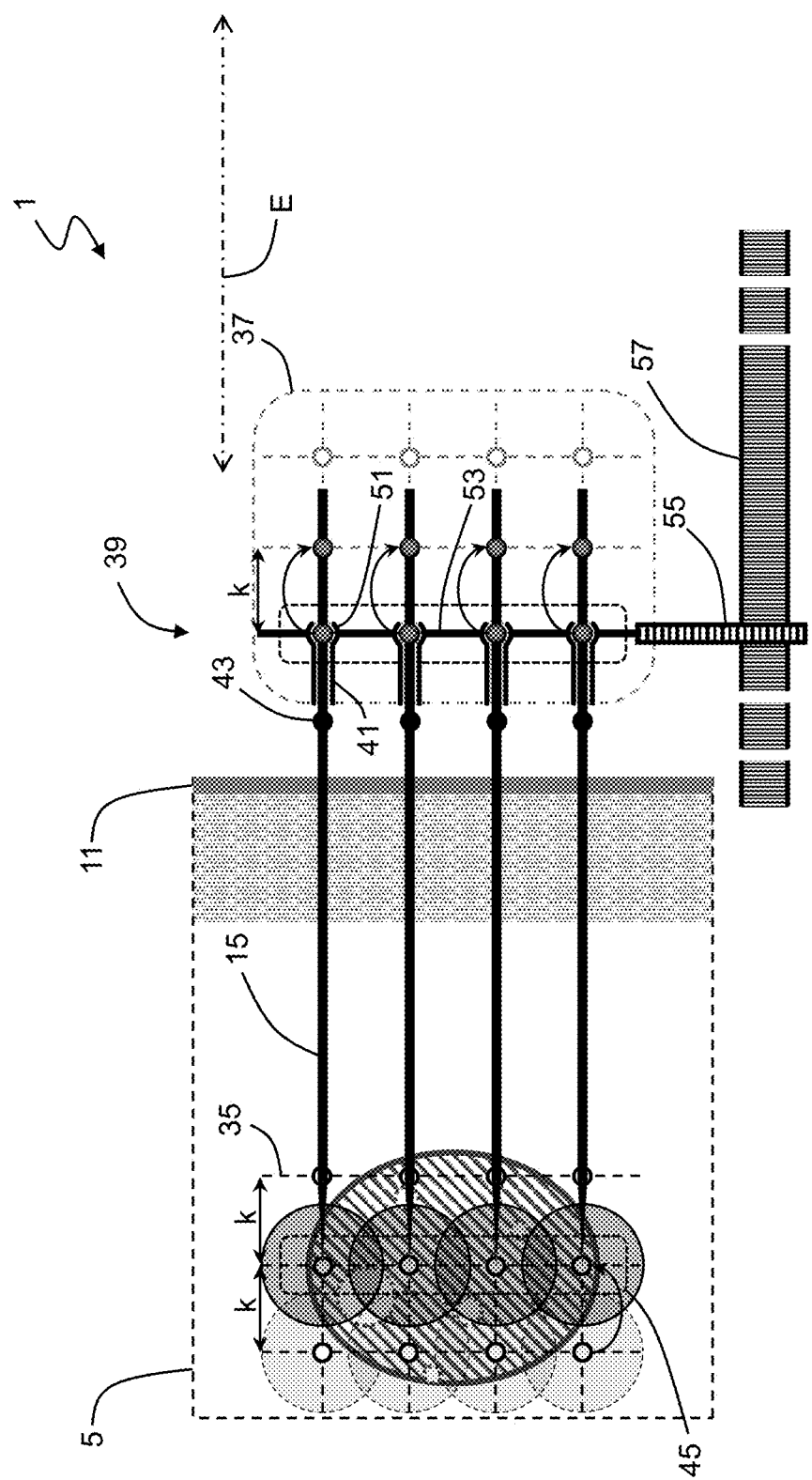
FIG. 12 is a schematic representation of the system shown in FIG. 11 with applicator tips in a second target point grid area.
Figure 13:
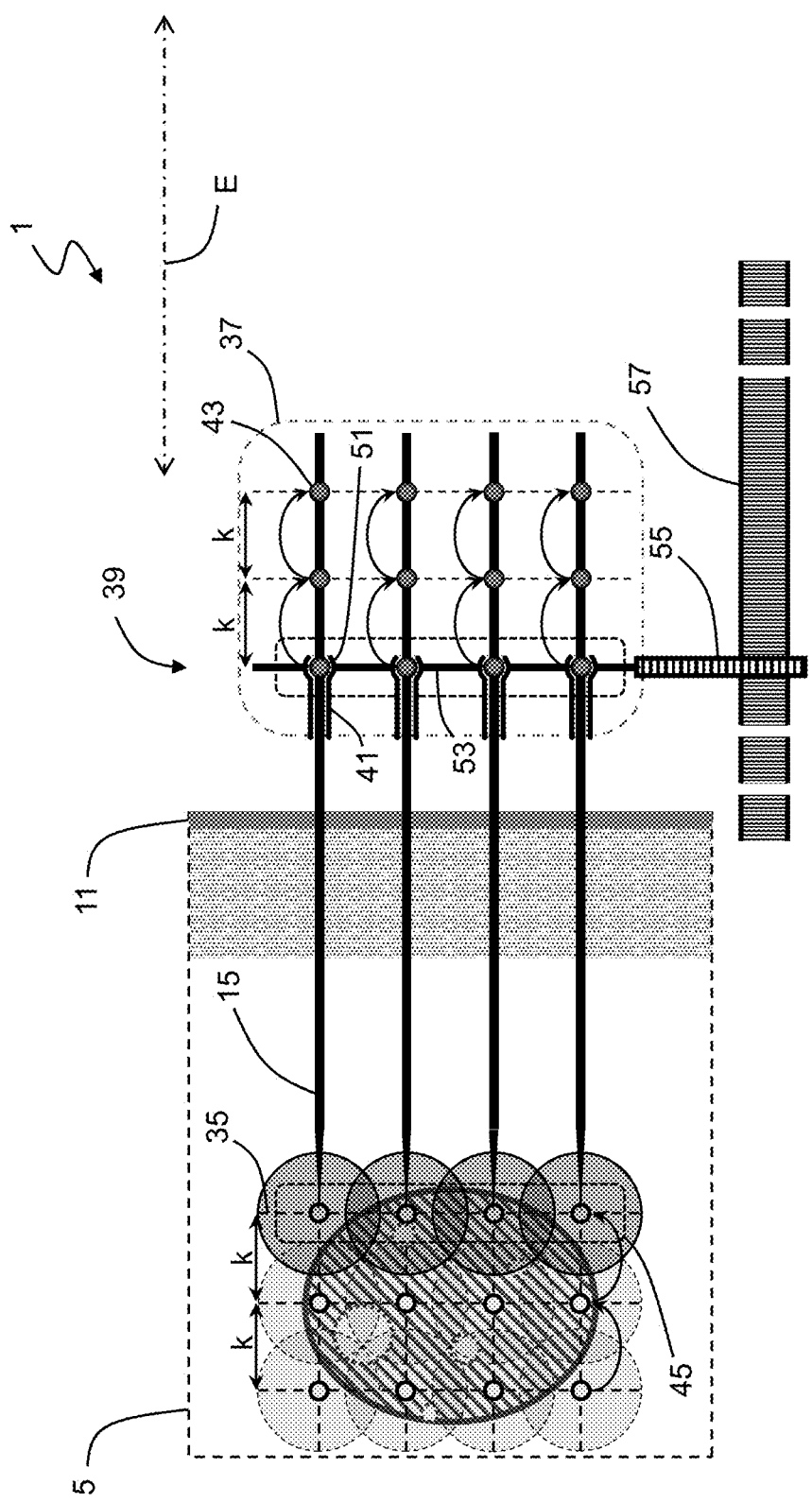
FIG. 13 is a schematic representation of the system shown in FIGS. 11 and 12 with applicator tips in a third target point grid area.

FIGS. 11 to 16 show various implementation options for step-by-step PDT in target point grid areas 45. In FIGS. 11 to 13, the light applicators 9 each have a plurality of fixing points 43 arranged at a distance k, so that the operator can select the fixing point 43 that is placed at the corresponding grid point of the fixing point grid structure 37 or at the corresponding fixing point receptacle 51 of the placement template 39 in order to determine the target point grid areas 45 in which the applicator tip 19 is to lie. The three-dimensional fixing point grid structure 37 is thus defined here on the one hand by stationary fixing point receptacles 51, which lie on a fixing point receptacle grid area 53, and on the other hand by the fixing points 43 of the light applicators 9 arranged at a distance k, wherein this three-dimensional fixing point grid structure 37 is built up step by step in the procedure shown here and reaches its final shape and size only after all fixing points 43 of each light applicator 9 have passed step by step through the associated fixing point receptacle 53 of the placement template 39, which has been achieved ultimately in the state of FIG. 13. The fixing point receptacles 51 of the fixing point receptacle grid area 53 are arranged here in or on the guides 41 of the placement template 39. The placement template 39 has a fastening device 55 with which the placement template 39 can be fixed relative to a fixed reference surface 57, for example a treatment table, in a position and/or orientation set by the operator. The patient's body 5 is also fixed here relative to the fixed reference surface 57, for example a treatment table. After the PDT with the applicator tips 19 in the first target point grid area 45 according to FIG. 11, in FIG. 12 the organ 3 is irradiated with the applicator tips 19 in the second target point grid area 45. In FIG. 13, the organ 3 is then irradiated with the applicator tips 19 in the third and last target point grid area 45.

Figure 14:
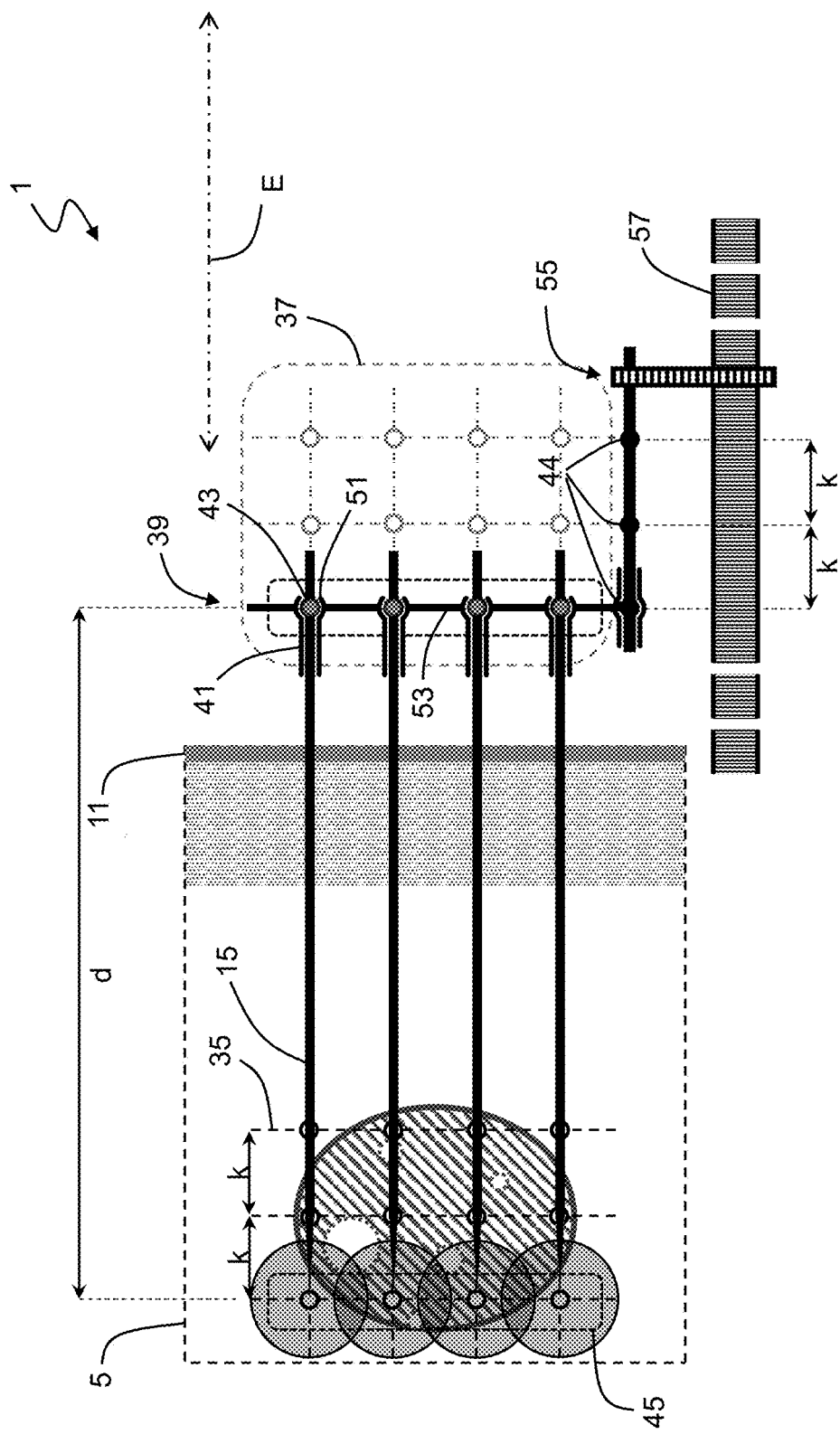
FIG. 14 is a schematic illustration of another exemplary embodiment of a system disclosed herein for performing transcutaneous PDT with applicator tips in a first target point grid area.

In FIG. 14, the light applicators 9 do not each have a plurality of fixing points 43 arranged at a distance k, and instead the placement template 39 can be moved as a whole by the distance k in a defined manner relative to the fixed reference surface 57. For this purpose, the placement template 39 defines a plurality of fixing points 44 arranged at a distance k by means of the fastening device 55, in order to be able to displace the fixing point receptacle grid area 53 as a whole by the distance k in a defined manner. This has the advantage that the light applicators 9 do not have to be moved individually when changing to the next target point grid area 45, but are moved together in a concerted manner. This accelerates and simplifies the treatment process. After the PDT with the applicator tips 19 in the first target point grid area 45 according to FIG. 14, in FIG. 15 the organ 3 is irradiated with the applicator tips 19 in the second target point grid area 45. In FIG. 16, the organ 3 is then irradiated with the applicator tips 19 in the third and last target point grid area 45. For the sake of clarity, the fixing point grid structure 37 is no longer drawn in FIGS. 15 and 16.

Figure 17:
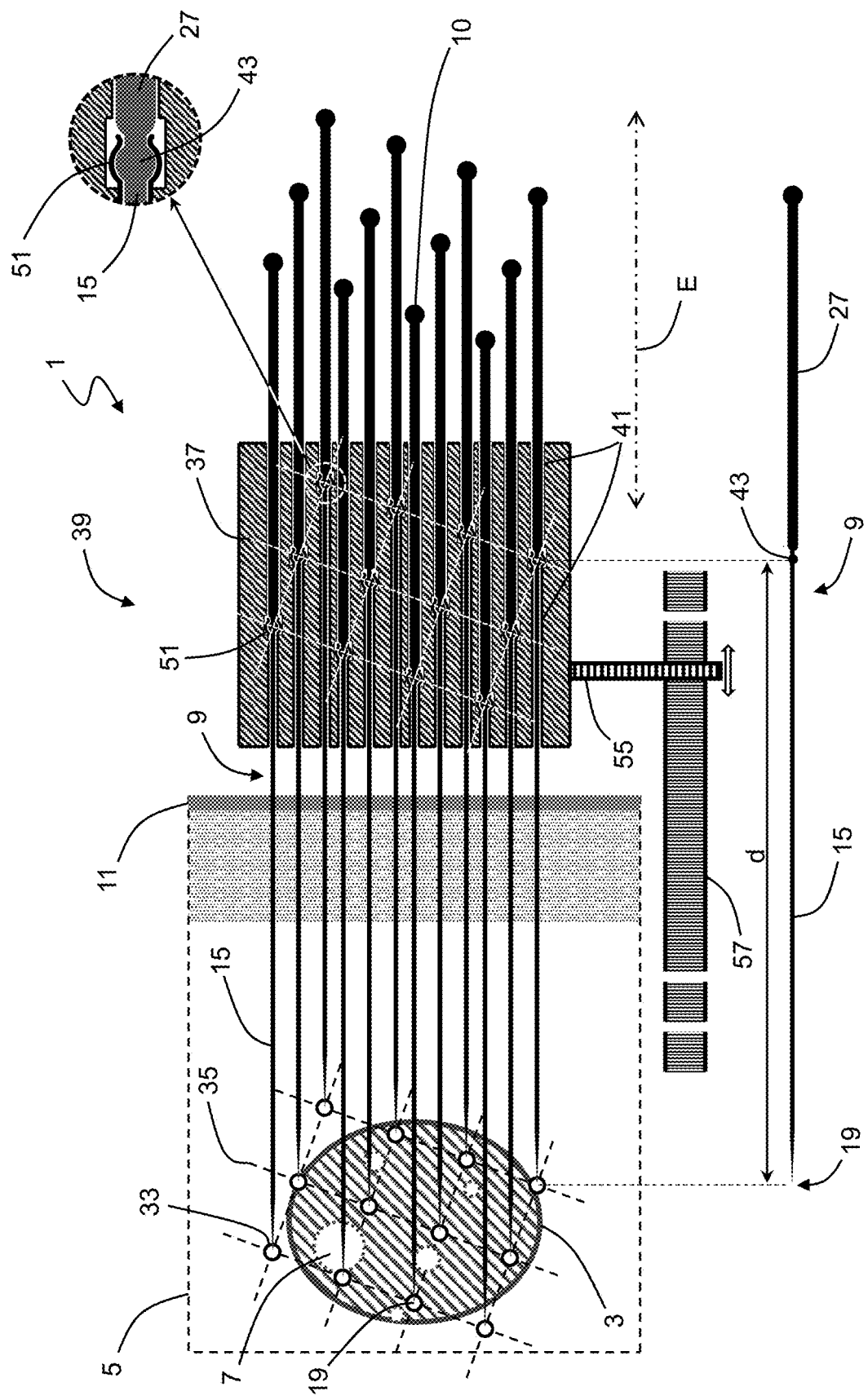
FIG. 17 is a schematic representation of another exemplary embodiment of a system disclosed herein for performing transcutaneous PDT with all light applicators in the pierced position.

FIG. 17 shows an exemplary embodiment of the principle shown in FIG. 8. The placement template 39 is here a block or differently formed body with a certain thickness along the piercing axis E, through which a plurality of guides 41 arranged parallel to each other run along the piercing axis E. Each guide 41 has a fixing point receptacle 51 which forms a grid point of the fixing point grid structure 37. The three-dimensional fixing point grid structure 37 formed in this way is identical to the organ-specific virtual target point grid structure 35 for the applicator tips 19 and is created from the latter by means of a parallel displacement or translation by the length d. Each light applicator 9 has a thin insertion portion 15 and a thicker proximal portion that serves as a grip element 27 and for guidance in the guides 41. The fixing point 43 is formed here by a spherical stop arranged at the proximal end of the insertion portion 15. The guides 41 are dimensioned to match the diameter of the insertion portion 15 and of the thicker proximal portion of the light applicators 9. The light applicators 9 are preferably all identical to avoid the risk of incorrect selection of a "wrong" light applicator 9 and consequent incorrect positioning of the light-emitting applicator tip 19 in the organ 3. In this exemplary embodiment, the operator has no degrees of freedom, and can only insert the light applicators 9 in one way until the fixing points 43 engage in the fixing point receptacles 51. For this purpose, the fixing point receptacles 51 here have jaw clamps or some other clamping means. This gives the operator haptic feedback regarding correct placement and prevents unintentional proximal slippage of the light applicators 9. The placement template 39 is movable in a guided manner along the piercing axis E by means of its fastening device 55 and can be fixed relative to the reference surface 57. The position of the placement template 39 in this respect can preferably be determined as follows. The placement template 39 is first placed and fixed with the fastening device 55 at the reference surface 57 very close to the body 5 or to the skin 11. Then, preferably, a first light applicator 10 to be positioned centrally with respect to a plane perpendicular to the piercing axis E and distally with respect to the piercing axis E itself is inserted and advanced—controlled by an imaging process (for example ultrasound sonography)—until its applicator tip 19 has reached the distal region of the organ 3, as shown for example in FIG. 17. Then—while maintaining this reached position of the first light applicator 10 or its applicator tip 19—the placement template 39 is retracted axially, i.e. along the piercing axis E, away from the skin 11 in the proximal direction by means of the fastening device 55 on the reference surface 57 until the fixing point 43 can be fixed in the fixing point receptacle 51, i.e. in the case shown here engages in the jaw clamp. In this position, the placement template 39 is then fixed to the reference surface 57 by means of the fastening device 55.

With this process, the defined distance d between the virtual target point grid structure 35 and fixing point grid structure 37 is established. This process thus completes the first step of the procedure according to the invention, namely the first mapping, i.e. the parallel displacement or translation of the virtual target point grid structure 35 in the organ 3 within the body 5 into an area outside the body 5, and thus creates the prerequisite for the actual therapy preparation, namely the correct placement of the remaining light applicators 9 or their light-emitting applicator tips 19 in the organ 3.

The remaining light applicators 9 then only still have to be guided through the remaining guides 41 of the placement template 39 and fixed with their fixing points 43 to the corresponding fixing point receptacle 51. The operator's degrees of freedom are minimised here, which in turn means that the positions of the remaining light applicators 9 and subsequently the positions of their light-emitting applicator tips 19 are unambiguously fixed after the placement template 39 has been fixed and thus automatically correspond to the target points 33.

Figure 18:
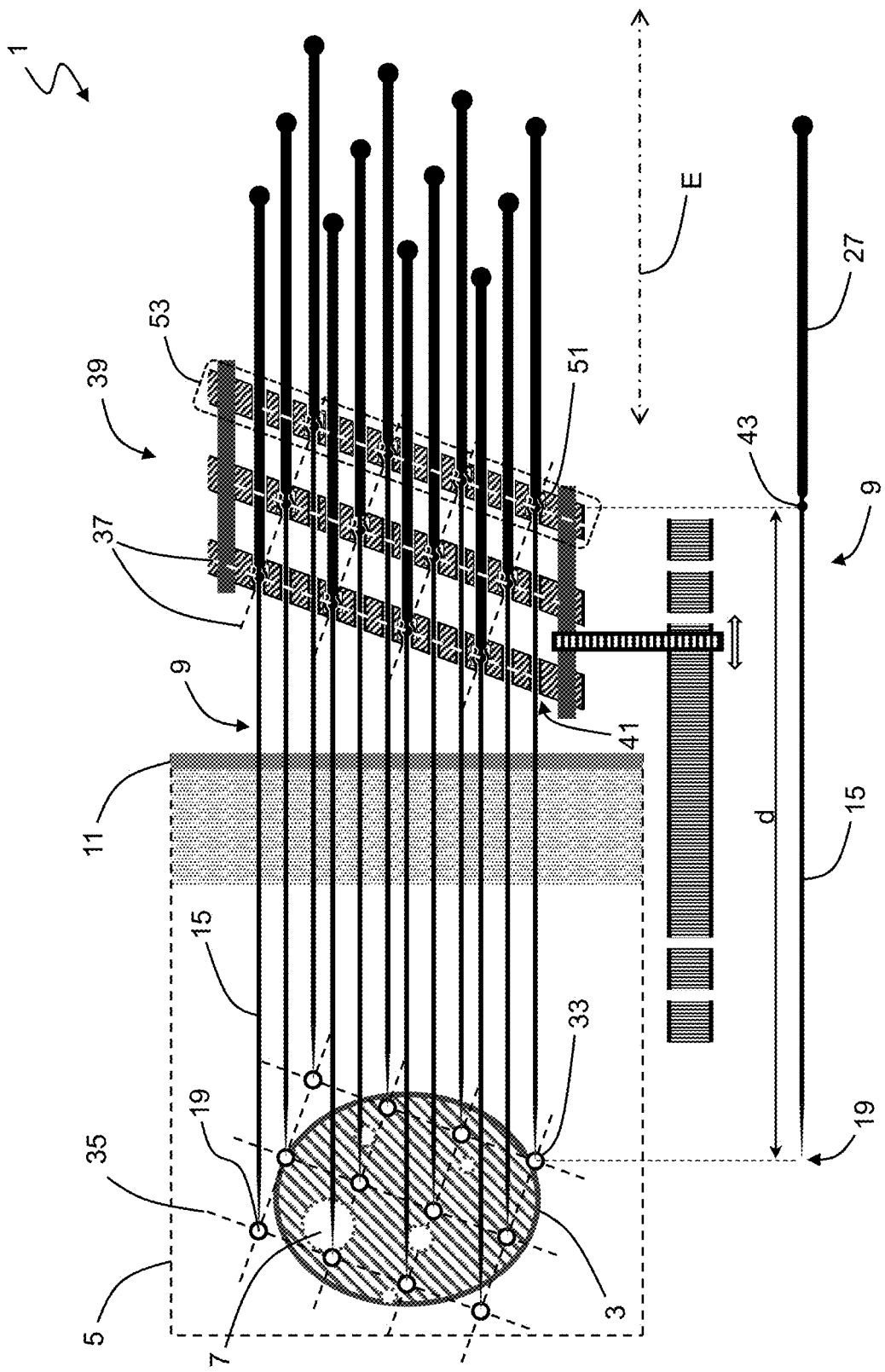
FIG. 18 is a schematic representation of another exemplary embodiment of a system disclosed herein for performing transcutaneous PDT with all light applicators in the pierced position.

FIG. 18 shows an alternative embodiment in which the placement template 39 consists of a plurality of plates positioned fixedly relative to each other, which replace the block from FIG. 18. This makes the placement template 39 lighter and saves material not required for the placement template 39. The plates preferably each have the fixing point receptacles 51 of a fixing point receptacle grid area 53. The plates are preferably arranged parallel to each other. They can run orthogonally to the piercing axis E or, as in FIG. 18, at an angle thereto. Here, too, the fixing point receptacles 51 correspond to the grid points of the fixing point grid structure 37, which is identical in shape and size to the organ-specific virtual target point grid structure 35 for the applicator tips 19 and which is created from the latter by a parallel displacement or translation by the length d.

Figure 19:
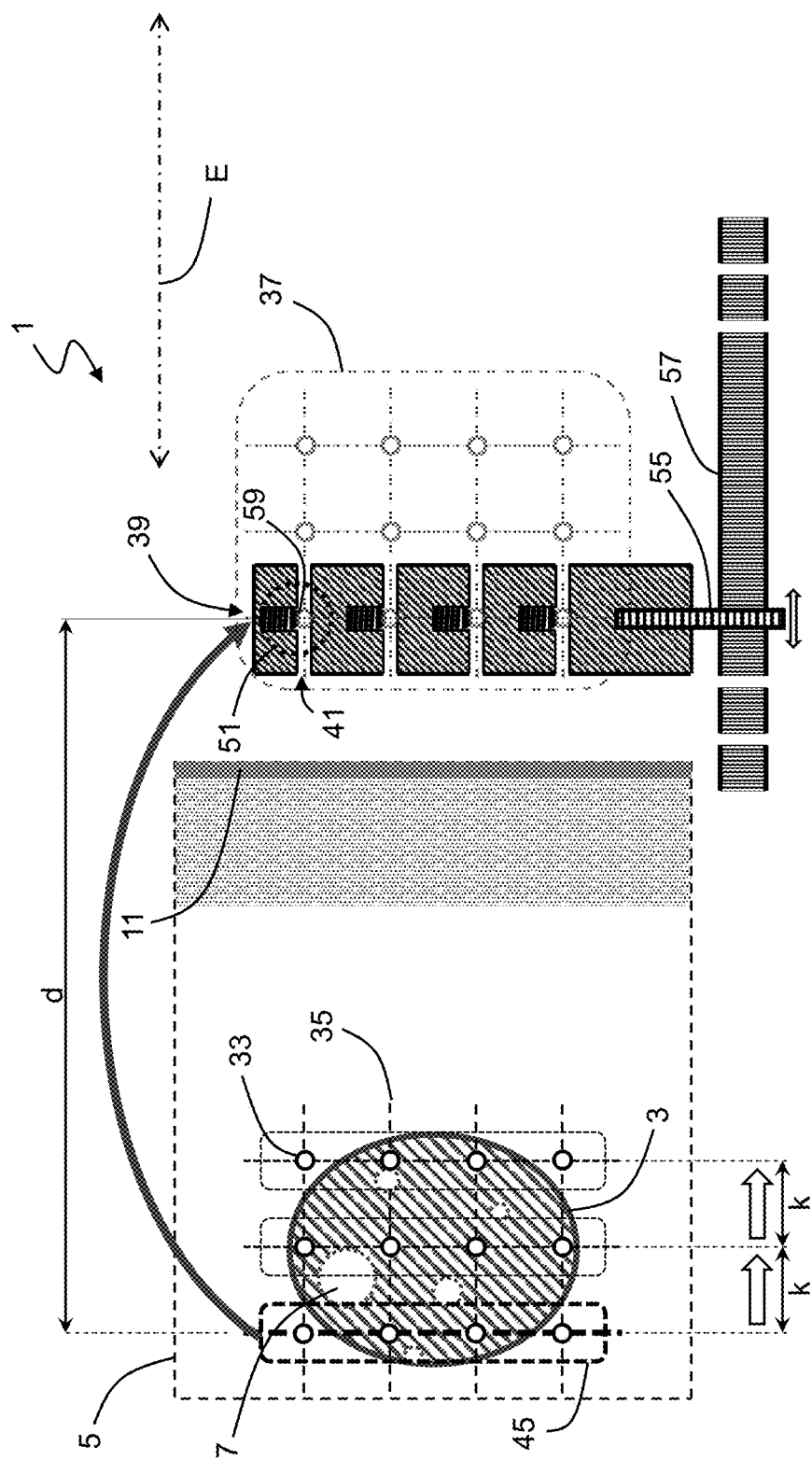
FIG. 19 is a schematic illustration of another exemplary embodiment of a system disclosed herein for performing transcutaneous PDT successively, target point grid area by target point grid area.
Figure 20:
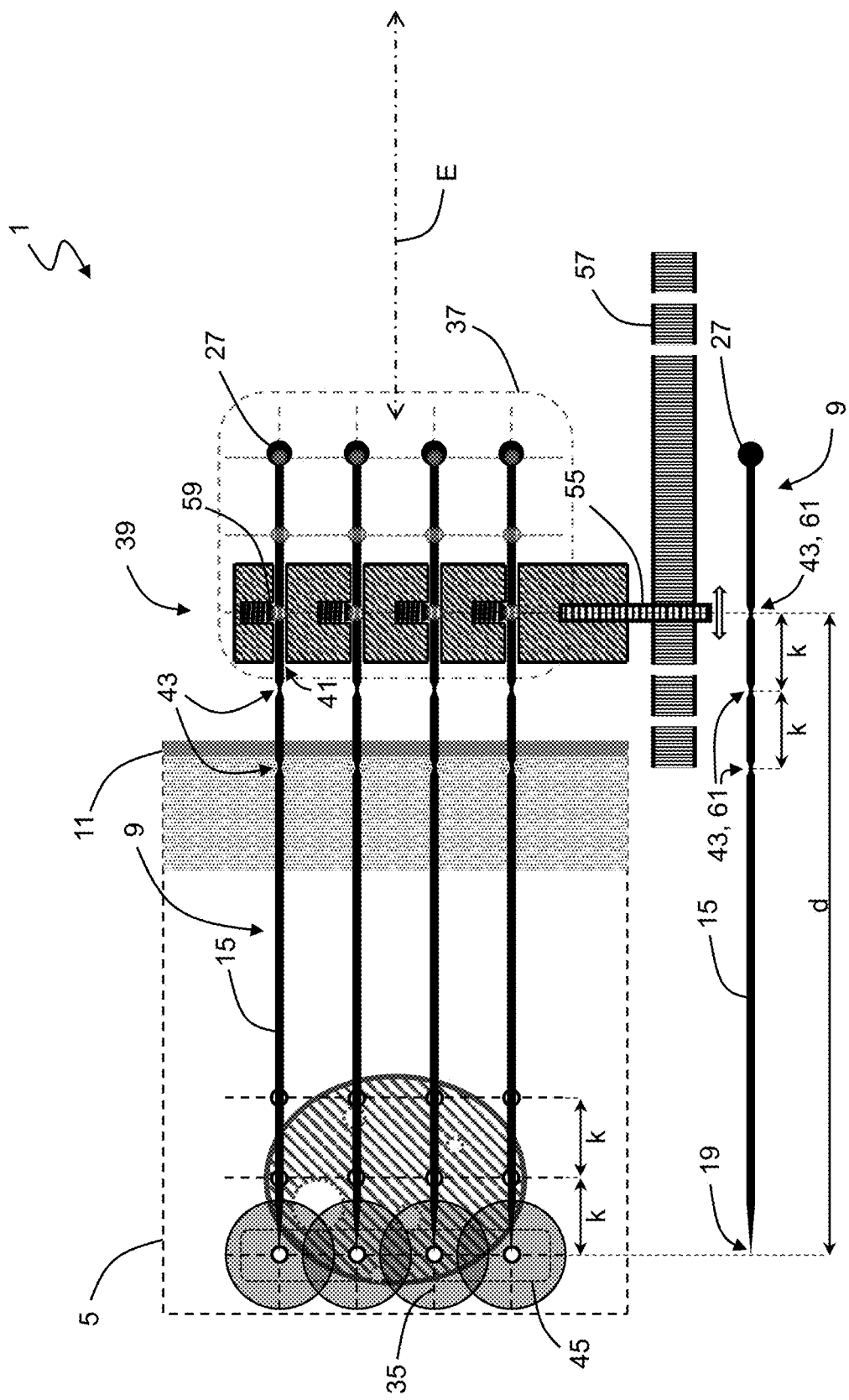
FIG. 20 is a schematic representation of the system shown in FIG. 19 with applicator tips in a first target point grid area.
Figure 21:
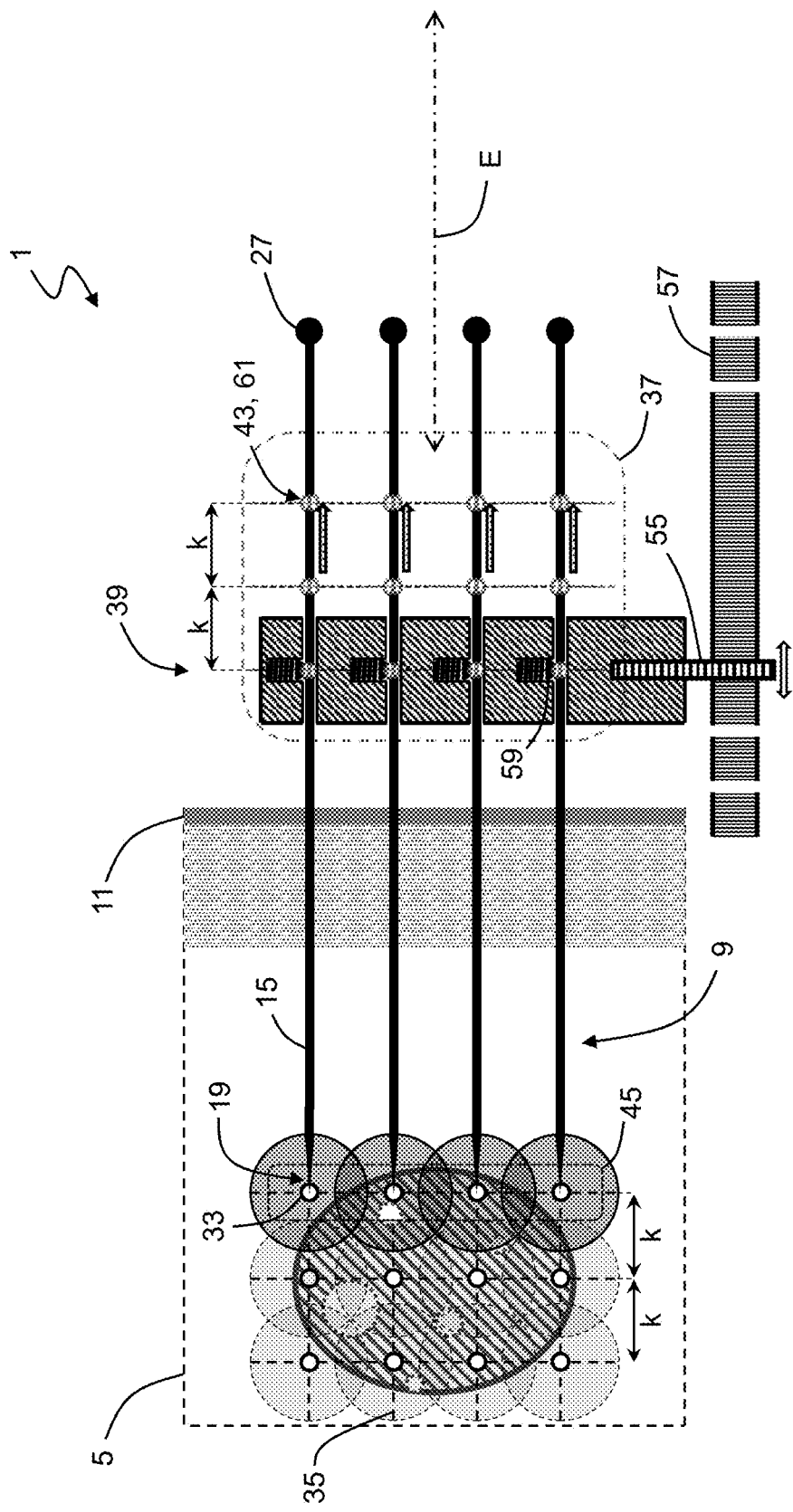
FIG. 21 is a schematic representation of the system shown in FIG. 20 with applicator tips in a third target point grid area.

FIGS. 19 to 21 show an exemplary embodiment for the principle shown in FIGS. 11 to 13 for step-by-step PDT in target point grid areas 45, i.e. show that here the light applicators 9 and with them the light-emitting applicator tips 19 are displaced step by step along the piercing axis E via a plurality of fixing points 43 arranged at a distance k, while the placement template 39 remains fixed in an unchanged position relative to the reference surface 57 via the fastening device 55. The fixing point receptacles 51 are formed here by respective engagement elements 59 engaging laterally in the guides 41 resiliently. The fixing points 43 are correspondingly formed by lateral engagement receptacles 61 in the form of tapers on the light applicator 9. The fixing points 43 have a distance k along the piercing axis E which corresponds to the distance k of the target point grid areas 45 of the target point grid structure 35.

Figure 15:
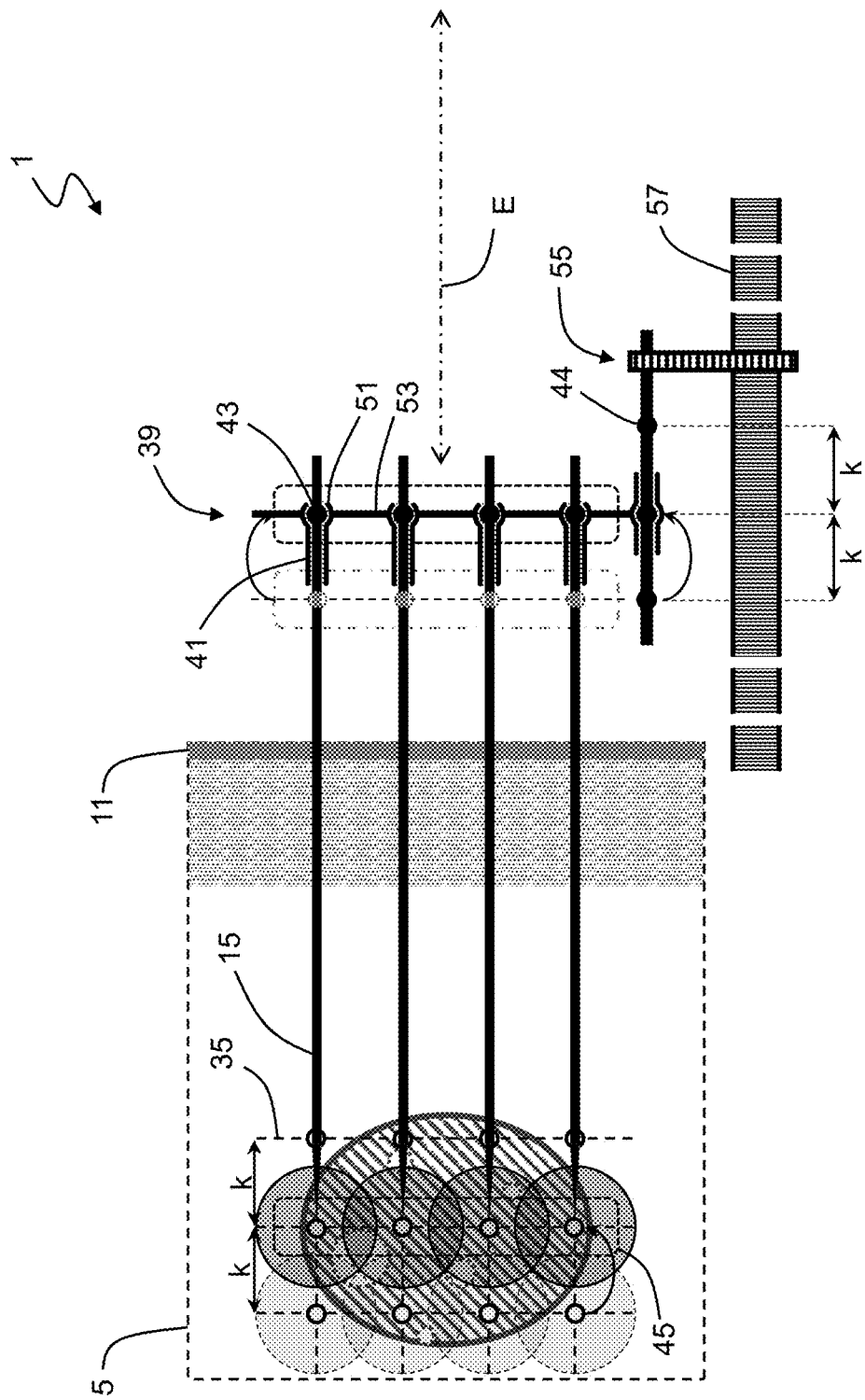
FIG. 15 is a schematic representation of the system shown in FIG. 14 with applicator tips in a second target point grid area.
Figure 16:
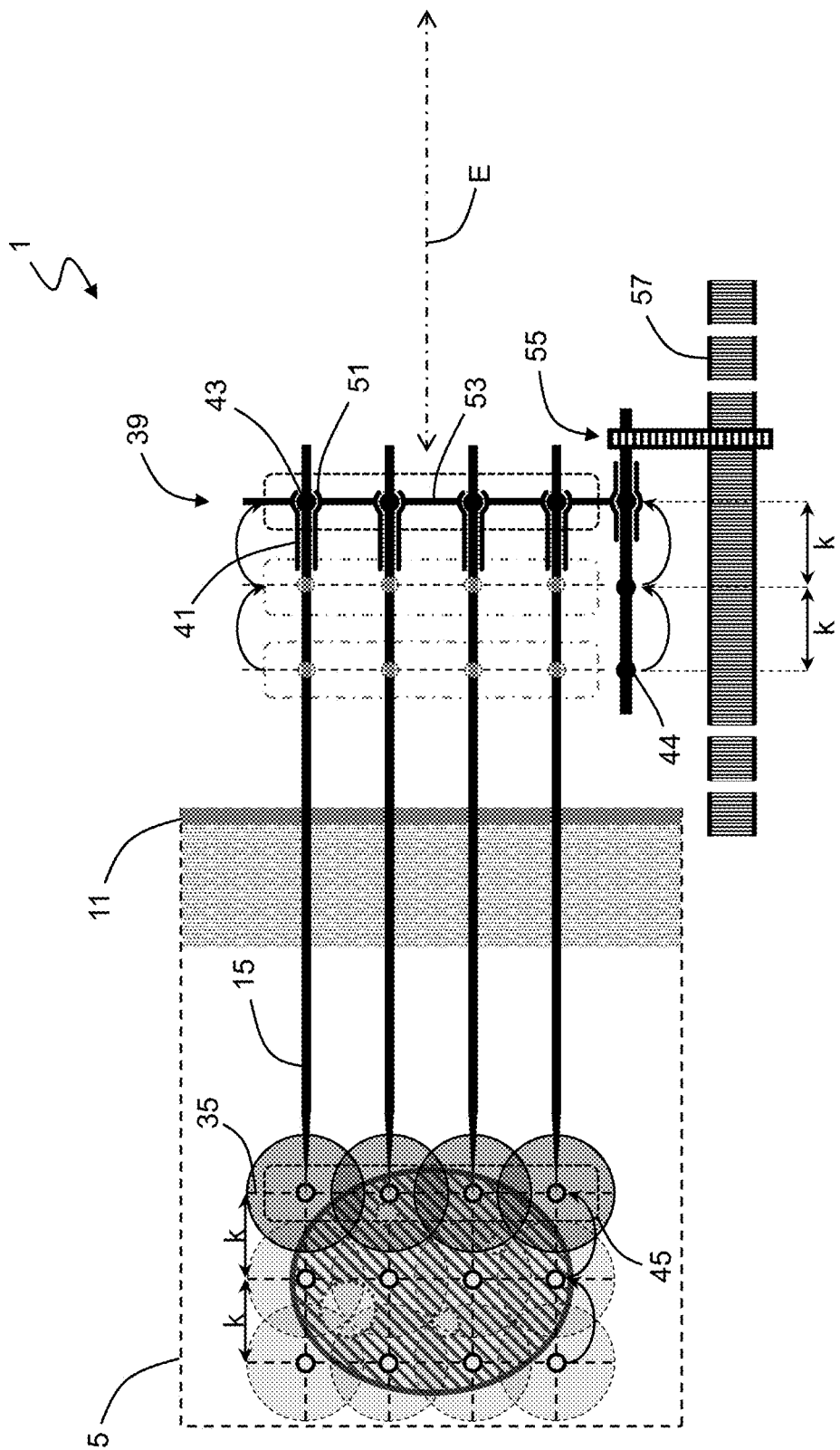
FIG. 16 is a schematic representation of the system shown in FIGS. 14 and 15 with applicator tips in a third target point grid area.
Figure 22:
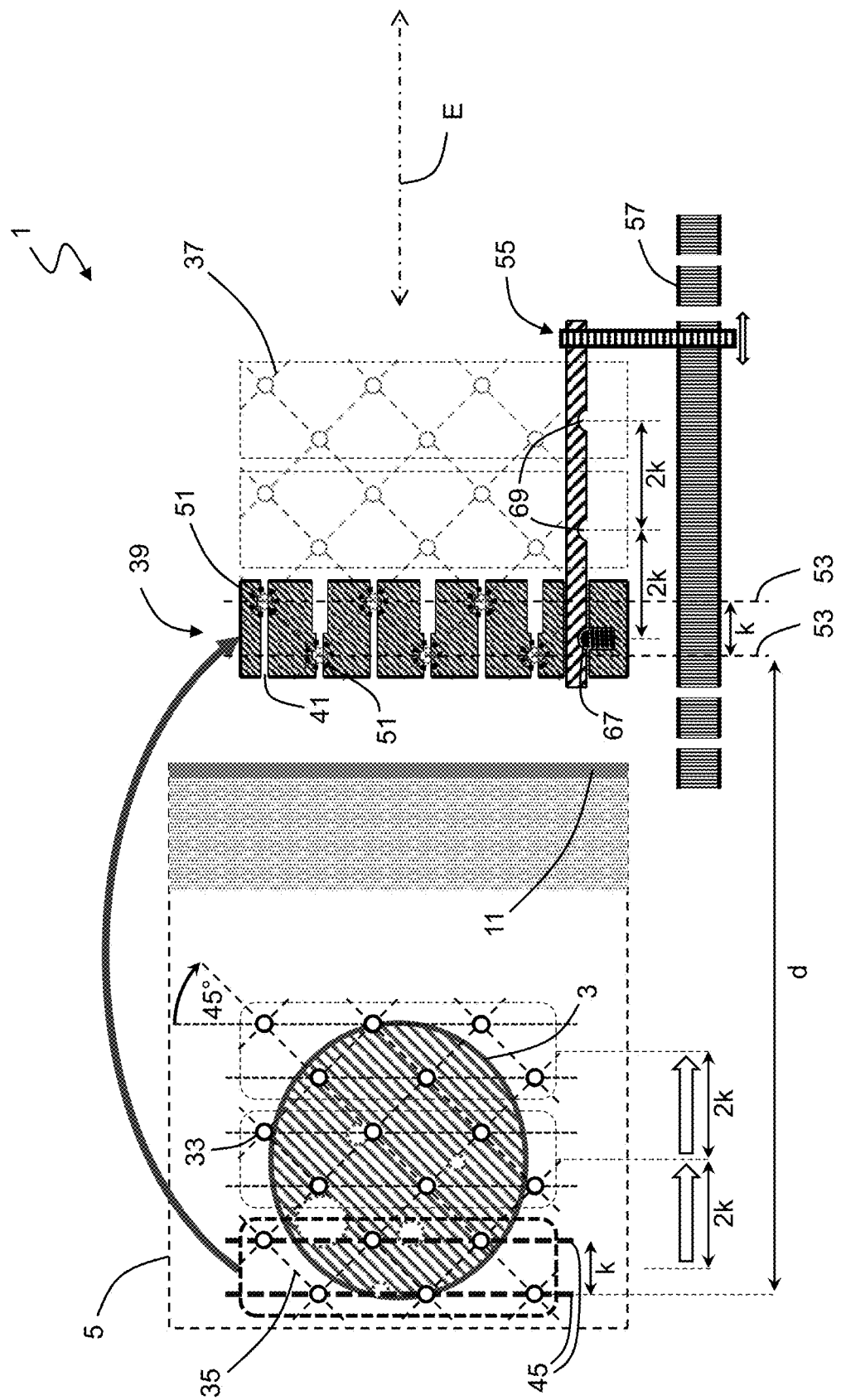
FIG. 22 is a schematic representation of a further exemplary embodiment of a system disclosed herein for performing transcutaneous PDT in two target point grid areas simultaneously.
Figure 23:
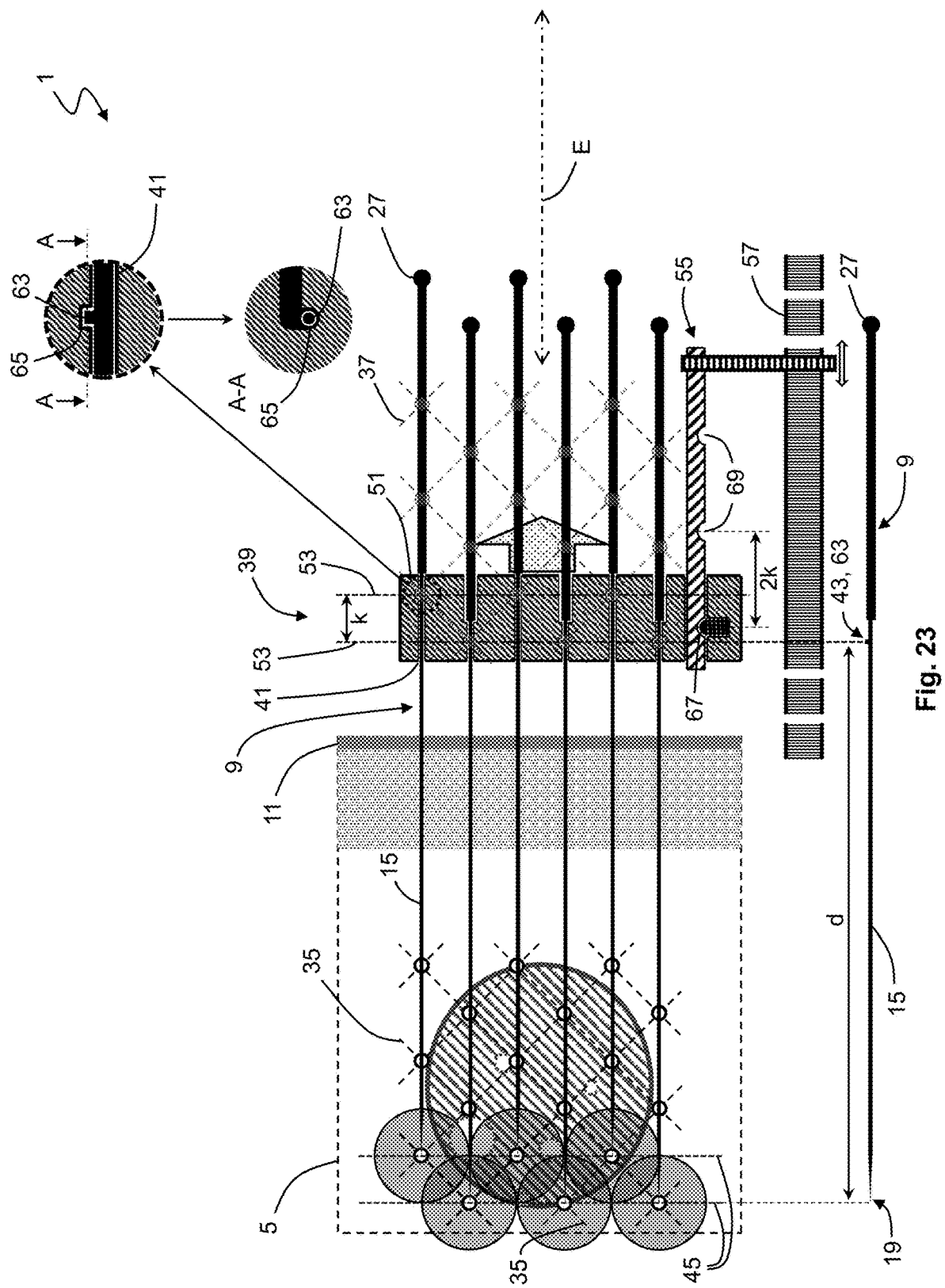
FIG. 23 is a schematic representation of the system shown in FIG. 22 with applicator tips in a first and second target point grid area.
Figure 24:
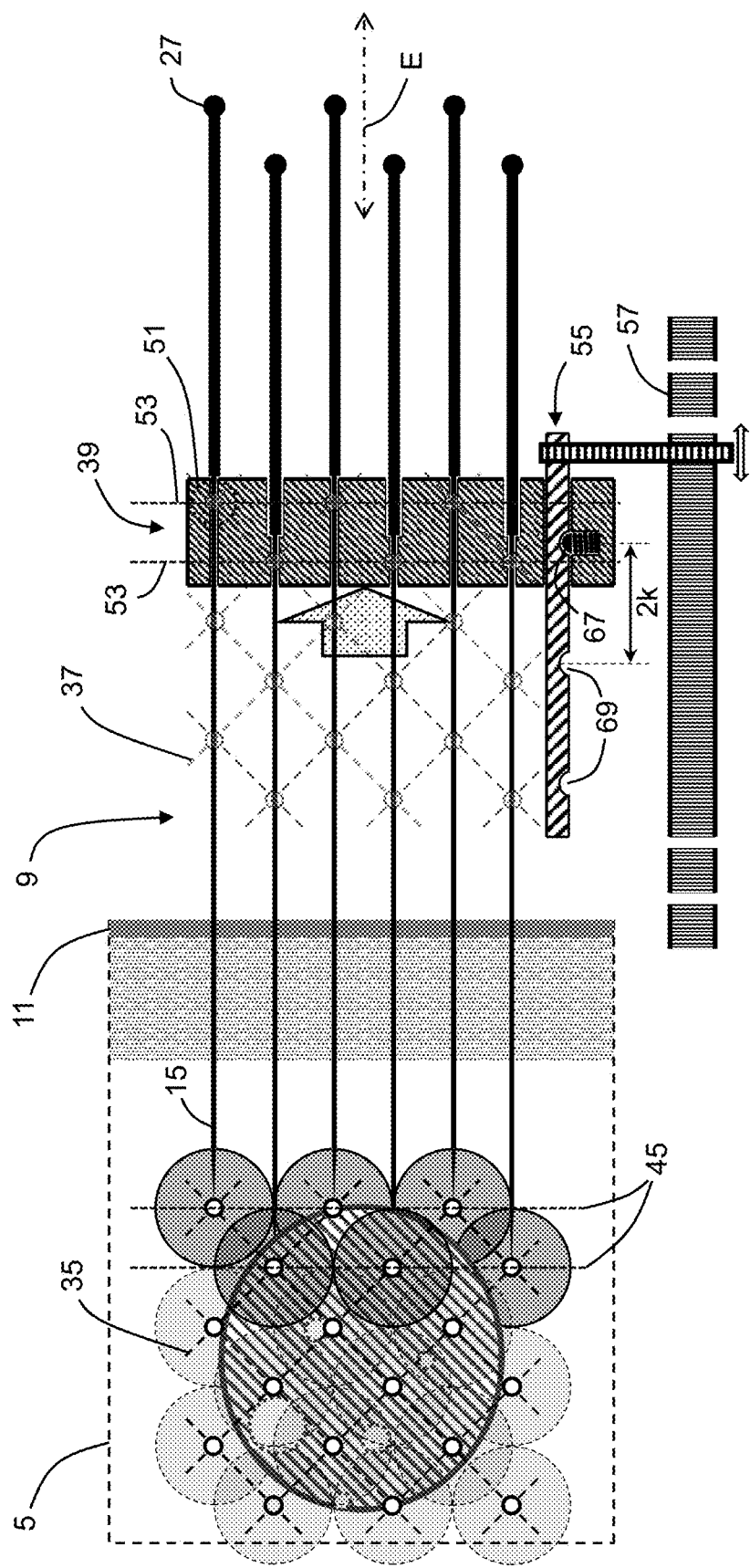
FIG. 24 is a schematic representation of the system shown in FIGS. 22 and 23 with applicator tips in a fifth and sixth target point grid area.

FIGS. 22 to 24 show an exemplary embodiment for the principle shown in FIGS. 14 to 16 for step-by-step PDT in target point grid areas 45. This means that here the placement template 39 does not remain fixed in an unchanged position relative to the fixed reference surface 57 as in the previous exemplary embodiment and only the light applicators 9 are moved step by step, but that the placement template 39 as a whole is moved step by step by defined distances relative to the fixed reference surface 57 and in so doing the inserted light applicators 9 are entrained with their light-emitting applicator tips 19 and thus, in contrast to the case described above, all light applicators 9 are moved jointly or simultaneously by a single action of the operator. At the same time, this exemplary embodiment integrates the principle shown in FIG. 8, namely that in one irradiation unit all target points are covered from a plurality of target point grid areas 45 simultaneously, in the present embodiment specifically from two target point grid areas 45 simultaneously. This principle of treating a plurality of target point grid areas 45 simultaneously is particularly important when the extent of the organ 3 is relatively large—especially along the piercing axis E—because this means that a significantly larger volume can be treated in the same time or with the same number of sequential irradiation units (three irradiation units in the present examples) (in this regard compare FIG. 19 with FIG. 22). For this purpose, the placement template 39 has fixing point receptacles 51 of two adjacent fixing point receptacle grid areas 53. The placement template 39 is then displaceable by twice the length, namely by 2 k, in comparison with the previously described embodiment, in order to carry out the PDT for the following two target point grid areas 45. With this procedure, i.e. that all target points from a plurality of target point grid areas 45 are covered simultaneously in one irradiation unit, larger organs 3, i.e. organs that extend more along the piercing axis E, can be treated in the same time, i.e. with the same number of irradiation units, in comparison with the previously described embodiment (FIGS. 19 to 21) (in this regard compare FIG. 21 with FIG. 24). In the present embodiment, the fixing points 43 and the fixing point receptacles 51 form a type of bayonet lock in which a lateral projection 63 on the light applicator 9 can be rotated into a corresponding lateral receptacle securing means 65 in the guide 41 by rotation of the light applicator 9 about the piercing axis E. The fastening device 55 of the placement template 39 has an engagement element 67 which engages in engagement receptacles 69 arranged fixedly with respect to the reference surface 57, in each case at a distance 2 k along the piercing axis E.

FIGS. 25a,b and 25c,d schematically illustrate the two principal variants of the "dragging effect" to be avoided, which can occur individually or in combination during transcutaneous PDT. FIG. 25a shows the normal position and the original shape of the organ 3 in the patient's body 5 without the light applicators 9 inserted. If the light applicators 9 then inserted during the course of the therapy are moved or retracted proximally jointly or simultaneously and if the total static frictional force exerted and effective by the light applicators 9 on the organ 3 is greater than the binding forces acting within the surrounding tissue 4 directly connected to the organ 3 and in turn smaller than the binding forces effective within the organ 3 itself, then a "dragging" of the organ 3 by the light applicators 9 occurs in such a form that the light applicators 9 entrain or pull with them the organ 3 as a whole, while maintaining its shape within the body 5. This means that, although the shape of the organ 3 is maintained, its position within the body 5 changes, as schematically shown in FIG. 25b. With regard to the originally defined and planned parallel displacement between the target point grid structure and the fixing point grid structure, this means that, although the shape of the target point grid structure is maintained, its position or its originally defined distance d to the fixing point grid structure changes in an undefined and thus undesirable manner and thus the defined distance d between the target point grid structure and the fixing point grid structure characterising the parallel displacement is no longer maintained.

Figure 25D:
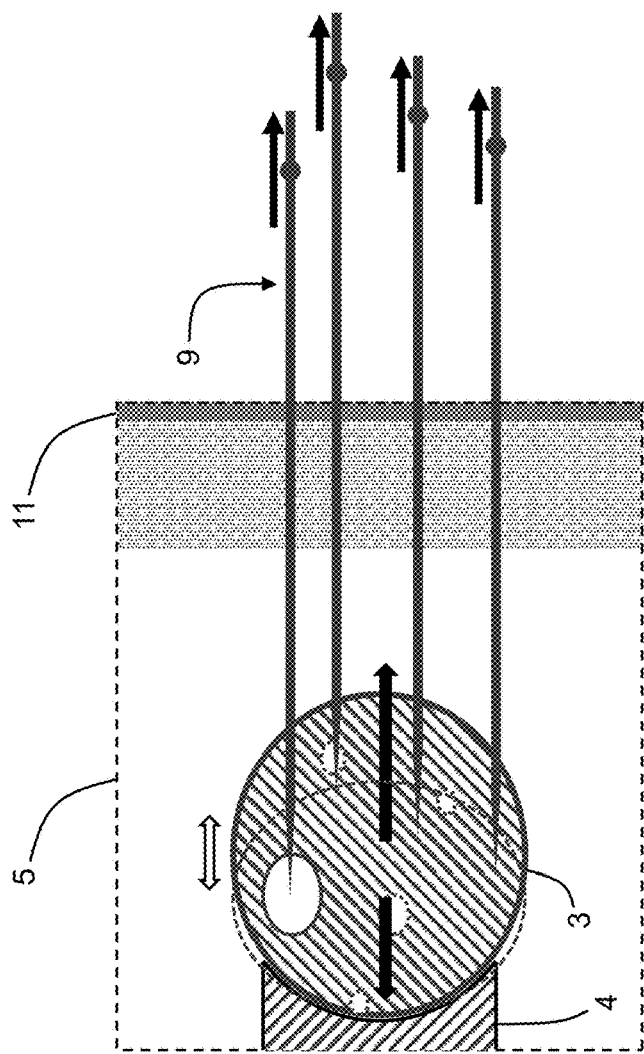
FIG. 25c and FIG. 25d are schematic representations of the dragging effect to be avoided in principle according to the second variant.
Figure 25C:
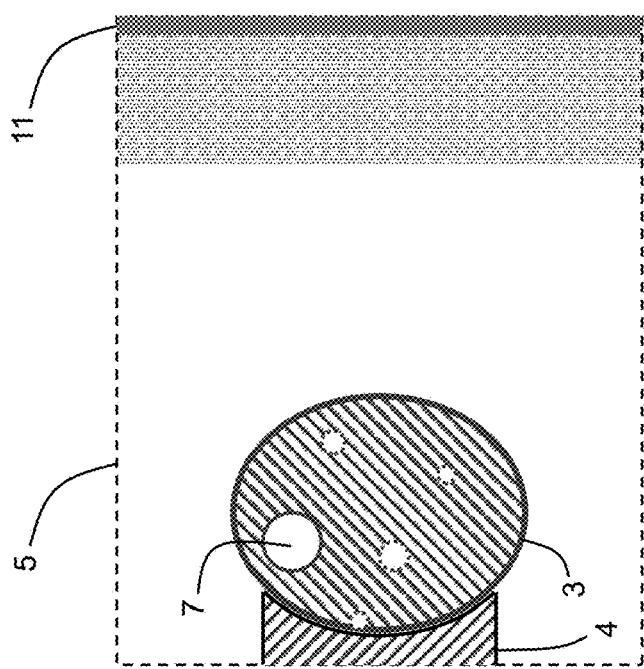

FIG. 25c shows once again the normal position and original shape of the organ 3 in the patient's body 5 without the light applicators 9 inserted. If the light applicators 9, which are inserted during the course of the therapy, are jointly or simultaneously retracted proximally and if the total static frictional force exerted by the light applicators 9 on the organ 3 is now greater than the binding forces acting within the organ 3 itself, which are also smaller than the binding forces acting within the surrounding tissue 4 directly connected to the organ 3, as shown in FIG. 25d, then a "dragging" of the organ 3 by the light applicators 9 occurs in such a way that the light applicators 9 pull the organ 3 apart or stretch it. This means that, although the position of the organ 3 in the body 5 is largely maintained, its shape changes, as schematically shown in FIG. 25d. With regard to the originally defined and planned parallel displacement between the target point grid structure and the fixing point grid structure, however, this means that although the position of the target point grid structure or its originally defined distance d from the fixing point grid structure is maintained in a first approximation, its shape changes in an undefined and thus undesirable manner.

Both forms of "dragging" described above and their effects on the shape and position of the organ 3 in the body 5 become more significant as the number of light applicators 9 used increases, and should preferably be taken into account appropriately when planning the therapy, since the (total) static friction exerted on the organ 3 increases accordingly, and thus the effects of the change in position of the organ 3 (see FIG. 25b) and/or the change in shape of the organ 3 (see FIG. 25d) also increase in the same way.

Particularly in the case of step-by-step PDT in target point grid areas 45, in which the placement template 39 as a whole is displaced step by step by defined distances relative to the fixed reference surface 57 and the introduced light applicators 9 are moved simultaneously or jointly with their light-emitting applicator tips 19, as explained on the basis of FIGS. 11 to 13 in schematic form and exemplified by FIGS. 22 to 24 in a specific embodiment, this is problematic because it is not clear where the organ 3 is located or to what extent the organ 3 has deformed when the light applicators 9 are retracted for PDT in the next target point grid area 45. For example, in the set-up of FIG. 22, if the two fixing point receptacle grid areas 53 are displaced by the distance 2 k from the distal position to the adjacent proximal position, which is done by displacing the placement template 39 from the distal engagement receptacle 69 to the directly adjacent proximal engagement receptacle 69 (in FIG. 22, the centrally located engagement receptacle 69), then the applicator tips 19 are also displaced by the distance 2 k in the proximal direction. However, because, contrary to the idealised representation in FIG. 24, in reality the organ 3, as a result of the "dragging effect" has also been "entrained" over a certain, but above all undefined distance in the proximal direction, as shown schematically in FIG. 25a,b, and/or has been stretched or extended by an undefined length, as shown schematically in FIG. 25c,d, in an undesirable manner, the organ-based target point grid areas 45 are now also no longer in their original position, as shown in idealised form in FIG. 24, but are displaced in the proximal direction together with the organ 3 displaced and/or stretched in reality and can thus no longer be reached as originally intended by the applicator tips 19 shifted "merely" by the distance 2 k. The aim of realising an effective and, above all, homogeneous irradiation of the organ 3 on the basis of the original target point grid structure 35 by sequential displacement and latching of the template 39 in the given engagement receptacles 69 in a manner that is simple and convenient for the operator can no longer be achieved under these circumstances, i.e. that the organ 3 is entrained and/or stretched in an undesirable and, above all, undefined manner by the total static frictional force, acting on the organ 3, of the light applicators 9 moved jointly or simultaneously.

Figure 26:
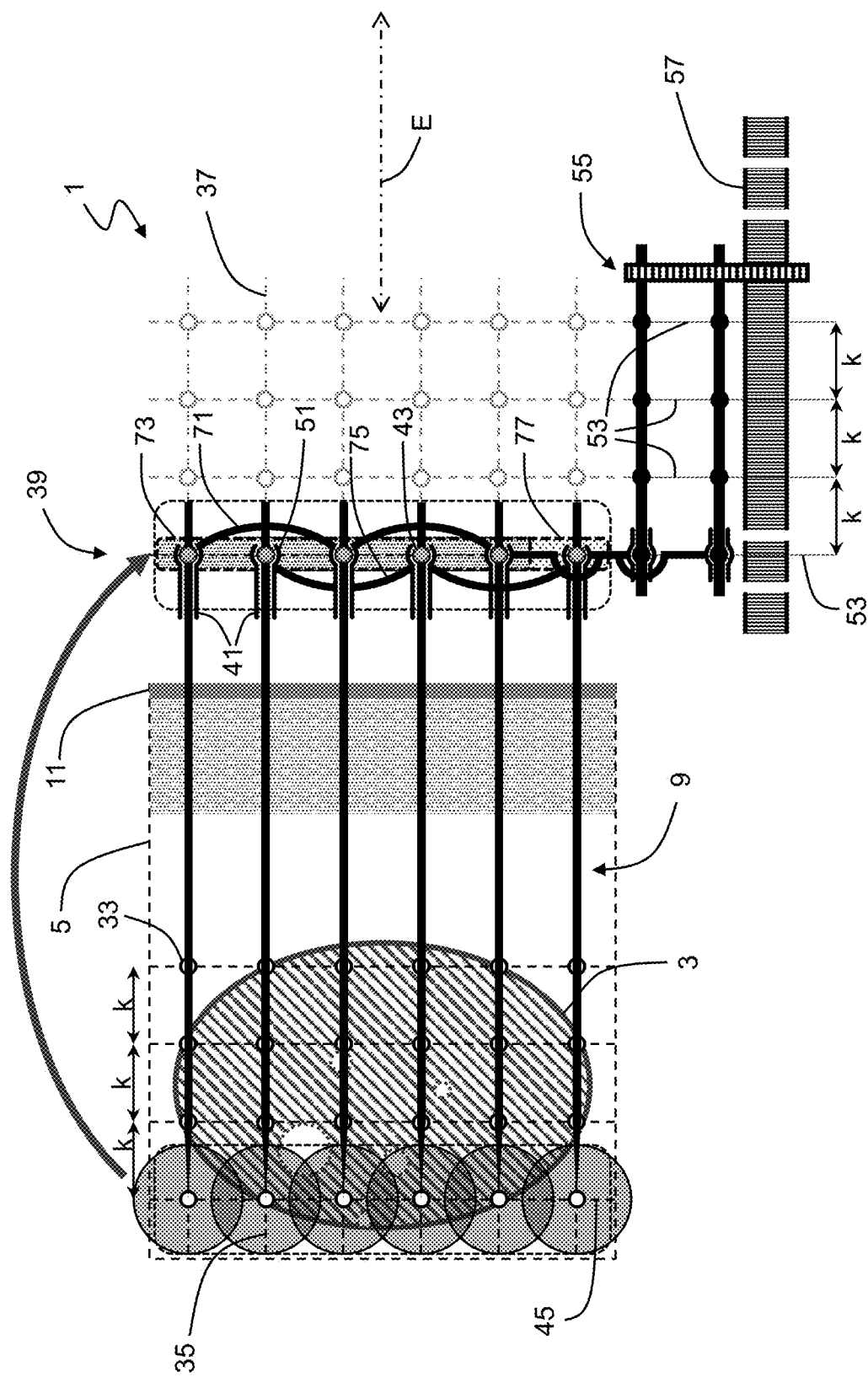
FIG. 26 is a schematic representation of an exemplary embodiment of a system according to the second aspect of the present disclosure for avoiding the dragging effect in transcutaneous PDT with applicator tips in a first target point grid area.
Figure 27:
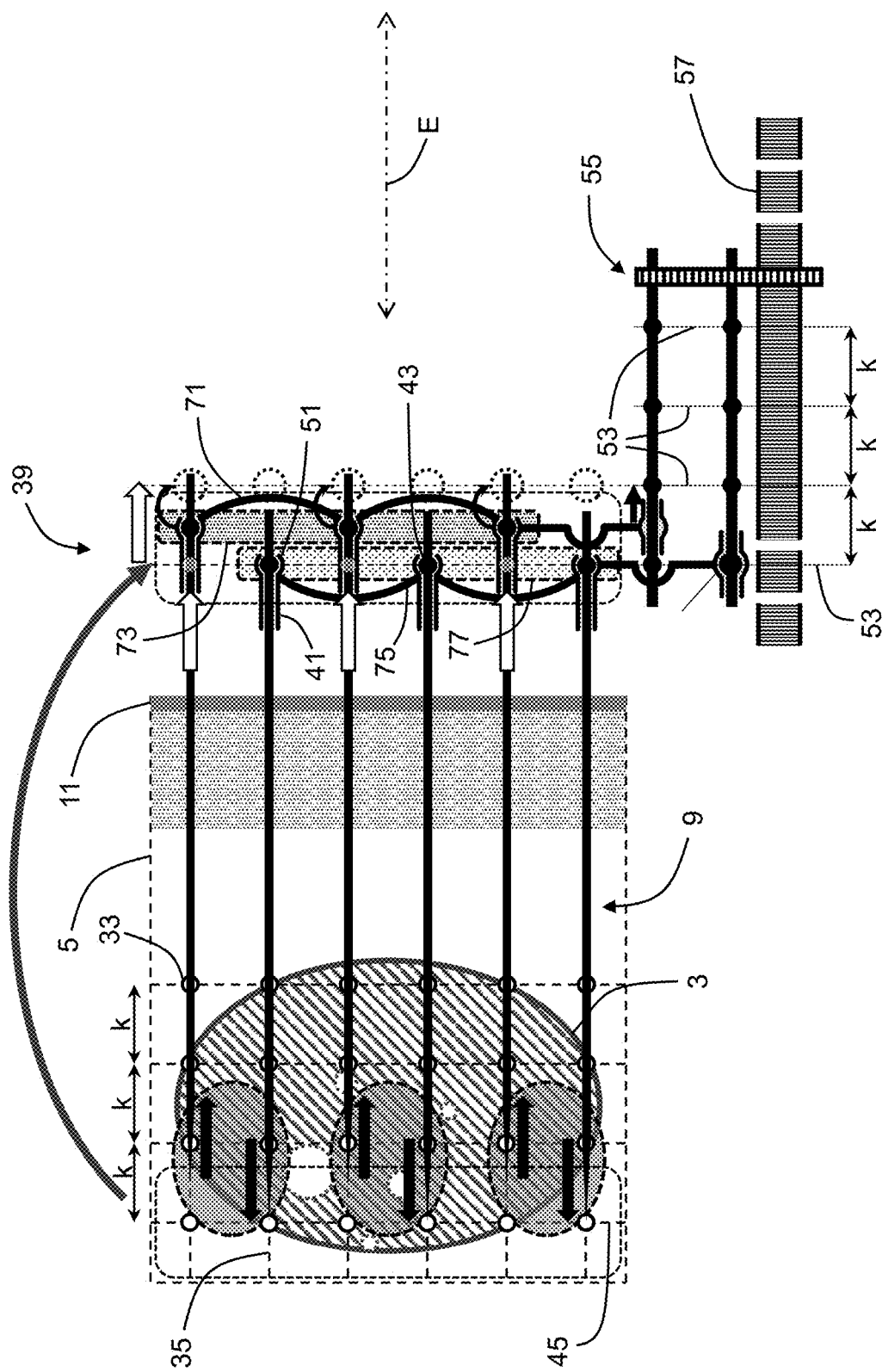
FIG. 27 is a schematic representation of the system shown in FIG. 26 with a first subset of applicators in a first template part, the applicator tips of which are pulled towards a second target point grid area, while a second subset of applicators is held in place in a second template part.
Figure 28:
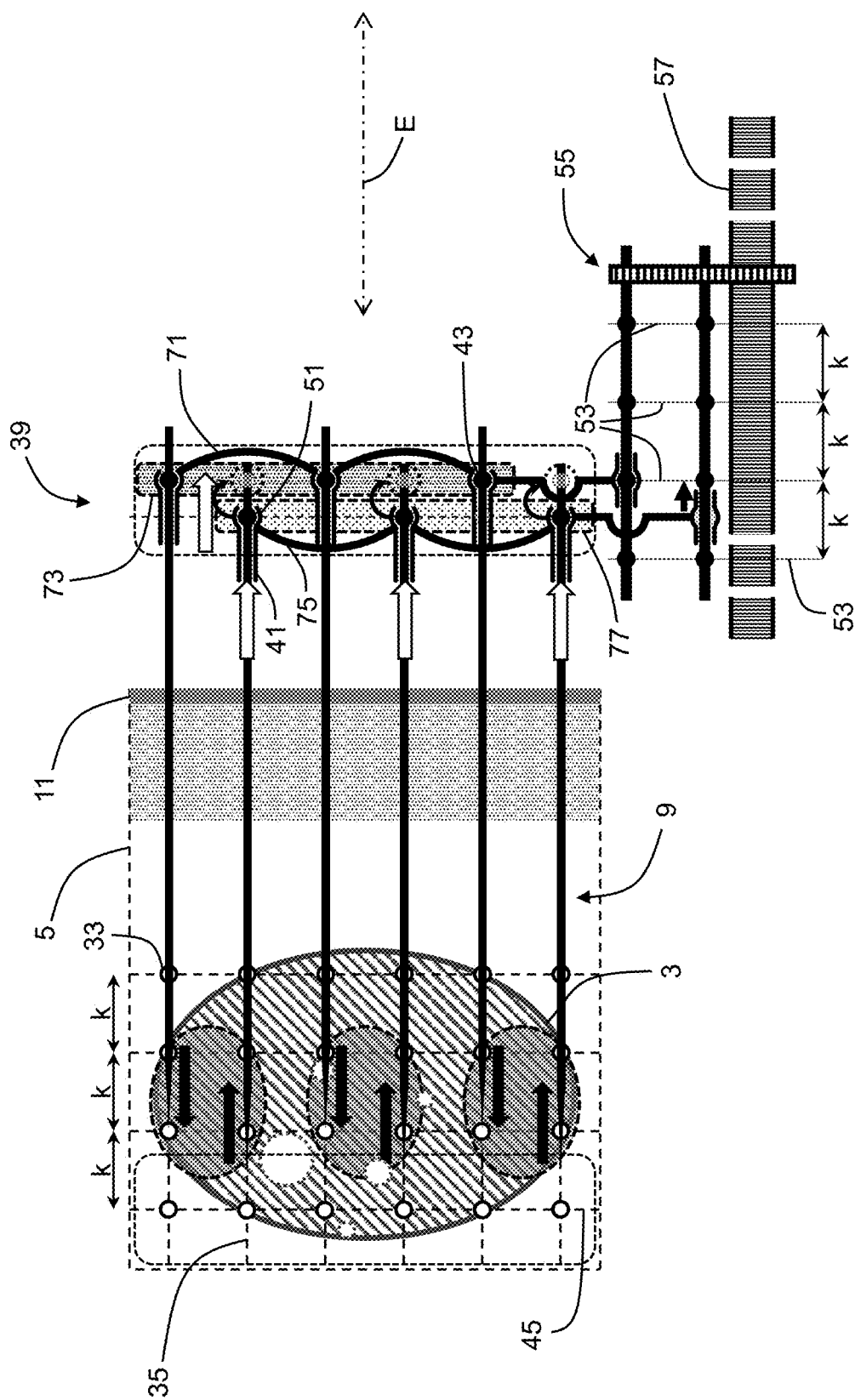
FIG. 28 is a schematic representation of the system shown in FIGS. 26 and 27, wherein the applicator tips of the first subset of applicators are held in the second target point grid area while the applicator tips of the second subset of applicators are pulled towards the second target point grid area.
Figure 29:
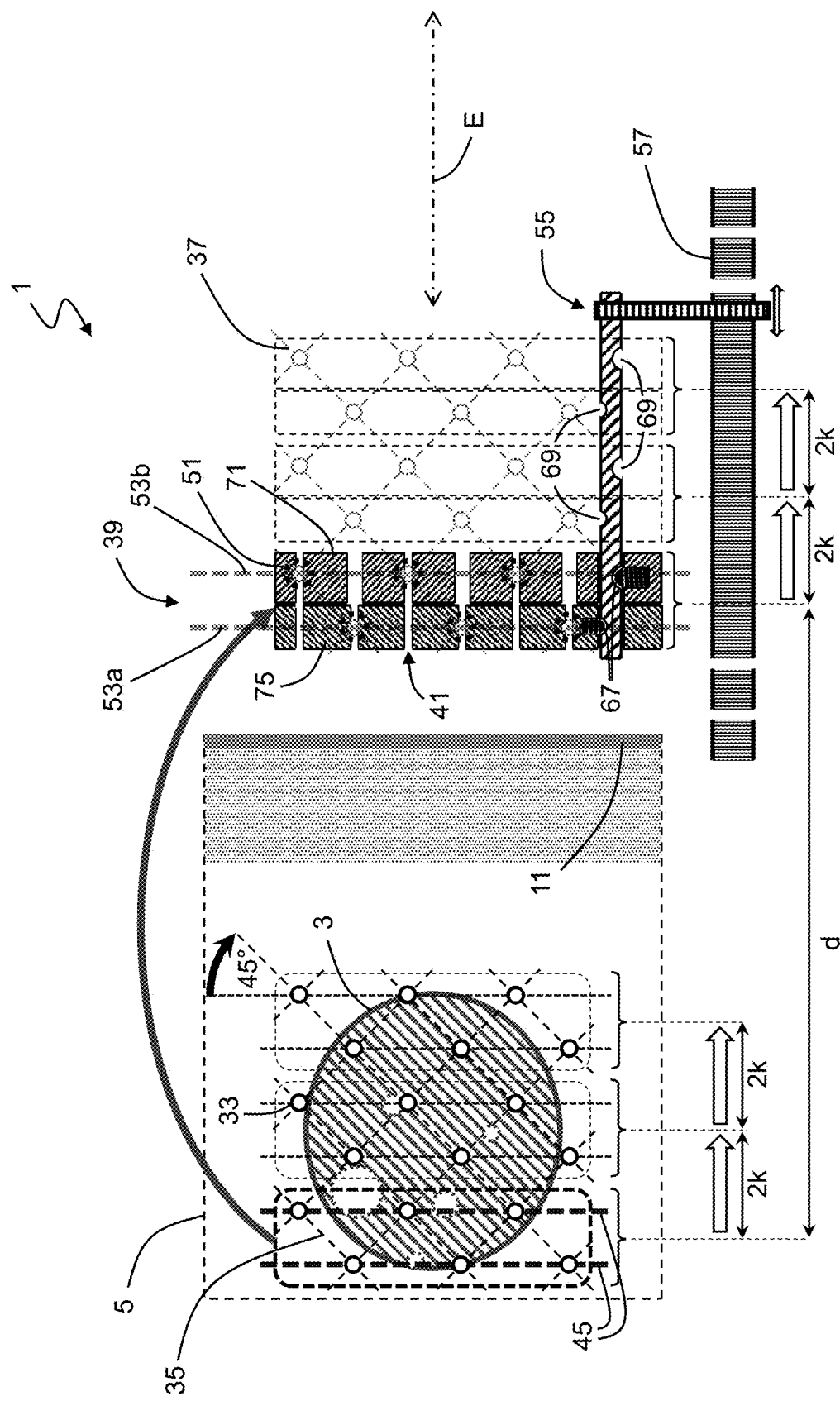
FIG. 29 is a schematic illustration of an exemplary embodiment of a system according to the second aspect of the present disclosure for avoiding the dragging effect in transcutaneous PDT.

FIGS. 26 to 28 show a solution principle for this problem. The placement template 39 here has at least two parts, namely a first template part 71, which defines a first subset 73 of the guides 41 with fixing point receptacles 51, and a second template part 75, which defines a second subset 77 of the guides 41 with fixing point receptacles 51. The first template part 71 is guided displaceably here along the piercing axis E relative to the second template part 75. By means of the template parts 71, 75, various subsets of light applicators 9 can be selectively moved or held jointly in a concerted manner by the corresponding subsets 73, 77 of guides 41 with fixing point receptacles 51. This has the advantage that one subset of light applicators 9 can be used to hold the organ 3 while the other subset is moved. The "dragging effect" can thus be avoided or at least reduced by holding one subset of light applicators 9 while the other is pulled out. The respective subsets can be moved alternately while the other is held. The joint movement and joint holding of the light applicators 9 can be effected by corresponding movement or holding, respectively, of the template parts 71, 75. FIG. 27 shows how the first template part 71 with the first subset of light applicators 9 is moved while the second template part 75 is held. The sum of the static frictional forces exerted on the organ 3 by both the moved light applicators 9 of the first subset 73 and the held light applicators 9 of the second subset 77 is, to a first approximation, zero, which is illustrated schematically in FIG. 27 by the pairing of force arrows within the dashed ellipses, shaded grey, in the organ 3, which are of equal length but point in opposite directions. This approach makes it possible to move a plurality of light applicators 9 jointly or simultaneously in a common direction, here in the proximal direction, without entraining the organ 3 and/or without deforming the organ 3.

FIG. 28 shows how the second template part 75 with the second subset 77 of light applicators 9 is retracted while the first template part 71 with the first subset 73 of light applicators 9 is held in place. The sum of all static frictional forces exerted on the organ 3 by all light applicators 9 jointly is again in this case too, to a first approximation, zero, which is again illustrated here by the paired representation of force arrows of equal length but pointing in opposite directions within the dashed ellipses shaded grey, so that the organ 3 is neither entrained nor deformed despite the simultaneous movement of a plurality of light applicators 9, namely those of the second subset 77, in a common direction.

The relatively high density of the guides 41 and fixing point receptacles 51 and, as a result, the correspondingly high potential density of applicators 9 in the organ 3, as well as the arrangement of guides 41 and fixing point receptacles 51 of different subsets 73 and 77 and, correspondingly, of applicators 9 of different subsets 73 and 77 in relation to each other, i.e. the regular change in the affiliation of guides 41 and fixing point receptacles 51 to the different subsets 73 and 77, mean that local displacements and deformations within the organ 3 can also be largely avoided.

FIGS. 29 to 32 show another exemplary embodiment for avoiding the "dragging effect", in which the PDT is performed simultaneously in two target point grid areas 45, analogously to the exemplary embodiment according to FIGS. 22 to 24. As already explained there, this procedure plays an important role when the organ 3 to be treated is larger and, above all, more extensive along the piercing axis E, because a larger volume can thus be treated within the same time or with the same number of sequential irradiation units (in the present case three sequential irradiation units) (compare FIG. 29 with FIG. 19). The placement template 39 here has two parallel plates 71, 75, which form the template parts 71, 75 and are movable relative to each other in a guided manner along the piercing axis E. The first template part 71 has the fixing point receptacles 51 from a first fixing point receptacle grid area 53b and the second template part 75 has the fixing point receptacles 51 from a second fixing point receptacle grid area 53a. In a first relative position shown in FIGS. 29 and 30, in which the plates 71, 75 are adjacent to each other, the placement template 39 is substantially no different from the exemplary embodiment shown in FIGS. 22 to 24 and can be used in the same way, provided there is no fear of a "dragging effect".

Figure 31:
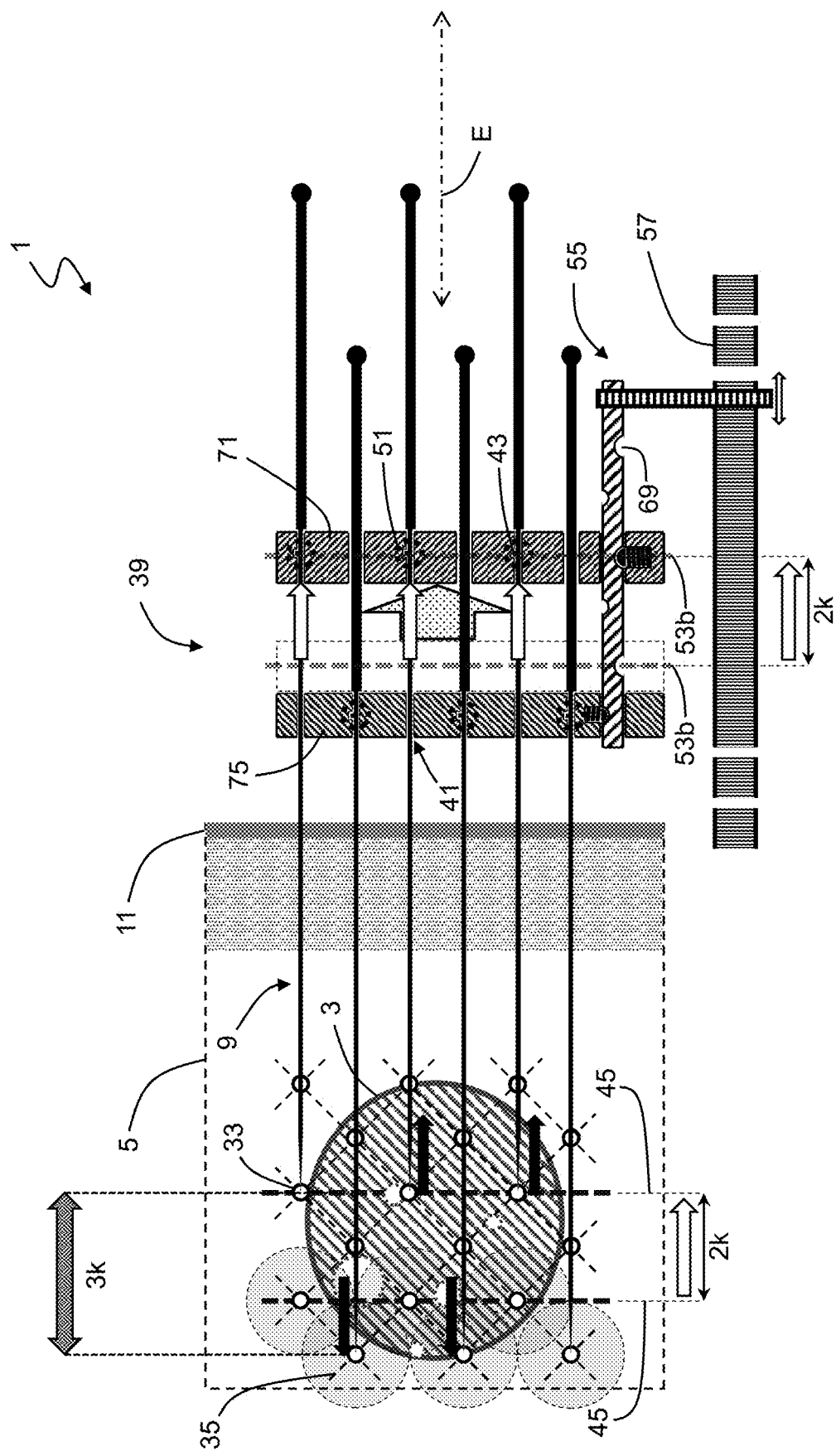
FIG. 31 is a schematic representation of the system shown in FIGS. 29 and 30 with a first subset of applicators in a first template part, the applicator tips of which are pulled towards a fourth target point grid area, while a second subset of applicators is held in place in a second template part.

However, if there is a fear of a "dragging effect", the first template part 71 can first be retracted by 2 k while the second template part 75 is held in place, as shown in FIG. 31. As soon as the first template part 71 is positioned, the second template part 75 can be retracted proximally by 2 k, as shown in FIG. 32, while the first template part 71 is held in place.

Figure 30:
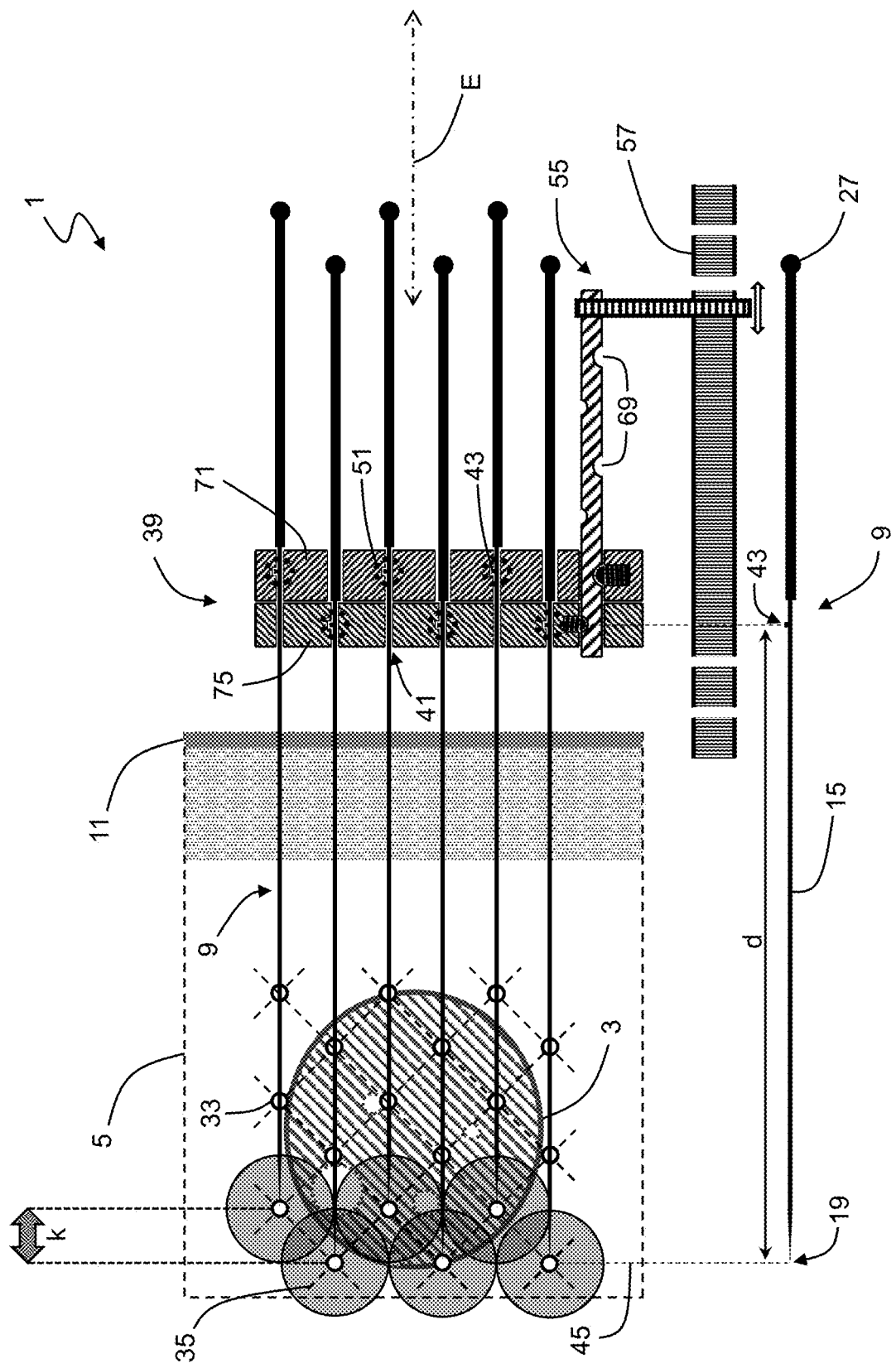
FIG. 30 is a schematic representation of the system shown in FIG. 29 with applicator tips in a first and second target point grid area.
Figure 32:
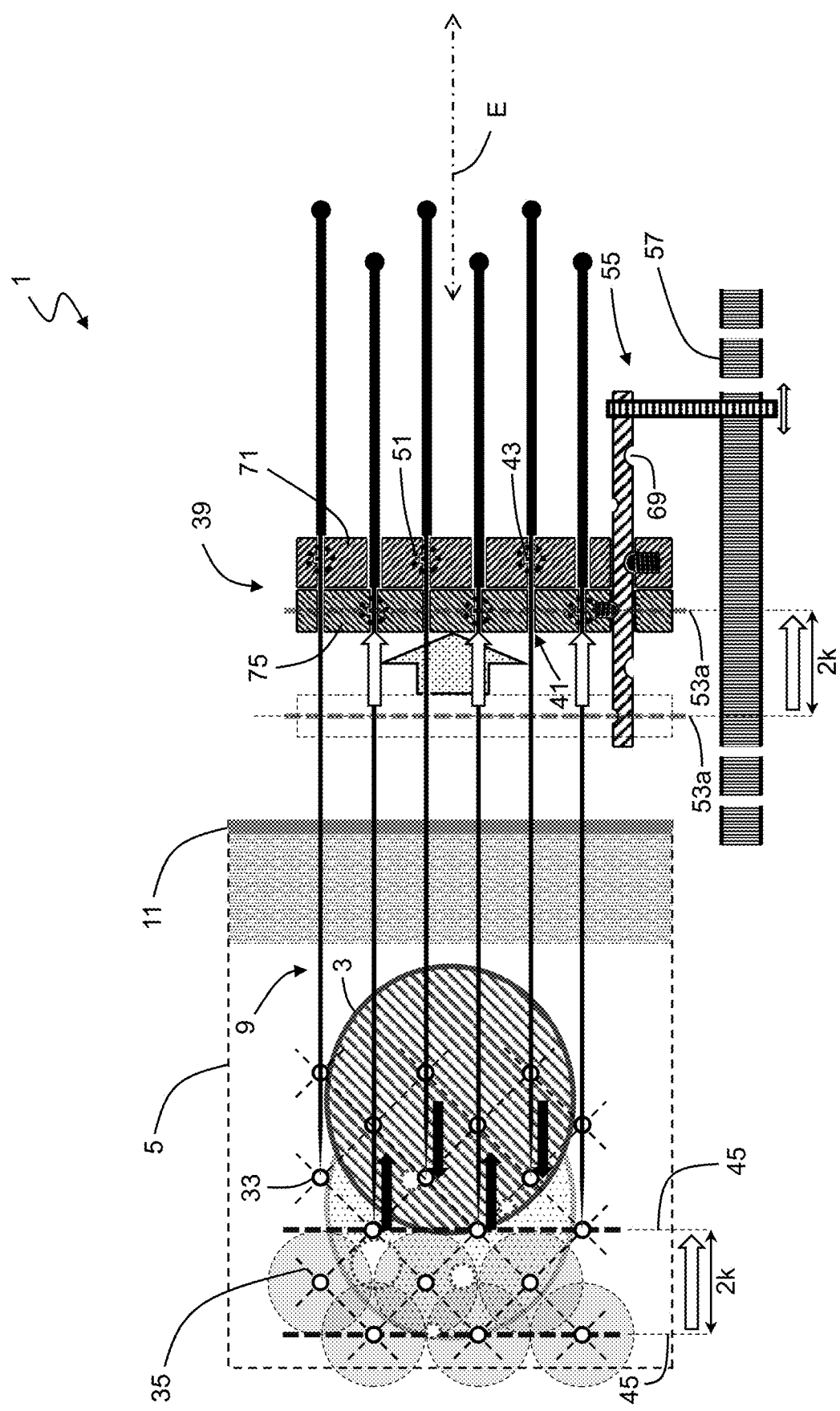
FIG. 32 is a schematic representation of the system shown in FIG. 31, wherein the applicator tips of the first subset of applicators are held in the fourth target point grid area while the applicator tips of the second subset of applicators are pulled towards a third target point grid area.
Figure 33:
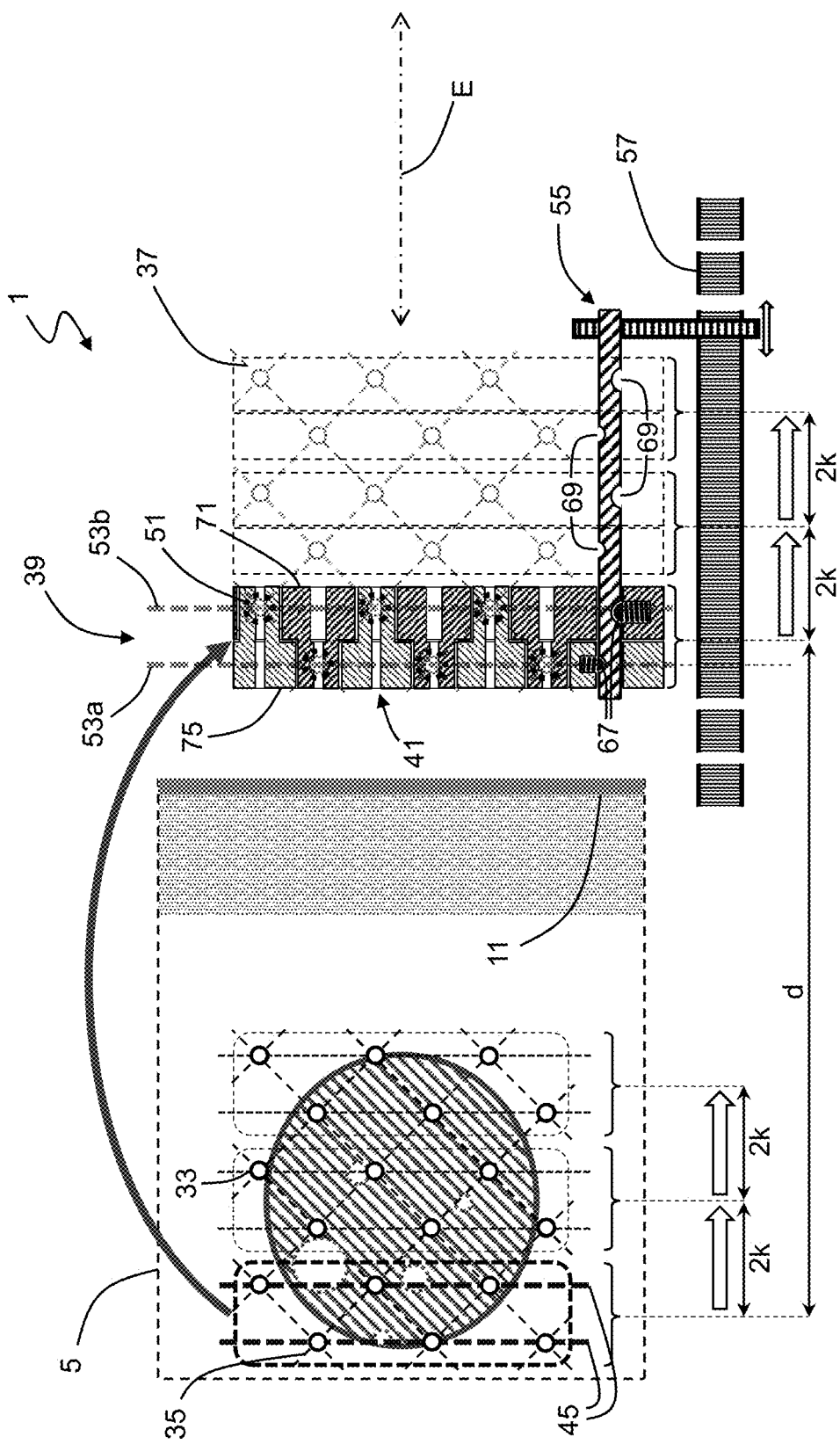
FIG. 33 is a schematic representation of an improved exemplary embodiment of a system according to the second aspect of the present disclosure for avoiding the dragging effect in transcutaneous PDT.
Figure 34:
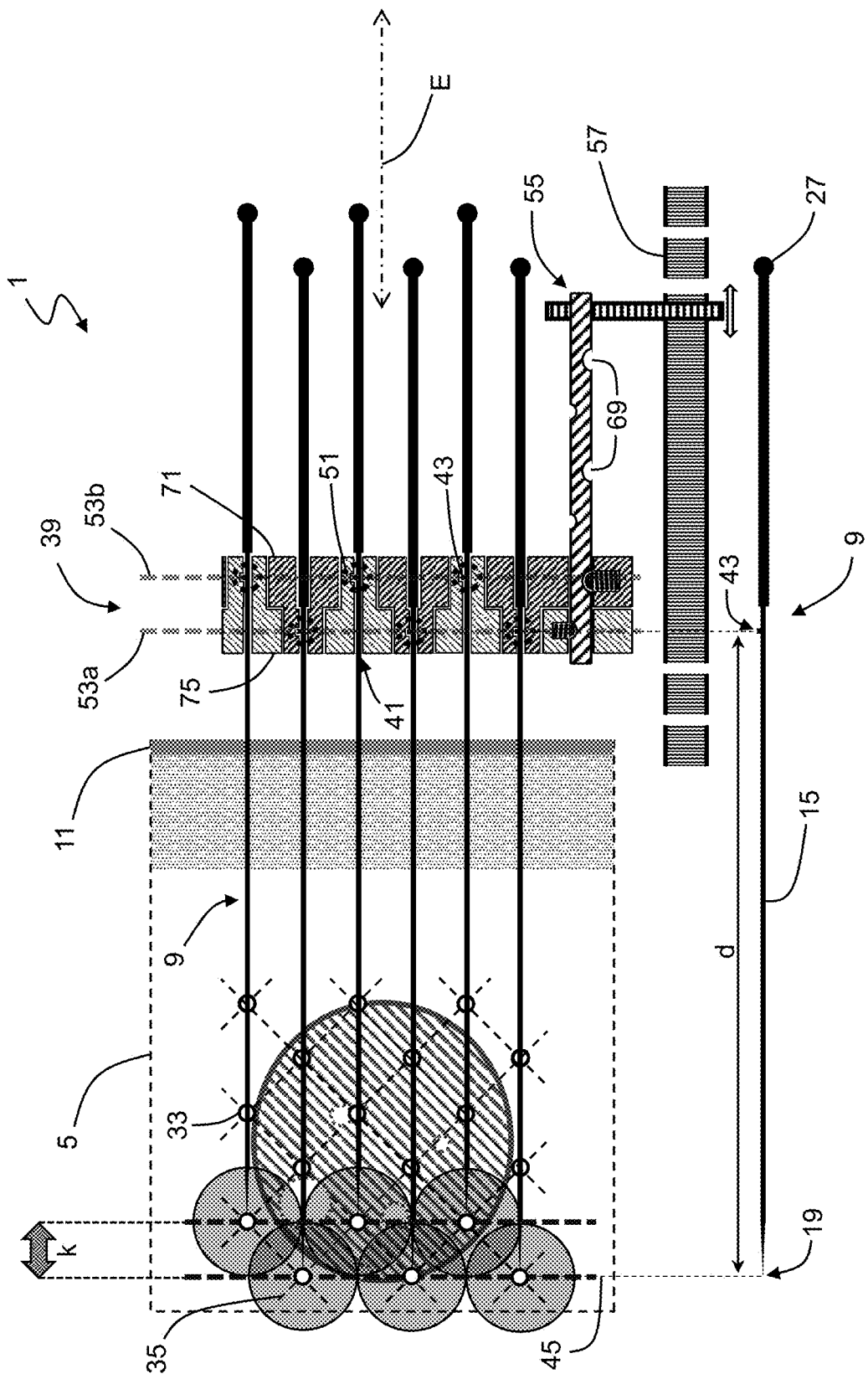
FIG. 34 is a schematic representation of the system shown in FIG. 33 with applicator tips in a first and second target point grid area.
Figure 35:
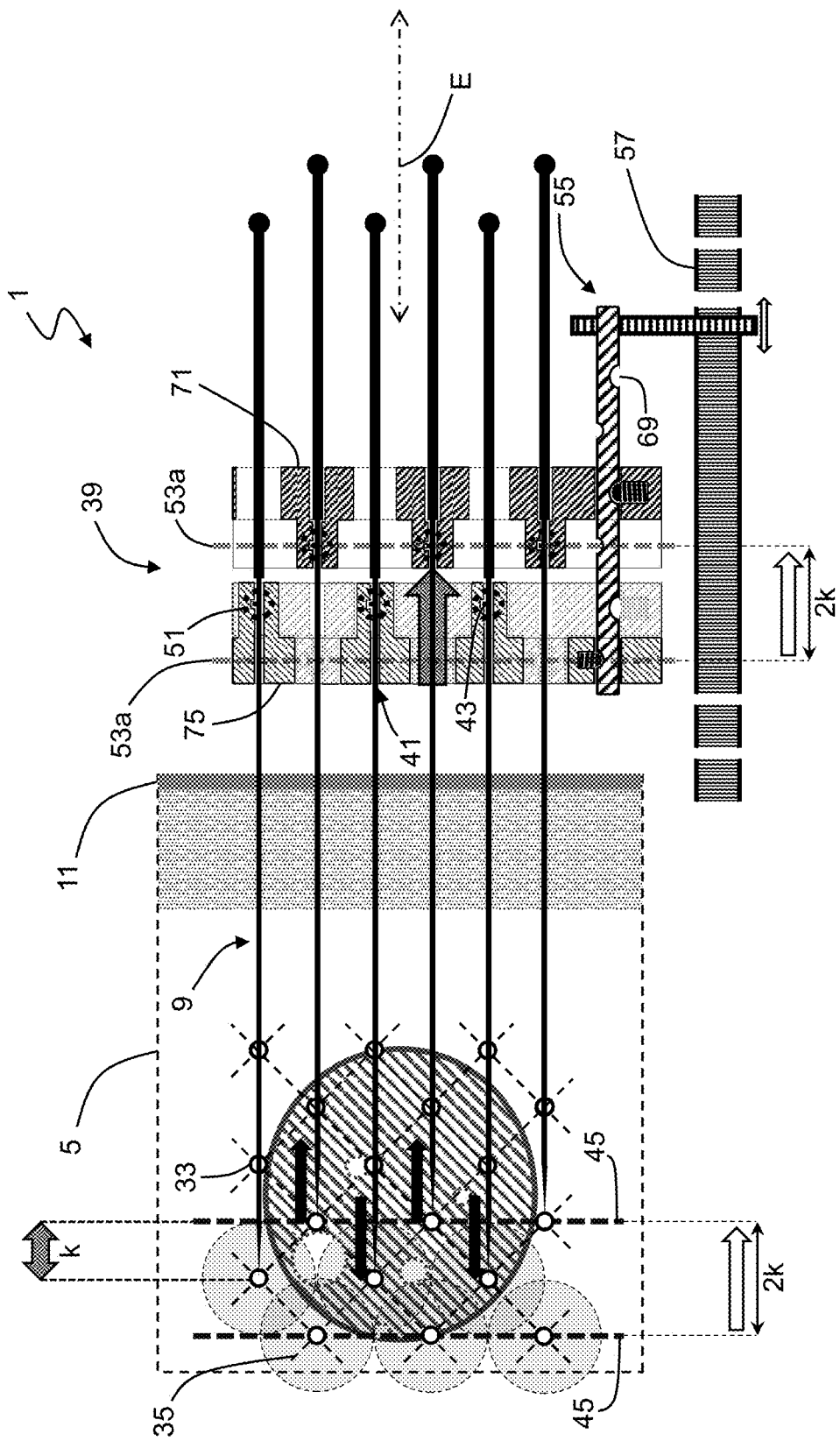
FIG. 35 is a schematic representation of the system shown in FIGS. 33 and 34 with a first subset of applicators in a first template part, the applicator tips of which are pulled towards a third target point grid area, while a second subset of applicators is held in a second template part.
Figure 36:
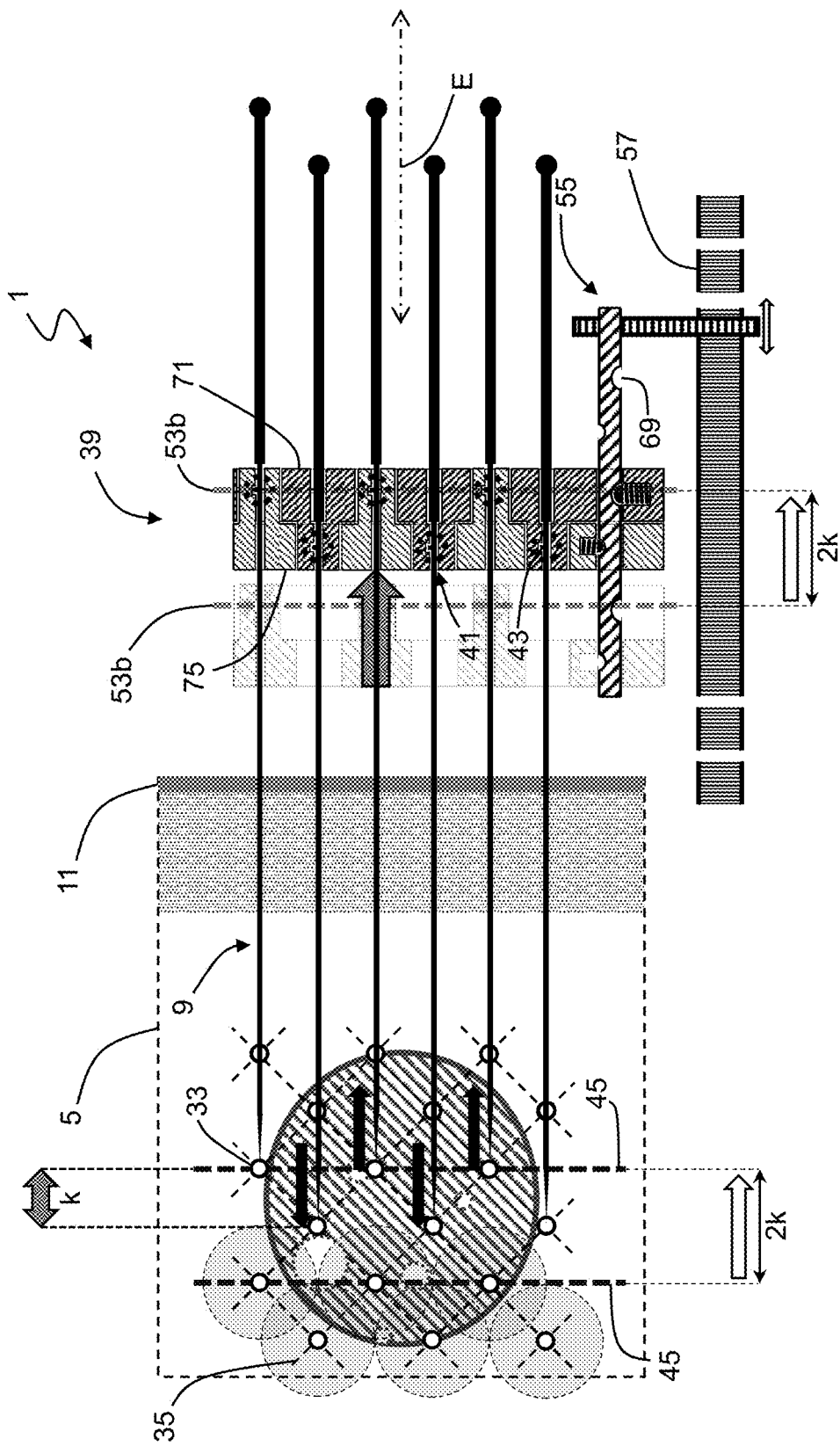
FIG. 36 is a schematic representation of the system shown in FIG. 35, wherein the applicator tips of the first subset of applicators are held in the third target point grid area, while the applicator tips of the second subset of applicators are pulled towards a fourth target point grid area.

However, under certain circumstances, the avoidance of the "dragging effect" may only function in a limited manner in this exemplary embodiment, which is illustrated in FIG. 32 by the unintentionally changed position of the organ 3 and will be explained in detail below. The static frictional force that a light applicator 9 exerts on the organ 3 when said light applicator is pulled out is in direct proportion to the light applicator shaft lateral surface or—if the light applicator diameter remains the same—to the light applicator shaft length that is covered by tissue of the organ 3. This leads to the fact that the "dragging effect" cannot be suppressed in certain situations despite the division of the placement template 39 into two template parts 71 and 75 and the sequential movement of these template parts 71 and 75. This is very clear in the previously explained exemplary embodiment. If, starting from FIG. 30, the first template part 71 is moved in the proximal direction by 2 k, which is ultimately completed in FIG. 31, the subset of light applicators 9 which is fixed in the first template part 71 and is to be moved therewith is initially covered by tissue of the organ 3 over a similar shaft length as the subset of light applicators 9 which is fixed in the second template part 75 and is to be moved therewith later, but initially remains in place and position according to the procedure described above. The difference in length in relation to the tissue coverage is only k, which is illustrated in FIG. 30 by the thick, dark grey, double arrow at the top left of the figure. Moreover, because all the light applicators 9 are still very far inside the organ 3, this difference in length is only of secondary importance. Consequently, the sum of the static frictional forces exerted on the organ 3 during the movement of the first template part 71 by its subset of light applicators 9 is similar in amount to the sum of the static frictional forces acting in the opposite direction of the subset of unmoved light applicators 9 of the second template part 75.

However, if then, starting from FIG. 31 and at the transition to FIG. 32, the second template part 75 with its subset of light applicators 9 is then retracted, then the subset of light applicators 9, which is fixed in the first template part 71 and now remains in place and position according to the procedure described above, is covered by a length 3 k to a lesser extent with tissue of the organ 3 than the subset of light applicators 9, which is fixed in the second template part 75 and is now retracted in the proximal direction, which is illustrated in FIG. 31 is illustrated by the thick, dark grey, double arrow at the top left of the figure. However, because the subset of light applicators 9 of the first template part 71 is now only inserted over a relatively small shaft length in the organ 3, this already larger difference in length 3 k is of even greater significance. Consequently, the subset of the moving light applicators 9 of the second template part 75 exerts a significantly higher total static frictional force on the organ 3 than the subset of the stationary light applicators 9 of the first template part 71. There can then no longer be any question of compensation of the static frictional forces when the second template part 75 is moved or retracted. The resulting total static frictional force is therefore clearly different from zero, which leads to the organ 3 being entrained by the subset of light applicators 9 of the second template part 75 in the proximal direction, as already shown schematically in FIG. 25b, and to a changed position in the body 5, as shown in FIG. 32. Consequently, after the displacement of template parts, the target point grid structure 35 no longer covers the organ 3 in the originally intended manner, as was still the case at the beginning and as is shown, for example, in FIG. 29. This means that the treatment can no longer be carried out in the originally planned simple, fast, defined and—with regard to gap-free irradiation—reliable manner.

A solution to the problem described above is shown by the procedure explained on the basis of the exemplary embodiment of FIGS. 33 to 36. It is characterising for this procedure, provided the second template part 75 is displaceable in the proximal direction relative to the first template part 71 only until it is in contact with the first template part 71, that when the second template part 75 is in contact with the first template part 71, the first subset 73 of the fixing point receptacles 51 defined by the first template part 71 is located distally from the second subset 77 of the fixing point receptacles 51 defined by the second template part 75. In other words, the fixing point receptacles 51 of the second template part 75 are no longer located in the fixing point receptacle grid area 53a of the second template part 75, as was the case in the previous exemplary embodiment, see for example FIG. 29, but in the fixing point receptacle grid area 53b of the first template part 71. Conversely, the fixing point receptacles 51 of the first template part 71 are now no longer located in the fixing point receptacle grid area 53b of the first template part 71, but in the fixing point receptacle grid area 53a of the second template part 75; see FIG. 33.

As a result, regardless of which subset of light applicators 9 is moved, the difference in the shaft length covered by tissue of the organ 3 is never greater than the length k (see FIGS. 34, 35 and 36), whereas in the previous exemplary embodiment this difference can be 3 k, i.e. three times as great, see FIG. 31. Accordingly, the undesirable "dragging effect" can be largely avoided and the treatment can be carried out in the planned simple, fast, defined and—with regard to gap-free irradiation—reliable manner.

While specific embodiments of the invention have been shown and described in detail to illustrate the application of the principles of the invention, it will be understood that the invention may be embodied otherwise without departing from such principles.

LIST OF REFERENCE SIGNS 1 system
3 organ
4 surrounding tissue directly connected to the organ 3
5 body
7 pathological tissue region
9 light applicator
10 first light applicator
11 skin
13 distal end of the insertion portion
15 insertion portion of the light applicator
17 light-emitting element/LED
19 applicator tip
21 light sphere
23 supply unit
25 port
27 grip element
29 cable
31 plug
33 target point
35 target point grid structure
37 fixing point grid structure
39 placement template
41 guide
43 fixing point
44 fixing point
45 target point grid area
47 fixing point grid area
51 fixing point receptacle
53 fixing point receptacle grid area
53a fixing point receptacle grid area
53b fixing point receptacle grid area
55 fastening device
57 reference surface
59 engagement element
61 engagement receptacle
63 protrusion
65 receptacle securing means
67 engagement element
69 engagement receptacle
71 first template part
73 subset of guides or light applicators
75 second template part
77 subset of guides or light applicators

What is claimed is:

1. A system for performing transcutaneous photodynamic therapy (PDT) in an organ or an organ segment of an organic body, the system comprising:
   a plurality of individually manually placeable light applicators, wherein the light applicators each comprise a needle-shaped insertion portion for transcutaneous piercing along a piercing axis into the organ or organ segment, a light-emitting applicator tip at a distal end of the insertion portion, and at least one defined fixing point at a proximal distance from the applicator tip;
   a supply unit configured to supply the light applicators with light and/or power; and
   a placement template placeable in a defined position relative to the organic body for defined orientation, placement, and fixing of the individual light applicators, the placement template defining a plurality of fixing point receptacles by means of which the light applicators are fixable with the respective at least one defined fixing point, the placement template comprising at least one first template part defining a first subset of the fixing point receptacles and at least one second template part defining a second subset of the fixing point receptacles, wherein the first template part is guidingly displaceable relative to the second template part along the piercing axis.

2. The system according to claim 1, wherein the first subset of the fixing point receptacles defines a first fixing point receptacle sub-grid and the second subset of the fixing point receptacles defines a second fixing point receptacle sub-grid, wherein the second fixing point receptacle sub-grid is offset from the first fixing point receptacle sub-grid by a lateral grid offset transversely to the piercing axis.

3. The system according to claim 1, wherein the lateral grid offset is smaller than a side length of a grid elementary cell of the first fixing point receptacle sub-grid and/or the second fixing point receptacle sub-grid.

4. The system according to claim 2, wherein the first fixing point receptacle sub-grid and the second fixing point receptacle sub-grid lie in a fixing point receptacle grid area.

5. The system according to claim 1, wherein the first subset of the fixing point receptacles, the second subset of the fixing point receptacles and the light applicators together define a three-dimensional fixing point grid structure, wherein the fixing point grid structure corresponds to a virtual organ-specific target point grid structure for the light-emitting applicator tips in the organ or organ segment and is parallel-displaced relative to the target point grid structure by a distance d along the piercing axis, wherein each light applicator has at least one defined fixing point at the distance from the light-emitting applicator tip.

6. The system according to claim 1, wherein the supply unit is set up to supply power to the light applicators and each light applicator comprises an LED at the distal end of the insertion portion, said LEDs being operable with the power.

7. The system according to claim 1, wherein the light applicators each have at least one fixing point which is formed by a stop and is configured to be locked.

8. The system according to claim 5, wherein the virtual organ-specific target point grid structure has a plurality of target points arranged spatially distributed on target point grid areas, wherein the target point grid areas are spaced apart from each other by a distance along the piercing axis.

9. The system according to claim 8, wherein at least eight of the target points form corner points of a grid elementary cell of the target point grid structure in the form of a parallelepiped.

10. The system according to claim 9, wherein the grid elementary cell has three grid elementary cell edges and four grid elementary cell diagonals, one of which runs along the piercing axis.

11. The system according to claim 8, wherein a first subset of the target points corresponding to the first subset of the fixing point receptacles defines a first target point sub-grid and a second subset of the target points corresponding to the second subset of the fixing point receptacles defines a second target point sub-grid, such that the first target point sub-grid and the second target point sub-grid supplement each other to form one of the target point grid areas.

12. The system according to claim 8, wherein the light applicators each comprise at least two fixing points, which are spaced apart from each other by a distance along the piercing axis.

13. The system according to claim 1, wherein the second template part is displaceable in the proximal direction relative to the first template part up to the second template part contacting the first template part, wherein, with the second template part in contact with the first template part, the first subset of the fixing point receptacles, defined by the first template part, lies distally of the second subset of the fixing point receptacles, defined by the second template part.

14. The system according to claim 1, wherein the fixing point receptacles are arranged distributed on fixing point receptacle grid areas, wherein the fixing point receptacle grid areas are spaced apart from each other by a distance along the piercing axis.

15. The system according to claim 14, wherein the first template part comprises a first subset of the fixing point receptacles of a first fixing point receptacle grid area and the second template part comprises a second subset of the fixing point receptacles of a second fixing point receptacle grid area.

* * * * *